(12) United States Patent
Vande Velde

(10) Patent No.: US 8,192,747 B2
(45) Date of Patent: Jun. 5, 2012

(54) LIVE ATTENUATED ROTAVIRUS VACCINE FOR ORAL ADMINISTRATION

(75) Inventor: Vincent Vande Velde, Rixensart (BE)

(73) Assignee: GlaxoSmithKline Biologicals, s.a., Rixensart (BE)

( * ) Notice: Subject to any disclaimer, the term of this patent is extended or adjusted under 35 U.S.C. 154(b) by 203 days.

(21) Appl. No.: 11/816,443

(22) PCT Filed: Feb. 15, 2006

(86) PCT No.: PCT/EP2006/001442
§ 371 (c)(1),
(2), (4) Date: Aug. 16, 2007

(87) PCT Pub. No.: WO2006/087205
PCT Pub. Date: Aug. 24, 2006

(65) Prior Publication Data
US 2008/0166372 A1    Jul. 10, 2008

(30) Foreign Application Priority Data

Feb. 17, 2005  (GB) .................................. 0503337.8

(51) Int. Cl.
*C12N 7/00*    (2006.01)
(52) U.S. Cl. ................. 424/215.1; 424/184.1; 424/235.1
(58) Field of Classification Search .................. None
See application file for complete search history.

(56) References Cited

U.S. PATENT DOCUMENTS

| | | | | |
|---|---|---|---|---|
| 5,384,311 A | * | 1/1995 | Antenucci et al. ............... | 514/53 |
| 5,932,223 A | * | 8/1999 | Burke et al. ............... | 424/215.1 |
| 6,534,065 B1 | * | 3/2003 | Makin et al. ............... | 424/206.1 |
| 6,616,931 B1 | * | 9/2003 | Burke et al. ............... | 424/215.1 |
| 6,919,076 B1 | * | 7/2005 | Green et al. ................. | 424/94.5 |

FOREIGN PATENT DOCUMENTS

| | | | |
|---|---|---|---|
| EP | 0 557 427 | | 9/1993 |
| WO | WO 93/02701 | * | 2/1993 |
| WO | WO 01/12797 | | 2/2001 |
| WO | WO 01/12797 | * | 4/2001 |
| WO | WO 01/54718 | | 8/2001 |
| WO | WO 02/11540 | | 2/2002 |

OTHER PUBLICATIONS

Parez, Rotavirus gastroenteritis: Why to back up the development of new vaccines?, 2008, Comparative Immunology, Microbiology and Infectious Diseases, vol. 31, pp. 253-269.*

Clark, H.F., et al., "Safety and Immunogenicity and Efficacy in Healthy Infants of G1 and G2 Human Reassortant Rotavirus Vaccine in a New Stabilizer/Buffer Liquid Formulation," *Pediatric Infectious Disease Journal*, vol. 22, No. 10, pp. 914-920 (2003).

Vesikari, T., et al., "Safety and immunogenicity of RIX4414 Live Attenuated Human Rotavirus Vaccine in Adults, Toddlers and Previously Uninfected Infants," *Vaccine*, vol. 22, No. 21-22, pp. 2836-2842 (2004).

* cited by examiner

*Primary Examiner* — Agnieszka Boesen
(74) *Attorney, Agent, or Firm* — Gwynedd Warren; GlaxoSmithKline Global Patents

(57) ABSTRACT

This invention provides liquid rotavirus formulations that are suitable for oral administration to human infants. In particular, the invention provides pharmaceutical compositions and vaccines, comprising a rotavirus antigen, a sugar and a carboxylate, wherein said formulation has a pH of between pH 5.0 and pH 8.0 and comprises no phosphate or less than 5 mM phosphate. The invention also provides methods of preparing said rotavirus formulations and use thereof in the prevention or treatment or rotavirus associated diseases in humans.

33 Claims, 4 Drawing Sheets

FIG. 1    Standard acid base titration curves of four carboxylates
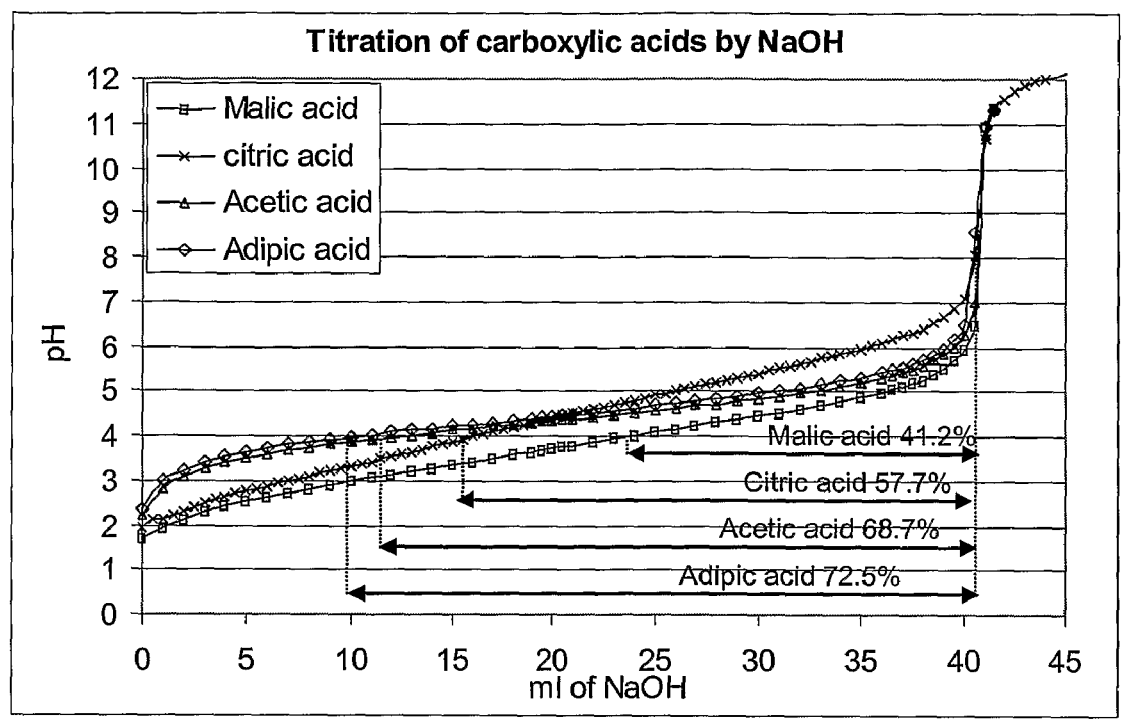

FIG. 2A          Antacid capacity of various adipate formulations
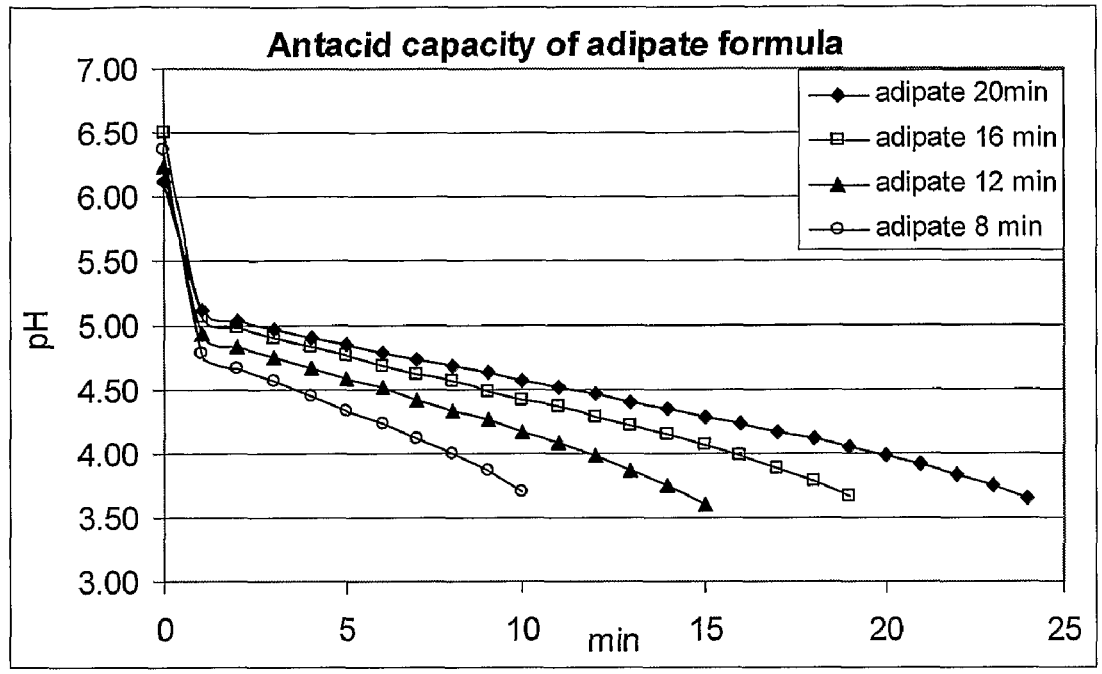
FIG. 2B          Experimental set-up of the Baby Rossett-Rice test
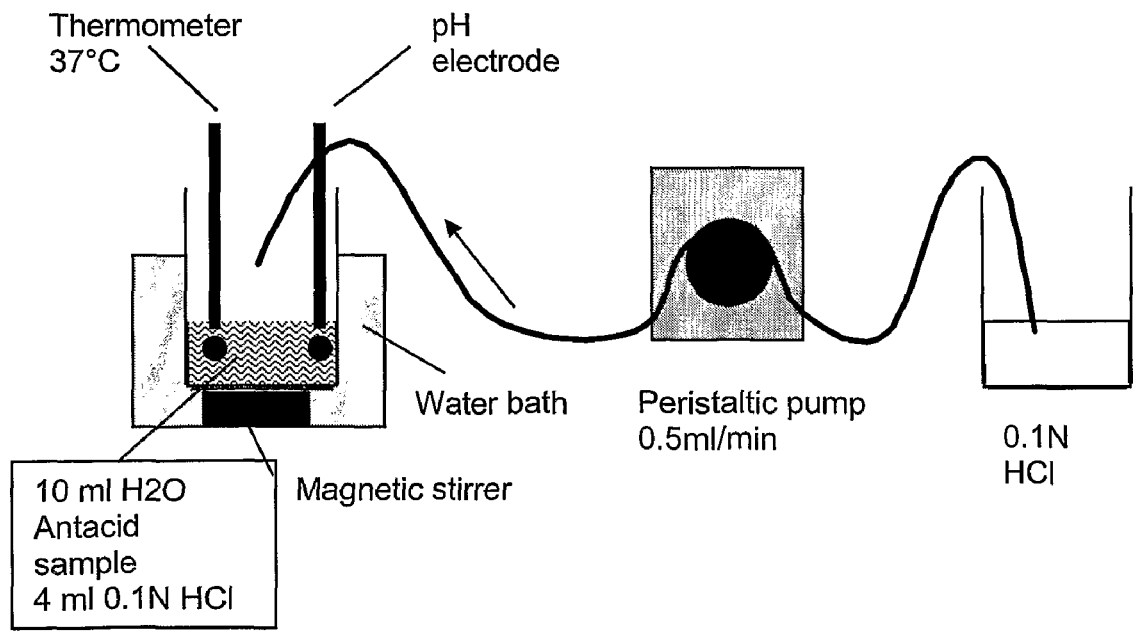

FIG. 3A    Refractive index of the adipate-containing formulations
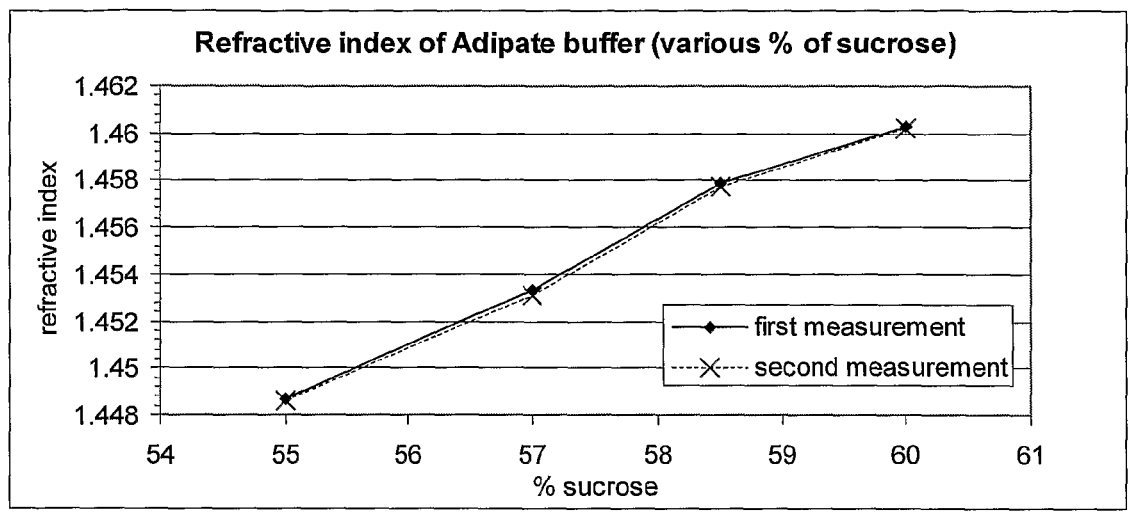
FIG. 3B    Refractive index of the adipate-containing formulations
(Rotavirus placebo)
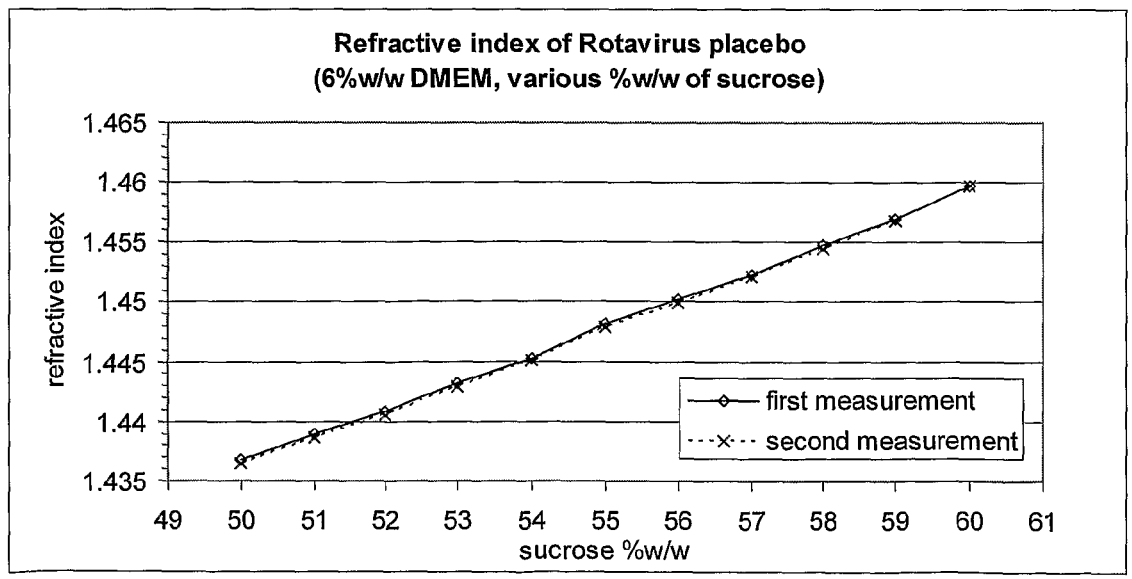

FIG. 4  Study design overview
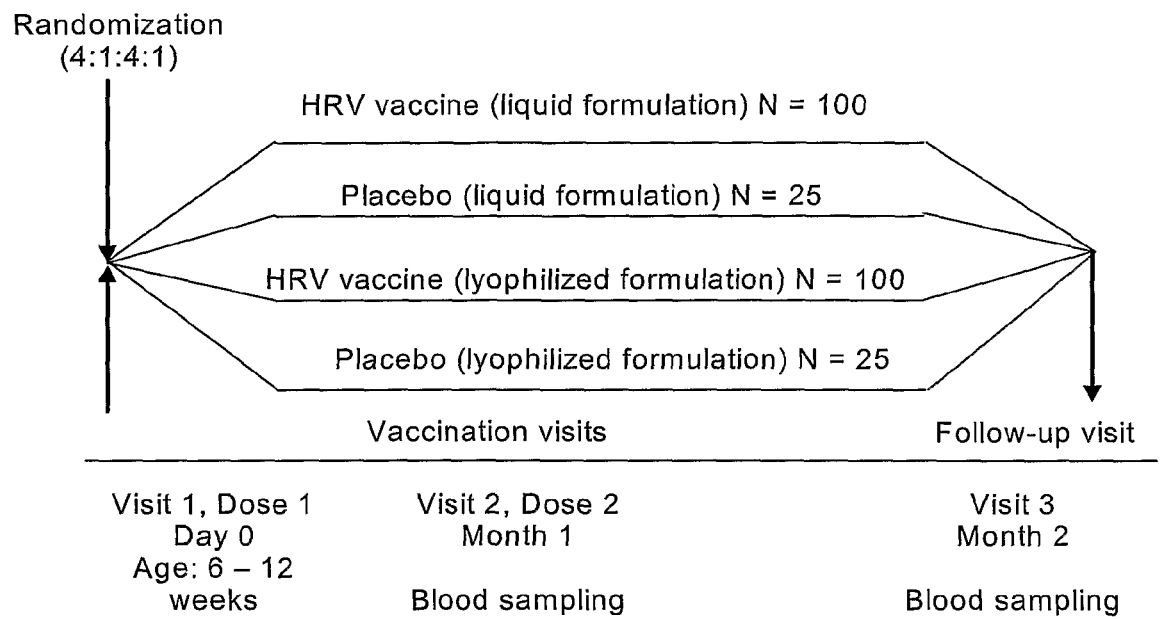

LIVE ATTENUATED ROTAVIRUS VACCINE FOR ORAL ADMINISTRATION

TECHNICAL FIELD

The present invention relates to novel liquid rotavirus formulations that are useful as pharmaceutical compositions and vaccines, to method for preparing them and to their use in preventing rotavirus, in particular human rotavirus associated diseases.

TECHNICAL BACKGROUND

Acute, infectious diarrhoea is a leading cause of disease and death in many areas of the world. In developing countries, the impact of diarrhoeal disease is very important. For Asia, Africa and Latin America, it has been estimated that there are between 3-4 billion cases of diarrhoea each year and of those cases about 5-10 million result in death (Walsh, J. A. et al.: N. Engl. J. Med., 301:967-974 (1979)).

Rotaviruses have been recognised as one of the most important causes of severe diarrhoea in infants and young children (Estes, M. K. Rotaviruses and Their Replication in Fields Virology, Third Edition, edited by Fields et al., Raven Publishers, Philadelphia, 1996). It is estimated that rotavirus disease is responsible for over 600,000 deaths annually. Rotavirus-induced illness most commonly affects children between 6 and 24 months of age, and the peak prevalence of the disease generally occurs during the cooler months in temperate climates, and year-round in tropical areas. Rotaviruses are typically transmitted from person to person by the faecal-oral route with an incubation period of from about 1 to about 3 days. Unlike infection in the 6-month to 24-month age group, neonates are generally asymptomatic or have only mild disease. In contrast to the severe disease normally encountered in young children, most adults are protected as a result of previous rotavirus infection so most adult infections are mild or asymptomatic (Offit, P. A. et al. Comp. Ther., 8(8):21-26, 1982).

Rotaviruses are spherical, and their name is derived from their distinctive outer and inner or double-shelled capsid structure. Typically, the double-shelled capsid structure of a rotavirus surrounds an inner protein shell or core that contains the genome. The genome of a rotavirus is composed of 11 segments of double-stranded RNA which encode at least 11 distinct viral proteins. Two of these viral proteins designated as VP4 (P protein) and VP7 (G protein) are structural proteins-arranged on the exterior of the double-shelled capsid structure. The inner capsid of the rotavirus presents one protein, which is the rotavirus protein designated VP6. The relative importance of these three particular rotavirus proteins in eliciting the immune response that follows rotavirus infection is not yet clear. Nevertheless, the VP6 protein determines the group and subgroup antigen, and VP4 and VP7 proteins are the determinants of serotype specificity.

To date, at least 14 rotavirus G serotypes and 11 rotavirus P serotypes have been identified (Linhares A. C. & Bresse J. S., Pan. Am. J. Publ. Health 2000, 9, 305-330). Among these, 10 G serotypes and 6 P serotypes have been identified among the human rotavirus.

VP7 protein is a 38,000 MW glycoprotein (34,000 MW when non-glycosylated) which is the translational product of genomic segment 7, 8 or 9, depending on the strain. This protein stimulates formation of the major neutralising antibody following rotavirus infection. VP4 protein is a non-glycosylated protein of approximately 88,000 MW which is the translational product of genomic segment 4. This protein also stimulates neutralising antibody following rotavirus infection. Since VP4 and VP7 proteins are the viral proteins against which neutralising antibodies are directed, they are believed to be prime candidates for development of rotavirus vaccines, affording protection against rotavirus illness.

Natural rotavirus infection during early childhood is known to elicit protective immunity.

Early vaccine development for preventing rotavirus infections began in the 1970s after the discovery of the virus. Initially, attenuated strains from animals and humans were studied, whilst more recent efforts have focused on human-animal reassortants.

The development of novel rotavirus formulations must comply with a number of requirements, including worldwide distribution potential and stability under a broad range of environmental and storage conditions. In particular, the stability of a formulation, especially of a pharmaceutical or vaccine composition, will in general be better at lower temperatures compared to room or higher temperatures.

Consequently one stabilisation method has been to develop vaccine formulations that can be stored frozen ($-20°$ C. to $-70°$ C.) or alternatively to develop lyophilised vaccines that can be kept for a prolonged period of time at around refrigerator temperature ($2°$ C. to $8°$ C.). However, it is a known fact that the lyophilisation process has a limiting capacity, and is associated with a high production cost. Furthermore, lyophilised vaccines have a more sophisticated handling for administration as they may require more complex, hence relatively expensive devices such as multichamber/vial vaccines, with the active ingredient in one chamber and the reconstitution liquid in another chamber. Lyophilised vaccines are also associated with higher shipment and storage cost. These options may be inadequate for some countries in the developing world where the administration device has to be financially affordable and where the availability of production and storage infrastructure may be inexistent or unreliable.

As Rotavirus are conventionally administered orally to human infants, this route brings several challenges to immunogenic rotavirus compositions.

Rotavirus is rapidly inactivated in an acidic environment, upon exposure to acid buffer or acidic gastric juice for example (C. Weiss and H. F. Clark, 1985, J. Gen. Virol., 66, 2725-2730; T. Vesikari et al., 1984, The Lancet, page 700; R. H. Foster and A. J. Wagstaff, 1998, BioDrugs February: 9(2) 155-178). Therefore it is desirable that rotavirus compositions are formulated in a way that they are stable during storage and after administration into the host recipient.

Rotavirus vaccines are primarily intended to be administered to babies, as early as at the age of 4 weeks. A small vaccine dose volume, such as lower than 2 ml or even than 1.5 ml dose volume, will be advantageous for that population. Therefore, it is desirable that rotavirus compositions are formulated in a small dose volume.

Stabilising formulations for liquid viral vaccines are known. For example, EP 0 065 905 discloses in general stabilising compositions suitable for a series of viruses such as those causing measles or influenza, and in particular it discloses stabilizing phosphate buffer-containing solutions suitable for live attenuated virus.

Other stabilizing formulations are disclosed in WO 98/13065 and in Clark et al. (Pediatr Infect Dis J. 2003 October; 22(10):914-20). Such formulations also require, amongst other constituents, the presence of phosphate to act as a buffering agent to neutralise stomach acidity. These formulations are however not compatible with the requirements set out above for the successful development of a rotavirus formulation, specifically they are not compatible with a reduced volume of the vaccine dose that is best suited for a human infant. In particular, the present inventor has found that adapting this prior art formulation into a low volume setting such as 1.5 ml or lower, whilst maintaining efficient antacid capacity, leads to problems arising from inappropriate concentration of the formulation constituents, in particular phosphate buffer.

There is a need therefore to develop alternative rotavirus formulations, in particular alternative liquid formulations that can withstand gastric acidity, and are refrigerator-stable despite the absence of phosphate. In addition there is a need that such alternative formulations be also successfully formulated in a vaccine dose volume as small as possible.

Therefore the present invention not only provides alternative stable immunogenic compositions that are devoid of phosphate or contain only minimal amounts of phosphate, but also allow rotavirus to be formulated in a low dose volume that are suitable for oral administration to human infants.

DESCRIPTION OF FIGURES

FIG. 1—Standard acid base titration curves for four carboxylates

FIG. 2A—Antacid capacity of various adipate-containing formulations

FIG. 2B—Experimental set-up of the Baby Rossett-Rice assay

FIG. 3—Refractive index of adipate-containing formulations. FIG. 3A shows that at the adipate buffer step the target value is sucrose 58.5% w/w which gives a refractive index of 1.4578 in the mixture. FIG. 3B shows that at the final formulation step the target is sucrose 55% w/w which leads to a refractive index of 1.4480.

FIG. 4—Phase II clinical study design overview

STATEMENT OF THE INVENTION

Accordingly, in a first aspect of the present invention, there is provided a liquid rotavirus immunogenic composition which is suitable for oral administration to a human infant, comprising a rotavirus antigen, a sugar and a carboxylate wherein said composition has a pH of between about pH 5.0 and about pH 8.0 and comprises less than 5 mM phosphate. Suitably the concentration of phosphate in the claimed composition does not exceed 1 mM.

In a specific aspect of the invention, a suitable vaccine dose will normally be 1.5 ml or suitably any volume smaller than 2.5 ml such as a volume of 2 ml or less, that is suitable for oral administration to babies or infants. In particular the dose volume will be such that the technical feasibility of the formulation is possible and there is no detrimental effect on the immunogenic potential of the formulation. The claimed compositions offer the advantage over prior art phosphate-containing formulations that they can withstand gastric acidity, remain immunogenic and stable over a long shelf-life, whilst being compatible with formulation in a dose volume smaller than usual, such as smaller than 2.0 ml or even compatible with a dose volume of 1.5 ml or smaller.

In a specific embodiment, the liquid immunogenic composition according to the invention has an antacid capacity of between 6 and 23 minutes as assessed by the Baby Rossett-Rice assay (adapted as detailed in Example III.2.2 from the basic Rossett-Rice test). Suitably the antacid capacity will be at least 8 minutes, typically at least 12 minutes, and a suitable range is between 12 and 20 minutes. Surprisingly, the claimed compositions have shown a not only acceptable but higher antacid capacity even in a smaller dose volume, compared to phosphate-containing prior art formulations.

In another aspect, there is provided a method for the preparation of said liquid rotavirus immunogenic composition comprising admixing a rotavirus antigen, a sugar and a carboxylate with a pharmaceutically acceptable diluent.

The invention also covers in another aspect the use of a rotavirus antigen in admixture with a carboxylate and a sugar for the manufacture of an oral immunogenic composition for the prevention or treatment of rotavirus associated diseases in humans wherein said composition does not contain more than 5 mM phosphate and has a pH of between about pH 5.0 and about pH 8.0.

In a still further aspect a method of treating or preventing rotavirus associated diseases in humans by administering to a human subject in need thereof an effective amount of said liquid immunogenic composition is also provided.

Other aspects and advantages of the present invention are described further in the following detailed description of the preferred embodiments thereof.

DETAILED DESCRIPTION

The present inventor has developed novel liquid rotavirus compositions that are immunogenic, stable at refrigerator-temperature (between 2 and 7° C., typically at 4° C.), that can withstand the inherent acid nature of the stomach when administered orally and that are compatible with a small dose volume.

A liquid composition is intended to mean a formulation in a fluid form, as opposed to a dry form, whose volume is fixed under constant specific conditions (for example, at room temperature or refrigerator-temperature, at atmospheric pressure) and whose shape is determined by the container it fills.

The subject matter of and information disclosed within the publications and patents or patent applications mentioned in this specification are incorporated by reference herein.

The terms 'comprising', 'comprise' and 'comprises' herein is intended by the inventor to be optionally substitutable with the terms 'consisting of', 'consist of', and 'consists of', respectively, in every instance.

The present invention provides for a liquid rotavirus immunogenic composition comprising a rotavirus antigen, a sugar and a carboxylate wherein said composition has a pH of between about pH 5.0 and about pH 8.0 and comprises less than 5 mM phosphate. The compositions of the invention show a very good stability profile when compared to phosphate-containing formulations, whilst the immunogenicity profile is maintained. These compositions are at least as stable as their phosphate-containing counterparts. A further advantage of the present compositions is that they can be prepared in a small dose volume such as lower than 2.0 ml, typically 1.5 ml for example, compared to prior art formulations in which phosphate is present.

In a specific embodiment, the concentration of phosphate within the immunogenic composition does not exceed 5 mM, suitably 1 mM, in particular it does not exceed 0.5 mM. Phosphate refers as the salt of phosphoric acid (also known as orthophosphoric acid ($H_3PO_4$)), usually sodium or potassium or mix of sodium and potassium salts are used (for example: $Na_3PO_4$, $Na_2HPO_4$, $NaH_2PO_4$, $K_3PO_4$, $K_2HPO_4$, $KH_2PO_4$). Suitably, phosphate concentration is 0.4 mM or below, typically 0.2 mM or below, ideally 0.1 mM or below. In another specific embodiment, the composition as claimed herein is free of phosphate. Typically phosphate, when present, comes from the cell culture medium or saline buffer used as a diluent, such as DMEM (Dulbecco's modified Eagle Medium), Eagle BME basal medium or PBS.

The phosphate concentration to which it is referred throughout the specification will be a calculated concentration, as determined from the amount(s) of phosphate-containing chemicals operated in the preparation of the claimed composition(s). Alternatively, the concentration of phosphate present in the composition as claimed herein may be measured experimentally using analytical routine techniques.

One suitable technique is a colorimetric assay named 'Nanocolor' marketed by Macherey-Nagel (catalog no 918 78). This method is based on the photometric determination of the yellow complex formed by phosphoric acid-molybdate-vanadate in an acid solution. The limit of quantitation of the assay is 2 μg/ml phosphate or 0.02 mM.

An alternative method is the dosage of phosphorus (P) by an atomic emission spectroscopy technique such as Incutively Coupled Plasma-Atomic Emission Spectroscopy (ICP-AES) (Boss & Fredeen, in Concepts, Instrumentation, and Techniques in Inductively Coupled Plasma Optical Emission Spectroscopy, Perkin Elmer eds, second edition, 1997—see Methodology on page 72 onwards). The limit of quantitation of the assay is 0.030 μg/ml phosphorus corresponding to a phosphate concentration of 0.00032 mM.

In one embodiment, the pH of the composition is between pH 5.0 and pH 8.0. In another specific embodiment, the pH of the claimed composition is between about pH 5.5 to about pH 7.5. By 'about pH' is meant within 0.2 units of the stated pH value. In particular, the pH of the composition is between pH 5.5 and pH 7.5. For example, the pH of the composition is between about pH 6.0 to about pH 7.0, in particular between pH 6.0 and pH 7.0, typically between pH 6.2 and pH 6.8 or between pH 6.2 and pH 6.6. A pH of about 6.4, in particular of 6.4, is contemplated. It is known that rotavirus is negatively affected at acidic pH such as a pH below 4.0, and would be expected that a maximum stability is obtained at a neutral or even slightly basic pH, i.e. a pH range of 7.0 to 8.0, which is obtained for example in the prior art phosphate buffered formulations. As shown in the experimental section, the compositions of the invention, despite the absence of phosphate, have shown a good stability profile at the claimed pH range, and furthermore have surprisingly shown an acceptable stability and immunogenicity profile even under mildly acidic conditions, i.e. around pH 6.0 to 7.0, such as at a pH of around 6.4 for example.

The liquid composition as claimed herein comprises a carboxylate.

The carboxylate ("—COO—") is the dissociated form of the carboxylic acid resulting of the neutralization of the acidic function ("—COOH") by a basic substance. A carboxylic acid is a compound containing the carboxyl group: "—COOH"; which is formally made by combining carbonyl group ("—CO—") and an hydroxyl group ("—OH"). However, interaction between these two parts so modifies their chemical properties that the entire group is considered as a new function with its own characteristic properties (Organic Chemistry by J. B. Hendrickson, D. J. Cram, and G. S. Hammond, McGraw-Hill Book Company, third edition 1970 page 131). Although the International Union for Pure and Applied Chemistry (IUPAC) recommend to use the alkaneoic acid (for monocarboxylic acids) and alkanedioic acid (for dicarboxylic acids) nomenclature, most of trivial names of the carboxylic acids have been used in this text because these products are well known by the skilled person in the Art. For example the IUPAC name of acetic acid is the ethanoic acid and for adipic acid the name will be hexanedioic acid.

In a specific embodiment, a carboxylate salt from an inorganic acid or, suitably, from an organic acid is used. In a specific embodiment, said carboxylate is derived from a weak acid. For example, said carboxylate is a carboxylate salt selected from the group consisting of: adipate, citrate, malate, acetate, succinate, propionate, butyrate, malonate, glutarate, maleate, glycolate, lactate, gluconate, fumarate, tartarate, pimelate and any combination of two or more thereof. Suitable carboxylates are carboxylates derived from a carboxylic acid with a $pK_a > 4$ or carboxylates derived from a di- or tri-carboxylic acid (di- or tri-carboxylates) with a numerical average $pK_a > 4$ (Table 9). Examples of the former class include carboxylates derived from propinic, butyric and acetic acid. Examples of the latter class include carboxylates derived from citric, maleic, malonic, succinic, adipic, glutaric and malic acid.

In a specific embodiment said carboxylate belongs to the GRAS list, i.e. carboxylates that are 'Generally Recognized As Safe by the Food and Drug Administration of the USA', and is selected from the list comprising acetate, propionate, malate, glutarate, adipate, lactate, fumarate, and tartrate. Suitably the carboxylate is a salt of adipic acid, i.e. monosodium salt of adipic acid, monopotassium salt of adipic acid, suitably disodium adipate or dipotassium adipate, or calcium adipate.

In a specific embodiment, a carboxylate concentration of between 50 mM to 2 M is suitably used in the liquid rotavirus composition. It will be understood that the carboxylate concentration within the range mentioned above may be suitably adapted, through routine experimentation, according to the nature of the carboxylate, the antacid capacity to be achieved and the volume of the vaccine dose. For example, high carboxylate concentrations of above 1 M can be used when a high antacid potential is required, such as above 8 minutes, suitably above 10 minutes, or above 12 minutes as assessed by the Baby Rossett Rice test for a dose volume of 1.5 ml. Concentrations of 1 M or below are typically used, such as concentrations of between 100 mM and 1 M, typically concentrations of between 200 mM and 800 mM. Suitable carboxylate concentrations are comprised between about 300 mM and about 800 mM, suitably between 400 mM and 700 mM. In particular, when the carboxylate is adipate a suitable concentration range is between 400 and 500 mM. However, the skilled person will recognise that concentrations within 10-20 percent of the stated values may be appropriate, i.e. when 100 mM is stated, a range of 80-90 mM to 110-120 mM is also disclosed and meant to be covered. Illustrative concentrations are given in Table 1 below for various carboxylates.

TABLE 1

Antacid capacity of carboxylates at a specific concentration
These illustrative parameters are given for a dose volume of 1.5 ml and correspond to the mentioned example number given in the Table 1.

| Carboxylate (Mw) | Carboxylate Concentration (M) | pH in BRR at t = 0 | Antacid capacity (min)* | Sample N° in Example II |
|---|---|---|---|---|
| Adipate (144) | 0.372 | 6.38 | 8 | 91 |
| Adipate (144) | 0.465 | 6.24 | 12 | 92 |
| Adipate (144) | 0.548 | 6.50 | 16 | 93 |
| Adipate (144) | 0.652 | 6.11 | 20 | 94 |
| D,L-malate (132) | 0.621 | 6.15 | 8 | 72 |
| D,L-malate (132) | 0.746 | 6.08 | 12 | 64 |
| D,L-malate (132) | 0.895 | 5.35 | 15 | 77 |
| Acetate (59) | 1.000 | 6.14 | 12 | 89 |
| Citrate (189) | 0.441 | 6.55 | 12 | 129 |

*assessed by the Baby Rossett Rice (BRR) test as adapted according to Example III.2.2

The pH of the liquid rotavirus immunogenic composition as claimed herein may be obtained by mixing of a carboxylic acid and a carboxylate salt. In particular, the carboxylic acid may be used in admixture with a different carboxylate salt, for example, a citrate is combined with adipic acid. This may be advantageous when using commercially available chemicals, some of which may not be readily available, or to simplify the formulation step. For example, one (or more) of said carboxylic acid(s) can be selected from the list consisting of: adipic acid, citric acid, malic acid, acetic acid, succinic acid, carbonic acid, propionic acid, butyric acid, malonic acid, glutaric acid, maleic acid, glycolic acid, lactic acid, gluconic acid, fumaric acid, tartaric acid, pimelic acid, and is (are) mixed in suitable proportions with one (or more) of carboxylate salts selected from the list consisting of: adipate, citrate, malate, acetate, succinate, propionate, butyrate, malonate, glutarate, maleate, glycolate, lactate, gluconate, fumarate, tartarate, pimelate.

The liquid composition as claimed herein comprises a sugar. Sucrose is particularly suitable. Dextrose is another suitable sugar. Other sugars or sugar alcohols can also be used in lieu of sucrose or dextrose, including for example: glycerol, erythrose, erythritol, xylitol, arabitol, ribose, xylose, arabinose, glucose, tagalose, mannose, galactose, fructose, inositol, sorbitol, mannitol, galactitol, glucose and fructose mix, maltose, sophorose, lactose, cellobiose, melibiose, trehalose, sucrose, palatinose, maltulose, lactulose, maltitol, lactitol, raffinose, maltotriose, melezitose, cellotriose, ciritol, maltotetraose, stachyose, cellotetraose, maltopentaose, cellopentaose, maltohexaose, cellohexaose, oligosaccharides.

Typical sugar concentrations range from about 1% w/w to about 70% w/w, for example from about 25% w/w to about 60% w/w. The skilled person will however recognise that the nature and concentration of sugar must be optimised such that it ensures satisfactory viral viability whilst maintaining the viscosity at a level that is compatible with downstream processing steps of the formulation, such as filtration. In a specific embodiment, sucrose is used. Typically, its concentration is maintained at a minimum of 30% w/w. Higher, i.e. above 30% w/w, sucrose concentrations can moreover be used to ensure long term storage, as it is expected that the high iso-osmotic pressure of such formulations will prevent bacterial growth. Accordingly, the lower limit for the concentration of sucrose in the liquid composition as claimed herein is suitably 30% w/w or higher, such as 35% W/W or higher, suitably 40% w/w or higher. A suitable sucrose concentration ranges from about 40% w/w to about 70% w/w. For example, a suitable concentration of sucrose will be between 45% w/w and 60% w/w, suitably between 50% w/w and 55% w/w. In particular, sucrose at a concentration of about 50% w/w or about 55% w/w is used. Final sucrose concentrations of 50% w/w or 55% w/w are suitable.

The skilled person will understand that routine optimisation of the sugar concentration can be carried out in order to ensure viral stability when another sugar is substituted for sucrose.

Furthermore, the stated values for sugars may be slightly adapted to take into account formulation/manufacturing parameters such as the dose volume. Therefore, the skilled person will recognise that concentrations within 10% of the stated values may be appropriate, i.e. when 50% w/w is stated, a range of 45% w/w-55% w/w is also disclosed and meant to be covered.

The liquid rotavirus immunogenic composition of the present invention also comprises a rotavirus antigen. In particular the liquid composition as claimed herein is an immunogenic composition, e.g. a vaccine composition. A rotavirus antigen is understood to mean any rotavirus antigen that is suitable for use in a vaccine formulation. Oral live rotavirus antigens are especially contemplated. For example, any suitable rotavirus antigen can be selected from the group consisting of: a live attenuated rotavirus from animals or humans, in particular a human live attenuated rotavirus; a reassortant rotavirus, in particular but not limited to a human-human reassortant rotavirus, a bovine-human reassortant rotavirus or a rhesus monkey-human reassortant rotavirus.

All rotavirus strains, human or animal strains, are contemplated in the present invention. Human rotavirus strains are suitable. In particular, rotavirus antigen is in one embodiment the attenuated human rotavirus population comprising a single variant or substantially a single variant, said variant being defined by the nucleotide sequence encoding at least one of the major viral proteins designated as VP4 and VP7 as disclosed in WO 01/12797, in particular any, including one or more, of the variants defined by the mutations set forth in Table 2, Tables 3.1 and 3.2 of WO 01/12797. In specific embodiments, the rotavirus antigen is any of the following human live attenuated rotavirus strains: HRV 89-12C2 strain deposited under accession number ATCC VR 2272 (as described in EP 0 557 427), its progeny, reassortants and immunologically active derivatives thereof; HRV P43 strain deposited under accession number ECACC 99081301 (as described in WO 01/12797), its progeny, reassortants and immunologically active derivatives thereof.

Rotavirus populations having the characteristics of any of the above mentioned deposited strains are also suitable vaccine strains. Derivatives from said deposited strains can be obtained by subjecting said strains to further processing such as by propagating them by further passaging, cloning, or other procedures using the live virus or by modifying said deposited strains in any way including by genetic engineering techniques or reassortant techniques. Such steps and techniques are well known in the art. Rotavirus antigens of particular interest are progeny of any of said deposited strains and immunologically active derivatives thereof. Immunologically active derivatives means materials obtained from or with any of the deposited strains, in particular from or with HRV P43 strain deposited under accession number ECACC 99081301, particularly antigens of the virus, which are capable of eliciting an immune response that is reactive against rotavirus when injected into a host animal.

Materials derived from the deposited strains recited above are also suitable rotavirus antigens, and include protein and genetic material. Of particular interest are reassortant rotaviruses which comprise at least one antigen or at least one segment of any of said deposited strains, for example reassortants which comprise a virulent strain of rotavirus in which one or part of one of the 11 genome segments has been replaced by the genome segment or part thereof of any of said deposited strains. Specifically, a rotavirus reassortant in which the segment or partial segment coding for NSP4 is a segment or partial segment of any of said deposited strains, may have useful properties. Reassortant rotaviruses and techniques for preparing them are well known (Foster, R. H. and Wagstaff, A. J. Tetravalent Rotavirus Vaccine, a review. ADIS drug evaluation, BioDrugs, Gev, 9 (2), 155-178, 1998).

The rotavirus antigen of the claimed composition may be produced according to routine production techniques. Typically rotavirus antigen preparations may be derived from tissue culture methods used to propagate the virus or express recombinant rotavirus antigens. Suitable cell substrates for growing the virus include for example dog kidney cells such as MDCK or cells from a clone of MDCK, MDCK-like cells, monkey kidney cells such as AGMK cells including Vero cells which are particularly suitable, other cells lines of monkey kidney origin such as BSC-1, LLC-MK2 and MA104, suitable pig cell lines, or any other mammalian cell type suitable for the production of rotavirus for vaccine purposes. Suitable cell substrates also include human cells e.g. MRC-5 cells. Suitable cell substrates are not limited to cell lines; for example primary cells are also included.

Also within the scope of the invention are admixtures of any of the above recited deposited strains with other rotavirus variants, for example other cloned variants or other reassortant rotavirus, or with other viruses in particular other attenuated viruses. In particular the composition according to the invention contains two rotavirus antigens. In particular one antigen within the composition is the HRV P43 strain deposited under accession number ECACC 99081301, and the other antigen is a reassortant derivative thereof or any immunologically active derivative thereof.

The rotavirus antigen for inclusion in the claimed composition can be a monovalent rotavirus strain, i.e. containing a single rotavirus strain, or be multivalent, i.e. containing at least two or more rotavirus strains.

The skilled person will understand that other readily available attenuated strains, from human or animal origin, that are obtainable from depository institutions are also suitable and may be used as substitutes for the recited deposited strains.

According to the present invention, a suitable immunogenic composition contains a rotavirus antigen, in particular the human attenuated P43 strain (as deposited under accession number ECACC 99081301, see WO 01/12797) at a concentration of $10^5$-$10^6$ ffu per dose (or equivalent to $10^{5.5}$-$10^{6.5}$ as expressed in CCID50 per dose), 55% sucrose w/w, di-sodium adipate 0.465 M (corresponding to 132.74 mg per dose), and has a pH of about 6.2 to 6.6, in a 1.5 ml dose volume. For this composition the DMEM content is 6% w/w and therefore represents less than 0.1 mM phosphate.

The composition according to the present invention may further include an additional antacid component such as an inorganic antacid, for example aluminium hydroxide $Al(OH)_3$ and magnesium hydroxide $Mg(OH)_2$. Aluminium hydroxide is a particularly suitable. Other commercially available antacids, which are suitable for use in the invention, include Mylanta™, which contains aluminium hydroxide and magnesium hydroxide. These are insoluble in water and are given in suspension. Another particularly suitable antacid that may be additionally used in the vaccine composition of the present invention is the insoluble inorganic salt, calcium carbonate ($CaCO_3$). A typical $CaCO_3$ concentration is 80 mg per vaccine dose for example.

Other suitable water insoluble antacids are magnesium carbonate, aluminium carbonate, aluminium phosphate, mix of aluminium hydroxide and magnesium carbonate, aluminium-magnesium-hydrocarbonate, aluminium hydroxide-magnesium carbonate-sorbitol-manitol, hydroxy-aluminium-sodium-carbonate, dihydroxy-aluminium-potassium-carbonate, magaldrate, hydrotalcite, almagcit, magnesium-aluminium-silicate-hydrate.

The immunogenic composition according to the present invention may additionally comprise pharmaceutically suitable compounds and/or carriers, in particular those known in the art as being suitable for oral administration, especially to infants. Such carriers include and are not limited to carbohydrates, polyalcohols, amino acids, aluminium hydroxide, magnesium hydroxide, hydroxyapatite, talc, titanium oxide, iron hydroxide, magnesium stearate, carboxymethylcellulose, hydroxypropylmethylcellulose, microcrystalline cellulose, gelatin, vegetal peptone, xanthane, caraghenane, arabic gum, β-cyclodextrin.

The composition according to the present invention may additionally comprise calcium ions which have been suggested to stabilise rotavirus.

Viscous agents may additionally be included present in the composition.

Possible viscous agents that may be used include pseudoplastic excipients. Suitable viscous agents include: propylene glycol, arabic gum, adragant gum, agar-agar, alginate, pectin, sodium carboxymethylcellulose (Tyloses C®), methylcellulose (Methocels A®, Viscotrans MC®, Tylose MH® and MB®), hydroxypropylmethylcellulose (Klucels®), hydroxypropylcellulose (Methocels E® and K®, Vicotrans MPHC®), Carbopol®, xanthane gum, Veegum® (Magnesium-aluminium silicate), Avicel® (about 89% microcrystalline cellulose and 11% Carboxymethylcellulose Na). Xanthane gum or starch are particularly suitable viscous agents for additional use in the liquid composition according to the invention.

It may also be advantageous to include in the claimed composition lipid-based vehicles such as virosomes or liposomes, oil in water emulsions or carrier particles. Alternatively or in addition immunostimulants such as those known in the art for oral vaccines may be included in the composition. Such immunostimulants include bacterial toxins, particularly cholera toxin (CT) in the form of the holotoxin (entire molecule) or the B chain only (CTB) and the heat labile enterotoxin of *E. coli* (LT). Mutated LTs (mLTs) which are less likely to convert to their active form than the native LT are described in WO 96/06627, WO 93/13202 and U.S. Pat. No. 5,182,109.

The composition according to the invention may further comprise an adjuvant or immunostimulant such as but not limited to detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

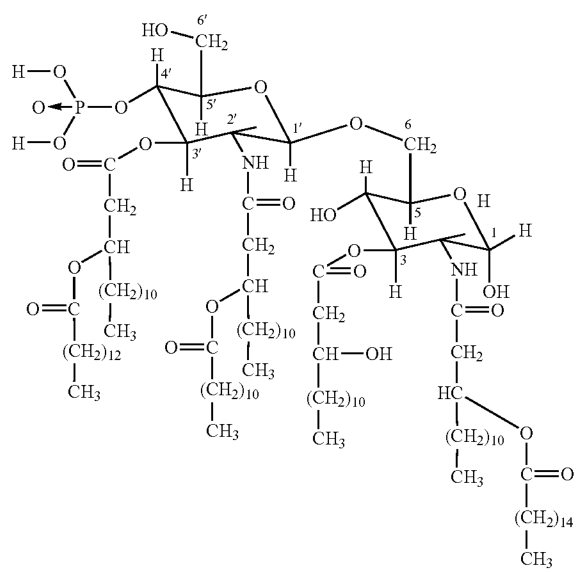

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A suitable form of 3D-MPL is in the form of an emulsion having a small particle size less than 0.2 μm in diameter, and its method of manufacture is disclosed in WO 94/21292. Aqueous compositions comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, *Int. Arch. Allergy. Immunol.*, 79(4):392-6; Hilgers et al., 1987, Immunology, 60(1):141-6; and EP 0 549 074 B1). A particularly suitable bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Synthetic derivatives of lipid A are also known including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Purified saponins as oral adjuvants are described in WO 98/56415. Saponins and monophosphoryl lipid A may be employed separately or in combination (e.g. WO 94/00153) and may be formulated in adjuvant systems together with other agents. 3D-MPL is a well-known adjuvant manufactured by Ribi Immunochem, Montana and its manufacture is described in GB 2122204.

Another preferred immunostimulant for use in the present invention is Quil A saponin and its derivatives. Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., *Crit. Rev Ther Drug Carrier Syst,* 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. QS-21 is a natural saponin derived from the bark of *Quillaja saponaria Molina*, which induces CD8+ cytotoxic T cells (CTLs), Th1 cells and a predominant IgG2a antibody response and is a suitable saponin in the context of the present invention. Other saponins which have been used in systemic vaccination studies include those derived from other plant species such as *Gypsophila* and *Saponaria* (Bomford et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739. The saponins forming part of the present invention may be separate in the form of micelles, or may be in the form of large ordered structures such as ISCOMs (EP 0 109 942 B1) or liposomes) when formulated with cholesterol and lipid, or in the form of an oil in water emulsion (WO 95/17210). The saponins may suitably be associated with a metallic salt, such as aluminium hydroxide or aluminium phosphate (WO 98/15287).

A particularly potent adjuvant composition involving QS21 and 3D-MPL in an oil in water emulsion is described in WO 95/17210 and in WO 99/11241 and WO 99/12565, and are suitable compositions.

A general discussion of vehicles and adjuvants for oral immunisation can be found in Vaccine Design, The Subunit and Adjuvant Approach, edited by Powell and Newman, Plenum Press, New York, 1995.

The vaccine composition according to the invention may contain additional components including for example flavourings (particularly for an oral vaccine) and bacteriostatic agents.

In a specific embodiment, the liquid composition according to the invention has an antacid capacity of between 6 and 23 minutes as assessed by the Baby Rossett-Rice assay (adapted as detailed in Example III.2.2 from the basic Rossett-Rice test). According to the present invention, by 'antacid capacity' is meant the period of time, expressed in minutes, during which the pH of the formulation under test remains above 4 as assessed according to the experimental procedure given in Example III.2.2. Suitably the antacid capacity will be between 12 and 20 minutes. An antacid capacity higher than 23 minutes such as 29-30 minutes for example is also perfectly acceptable from a vaccine development perspective but such a high capacity is superfluous. In particular, an antacid capacity of at least 8 minutes, at least 10 minutes, at least 12 minutes is especially contemplated. An antacid capacity of at least 12 minutes, at least 13 minutes, at least 14 minutes, at least 15 minutes, at least 16 minutes, is suitable. It is known that the stomach of small infants who have not eaten for a period of three hours is very acid, and that rotavirus is negatively affected by such an acidic pH. In our hands, when working with a low volume formulation, which is desirable, it has been impossible to measure the antacid capacity of classical phosphate-containing formulations, as phosphate solubility was easily exceeded and crystallization of the constituents occurred during formulation and/or short term storage. By contrast, the claimed compositions have surprisingly shown an acceptable but higher antacid capacity even in a smaller dose volume, compared to phosphate-containing prior art formulations.

In another specific embodiment, said liquid immunogenic composition is stable under at least one of the following conditions: for 7 days at 37° C., for one year at 4° C., for 18 months at 4° C., for two years at 4° C. According to the present invention, the stability of a given composition is assessed by measuring the viral titer (i.e. viral stability), according to the procedure set forth in example III.1, after storage of the formulation for a defined period of time at a given temperature. Stability of the composition may be assessed by an accelerated stability test, for example after storage of the formulation during one week at 37° C. The stability of the composition may alternatively be assessed over a longer period of time, such as during several months, either at refrigerator-temperature (between 2 and 7° C., typically at 4° C.) or at room temperature (20-22° C.). Under these conditions, a stable composition is that which has a maximum rotavirus titer loss of 1 as expressed in $\log_{10}$ ffu/dose in the defined test conditions. Particularly suitable compositions are those in which a maximum of 0.5 $\log_{10}$, for example 0.4 or less, 0.3 or less, 0.2 or less or suitably 0.1 $\log_{10}$ ffu per vaccine dose, is lost upon accelerated stability test at 37° C. during one week.

Alternatively, the liquid immunogenic composition as claimed herein may be frozen and stored frozen at −20° C. or below, or at −70° C. for several years, and remain stable at 4° C. for at least one year upon thawing. Typically the frozen formulation will be stable for at least 6 months, at least 12 months, at least 18 months, at least 2 years, or at least 3 years, and remain stable at 4° C. for at least one year, suitably 18 months or 2 years upon thawing.

The composition according to the present invention is an immunogenic composition, e.g. a vaccine. For example, the claimed immunogenic composition is capable, typically after one, suitably two doses separated by one or two months, to elicit an immune response e.g. excellent vaccine take and a serum rotavirus specific IgA responses. 'Vaccine take' is defined as the percentage of subjects displaying either a serological response, e.g. appearance of serum IgA to rotavirus in post-immunization sera at a titer $\geq$20 U/ml (ELISA), and/or with rotavirus shedding (ELISA) in any stool sample. Vaccine take can be defined as vaccine virus shedding in any stool sample collected between the first dose and up to 1 to 2 months after the second dose. In a specific embodiment, the vaccine according to the invention is capable of decreasing the occurrence of any, and preferably severe, rotavirus gastroenteritis as compared to placebo. Typically the vaccine is able to confer cross-protection against circulating strains other than that present in the vaccine. Typically, when the vaccine contains a G1 type strain such as that of the attenuated human virus P43, an immune response in induced to G1 and at least one of the non-G1 serotypes selected from the group consisting of: G2, G3, G4, G5, G6, G7, G8, G9, G10, G11, G12, G13 and G14 serotypes. Suitably a vaccine containing a G1 strain is capable of conferring protection against both G1 and non-G1 strains, such as G2, G3 and/or G4 strains, and in particular against the globally emerging G9 serotype.

In a specific embodiment, said gastroenteritis or severe gastroenteritis is caused by a rotavirus strain of a different serotype to that contained in the claimed composition. In particular, if the rotavirus strain present in the claimed composition is a G1 serotype, such as but not limited to the live attenuated human rotavirus strain HRV P43 (ECACC 99081301), prevention is conferred against gastroenteritis or severe gastroenteritis caused by a rotavirus strain of a G1 serotype and also by a rotavirus strain of a non-G1 serotype, for example by a rotavirus strain having a serotype selected from the list consisting of: G2, G3, G4, G5, G6, G7, G8, G9, G10, G11, G12, G13 and G14. In a particular embodiment, the immunogenic composition claimed herein is capable of inducing an immune response against, and/or provide protection against gastroenteritis or severe gastroenteritis caused by, at least one, suitably all of the following non-G1 serotypes: G2, G3, G4 and G9. In another specific embodiment, if the rotavirus strain present in the claimed composition is a P[8] rotavirus type, such as but not limited to the live attenuated human rotavirus strain HRV P43 (ECACC 99081301), prevention is conferred against gastroenteritis or severe gastroenteritis caused by a rotavirus strain of a P[8] type and by a non-P[8] type, for example by a rotavirus strain having a serotype selected from the list consisting of: P1, P2, P3, P4, P5, P6, P7, P9 and P11 types. In particular, the immunogenic composition claimed herein is capable of inducing an immune response against, and/or provide protection against gastroenteritis or severe gastroenteritis caused by, at least one, suitably all of the following non-P[8] type: P4, P6. In another embodiment, the claimed composition is capable of inducing an immune response to, and/or provide protection against gastroenteritis or severe gastroenteritis caused by, a rotavirus strain of a different G type and a different P type to that present in the administered composition. Specifically, the claimed composition comprises a G1P[8] rotavirus strain and is also capable of inducing an immune response to, and/or provide protection against gastroenteritis or severe gastroenteritis caused by, a G2P[4] rotavirus strain.

Suitably the composition according to the invention is administered by oral administration. Suitably the composition is supplied in a single-dose device, such as a glass or plastic vial or syringe, suitable for delivery to small infants.

Vaccines of the invention may be formulated and administered by known techniques, using a suitable amount of live virus to provide effective protection against rotavirus infection without significant adverse side effects in typical vaccines.

Accordingly the present invention provides a method for the preparation of a liquid rotavirus formulation or immunogenic composition as described herein comprising admixing a rotavirus antigen, a sugar and a carboxylate with a pharmaceutically acceptable diluent.

A suitable amount of live virus will normally be between $10^4$ and $10^7$ ffu per dose. A typical dose of vaccine may comprise $10^5$-$10^6$ ffu per dose and may be given in several doses over a period of time, for example in two doses given with a two-month interval. Rotavirus titer may also be expressed in CCID50 and it can be estimated in the context of this invention that a CCID50 of $10^{6.0}$ is equivalent to a ffu of $10^{5.5}$ per dose. Benefits may however be obtained by having more than 2 doses, for example a 3 or 4 dose regimen, particularly in developing countries. The first dose can suitably be given to infants at 4 weeks to 14 or 15 weeks of age, suitably between 6 and 14 weeks of age. The interval between doses is at least 4 weeks but may be more or less than two months long, for example the second dose, and any subsequent dose if appropriate, may be given one month or three months after the previous dose, depending on the local immunisation schedule. An optimal amount of live virus for a single dose or for a multiple dose regimen, and optimal timing for the doses, can be ascertained by standard studies involving observation of antibody titers and other responses in subjects.

Typically the volume of a dose of vaccine according to the invention will normally be 2.5 ml or lower, typically between 0.5 ml and 2.5 ml. In a specific aspect of the invention, a suitable vaccine dose will normally be 1.5 ml or suitably any volume smaller than 2.5 ml such as a volume of 2 ml or less, that is suitable for oral administration to babies or infants. In particular the dose volume will be such that the technical feasibility of the formulation is possible and there is no detrimental effect on the immunogenic potential of the formulation. The claimed compositions offer the advantage over prior art phosphate-containing formulations that they can withstand gastric acidity, remain immunogenic and stable over a long shelf-life, whilst being compatible with formulation in a dose volume smaller than usual, such as smaller than 2.0 ml or even, suitably, 1.5 ml or smaller. Typically the volume of a dose of vaccine according to the invention is between 0.5 ml and 2.0 ml, suitably approximately between 1.0 ml and 1.5 ml, such as approximately 1.3 ml or approximately 1.4 ml or approximately 1.5 ml. A typical dose volume may also be 2 ml or below, such as for example 1.1 ml, 1.2 ml, 1.3 ml, 1.4 ml or 1.5 ml. Volumes of 1 ml or volumes smaller than 1 ml, e.g. of between 200 µl to 800 µl, are also contemplated within the scope of the present invention. The volume of liquid that can be administered orally may also be partly determined by the vaccine delivery device.

The immunogenic composition of the invention may also be formulated to contain other antigens, in particular antigens from other suitable live viruses for protection against other diseases, for example poliovirus. Said additional active ingredients suitable for oral administration may be given either in admixture with the rotavirus composition, or alternatively may be co-administered (i.e. in a separate dose but on the same occasion) with the rotavirus composition claimed herein.

The claimed composition may also be given concomitantly with other non-oral vaccines, for example with parenteral vaccines suitable for the paediatric vaccine population such as DTPw or DTPa vaccines (vaccines against *Bordetella pertussis* —whooping cough, diphteria, tetanos), vaccines against *Haemophilus influenza* B-induced meningitis, hepatitis B, or measles, mumps, rubella (MMR), vaccines against *Streptococcus pneumoniae*, in order to optimise the number of visits to the doctor.

In another embodiment, the invention also provides a method of treating or preventing rotavirus associated diseases in humans, especially in young children such as babies or infants, by administering to said human subject in need thereof an effective amount of a liquid formulation, in particular an immunogenic composition or a vaccine, as claimed herein. In particular the claimed compositions will prevent from rotavirus infections. In a specific embodiment, the compositions claimed herein are capable of providing protection against rotavirus gastroenteritis, in particular against severe gastroenteritis. A severe gastroenteritis is defined as an episode requiring hospitalisation and/or re-hydration therapy (equivalent to WHO plan B or C) in a medical facility, or an episode with a score >11 on the 20-point Vesikari scale (Ruuska T and Vesikari T. Rotavirus disease in Finnish children: use of numerical scores for severity of diarrheal episodes. Scand J Infect Dis 1990, 22:259-67).

In a still further embodiment, the invention provides for the use of a rotavirus antigen, a carboxylate and a sugar in the manufacture of an immunogenic composition, e.g. a vaccine, for the treatment or prevention of rotavirus associated diseases in humans, wherein said immunogenic composition has a pH of between pH 5.0 and pH 8.0 and comprises less than 5 mM phosphate. In particular, prevention of rotavirus infections, and/or protection against gastroenteritis and more especially against severe gastroenteritis is especially contemplated.

In another specific embodiment, the invention also provides for the use of a human live attenuated rotavirus for the manufacture of an immunogenic composition as claimed herein for the treatment or prevention of rotavirus associated diseases without causing intussusception. In particular, said treatment or prevention comprises administering two oral doses, or more, of a safe and effective amount of the human live attenuated rotavirus composition to an infant within 4 to 14 or 15 weeks of age at the time of dose 1. Typically the infant will be from 6 to 14 weeks old at the time of the first dose. Within the context of the present invention a human infant is taken to mean an infant aged from 4 to 14 or 15 weeks of age after birth.

In another embodiment, the invention also provides for a liquid immunogenic composition comprising a rotavirus antigen, a sugar, phosphate and a carboxylate, wherein said composition has a pH of between about 5.0 to about 8.0 and wherein said carboxylate is selected from the list consisting of: adipate, malate, acetate, propionate, butyrate, malonate, glutarate, glycolate, gluconate, pimelate, and any combination of two or more thereof. In a specific embodiment said carboxylate is adipate. Typically phosphate will be present at a concentration of 10 mM to 1 M. The present inventor has found that these specific carboxylates, which have not been associated with the development of oral vaccine formulations, have fulfilled all the desired requirements of stability, acidic resistance, immunogenicity and formulation in a small dose volume, as set forth in the present description for the development of a suitable oral rotavirus vaccine for human infants. In particular said carboxylates have no detrimental effect on rotavirus titer in the formulation. These carboxylates can adequately act as alternatives for conventional carboxylates such as succinate, glutamate and citrate for example in phosphate-containing rotavirus formulations. All other specific embodiments as described hereinabove equally apply to this aspect of the present invention. Typically the pH range of the composition is as defined herein, as are the antacid capacity and shelf-life stability. The invention also provides for method of preparation of said composition, for uses and methods of prevention or treatment of human infants using said composition.

The invention will be further described by reference to the following, non-limiting, examples:

Example I

Formulation of a Live Attenuated Human Rotavirus Liquid Vaccine i) in the Absence of Added Phosphate and Carboxylate, and ii) in the Presence of Citrate as a Carboxylate in the Absence of Added Phosphate I.1. Preparation of the Formulations
I.1.1. Composition of the DMEM Medium (to Prepare 1 Litre of DMEM):
Water for injection: 0.8 liters
Dissolve Successively the Following Compounds:
Sodium chloride: 6.40 g
Potassium Chloride: 0.40 g
Magnesium Sulfate.7H2O: 0.20 g
Add iron nitrate solution at 0.1 g/L: 1.00 ml
$NaH_2PO_4.2H_2O$: 0.1412 g
Sodium pyruvate: 0.11 g
Glucose anhydre: 4.50 g
Vitamin solution (500× concentrated): 2.00 ml
Water for injection: 1.50 ml
Chlorhydric acid (concentrated): 0.083 ml
L-Cystine: 0.048 g
L-Tyrosine: 0.072 g
Water for injection: 2.00 ml
Aminoacids solution: 20.00 ml L-Glutamine: 0.5846
Calcium chloride.2H2O: 0.2649 g
Sodium bicarbonate: 3.70 g
Water for injection up to 1 liter DMEM represents 5%, 6% or 8% of the formulations detailed in Example II. This corresponds to:
  a final phosphate concentration of 0.059 mM, 0.071 mM and 0.094 mM respectively, and
  a final pyruvate concentration of 0.065 mM, 0.078 mM and 0.104 mM respectively.

Vitamin Solution (500× Concentrated):
Water for injection: 80.00 L
Folic acid: 200.10 g
Calcium panthenoate: 200.10 g
Choline chloride: 200.10 g
Inositol: 350.00 g
Nicotinamide: 200.00 g
Pyridoxine Chlorhydrate: 200.10 g
Thiamine chlorhydrate: 200.10 g
Riboflavine: 20.002 g
Water for injection up to 100 liters.

Aminoacid Solution:
Water for injection: 144.00 L
L-Arginine: 755.70 g
Glycine: 270.10 g
L-Histidine: 378.00 g
L-Isoleucine: 943.40 g
L-Leucine: 943.50 g
L-Lysine 2HCl: 1,315.80 g
L-Methionine: 270.00 g
L-Phenylalanine: 594.10 g
L-Threonine: 856.30 g
L-Tryptophane: 144.00 g
L-Serine: 377.90 g
L-Valine: 842.00 g
Water for injection: up to 180 Liters.

Iron Nitrate Solution
Water for injection: 1,035.000 ml
Iron nitrate.9H2O: 0.115 g
Water for injection: up to 1.150 liters I.1.2. Preparation of the Rotavirus Formulations in the Absence of Added Phosphate and Carboxylate Formulation 60 presented in Table 2 has been made at 325 g (250 ml) total scale, representing 166.6 doses of 1.5 ml (1.95 g) each.

Formulation no 60: to 143 g water (quantity determined so as to reach a final 325 g preparation) is added: 162.5 g of sucrose (50% w/w). After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose volume is 1.5 ml. The mix is homogenized and distributed in the appropriate dose container. In this example DMEM represent 6% w/w.

Results of the antacid capacity, initial viral titer and viral stability are shown in Tables 2 to 4.

TABLE 2

| 1.5 ml dose volume | | | | | | | |
|---|---|---|---|---|---|---|---|
| N° | Sucrose % w/w | DMEM % w/w | BRR* pH at t = 0 | BRR* time at pH > 4 (min) | Viral Titer at t = 0 (log$_{10}$ ffu per vaccine dose) | Viral titer after 1 w 37° C. | Viral loss after 1 w 37° C. |
| 60 | 50.0% | 6% | 7.82 | <1 | 6.3 | 5.4 | 0.9 |

*assessed by the Baby Rossett Rice (BRR) test as adapted according to Example III.2.2

TABLE 3

| 1.5 ml dose volume - Viral stability at room temperature | | | | | | | | | | |
|---|---|---|---|---|---|---|---|---|---|---|
| | Viral titration after storage at room temperature (log$_{10}$ ffu per vaccine dose) | | | | | | | | | |
| n° | 1 m* | 2 m* | 3 m* | 4 m* | 5 m* | 6 m* | 7 m* | 8 m* | 9 m* | 10 m* |
| 60 | 5.6 | 5.6 | 5.0 | ND | ND | ND | ND | ND | ND | ND |

*= month(s);
ND = not determined

TABLE 4

| 1.5 ml dose volume - Viral stability at 4° C. | | | | | | | | |
|---|---|---|---|---|---|---|---|---|
| | Viral titration after storage at 4° C. (log$_{10}$ ffu per vaccine dose) | | | | | | | |
| n° | T = 0 | after 1 w 37° C. | 1 m* 4° C. | 2 m* 4° C. | 4 m* 4° C. | 6 m* 4° C. | 9 m* 4° C. | 12 m* 4° C. |
| 60 | 6.3 | 5.4 | 6.2 | 5.8 | 6.0 | 5.5 | ND | ND |

*= month(s);
ND = not determined

I.1.3. Preparation of the Rotavirus Formulations Containing a Carboxylate

Citric acid (when present) and citrate salt are admixed in the proportions and conditions illustrated in Tables 5 and 6. Rotavirus stability and antacid capacity of the formulations are measured according to the methods given in Examples III.1 and III.2, respectively.

Formulations 110-115 and 128-130 were prepared. The volume of dose was 2.5 ml for formulations 110-115 and 1.5 ml for formulations 128-130. Formulations 110-115 presented in Table 5 have been made at 325 g (250 ml) total scale, representing 100 doses of 2.5 ml (3.25 g) each.

Formulation 110 was prepared as follows. To 123.71 g of water (quantity determined so as to reach a final 325 g preparation) are consecutively added: 19.29 g tri-sodium citrate ($Na_3Citrate.2H_2O$, Mw 294) (corresponding to a final concentration of 262 mM) and 162.50 g sucrose (50% w/w). After complete dissolution the solution is sterilised by filtration on a 0.2 μm membrane. Under sterile conditions 19.5 g of DMEM medium, containing the necessary quantity of rotavirus to obtain $10^{6.0}$ ffu per dose, is added. In this case the single dose volume is 2.5 ml or 3.25 g. The mix is homogenised and distributed in the appropriate dose container.

In this example DMEM medium represents 6% w/w, corresponding to a final phosphate concentration of 0.059 mM.

Formulations 111-115 are prepared according to a procedure similar to that explained in respect of formulation 110, except that the amount of ingredients is adapted as detailed in Table 5. For example, formulation 111 was prepared by mixing the following ingredients: 123.73 g of water (quantity determined so as to reach a final 325 g preparation), 19.07 g tri-sodium citrate ($Na_3Citrate.2H_2O$, Mw 294) (corresponding to a final concentration of 259 mM), 0.197 g citric acid (Mw 192) (corresponding to a final concentration of 4 mM) and 162.50 g sucrose (50% w/w). The rest of the procedure was done as for formulation 110.

Results of the antacid capacity, initial viral titer and viral stability are shown in Tables 5 to 8.

TABLE 5

2.5 ml dose volume

| N° | Citric Acid (M) | Na3 Citrate•2H$_2$O (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | (log$_{10}$ ffu per vaccine dose) | | |
| 110 | 0 | 0.262 | 50% | 6% | 8.15 | 14 | 5.7 | 4.8 | 0.9 |
| 111 | 0.004 | 0.259 | 50% | 6% | 6.95 | 14 | 5.3 | 5.4 | 0 |
| 112 | 0.010 | 0.256 | 50% | 6% | 6.51 | 12-13 | 5.6 | 5.6 | 0 |
| 113 | 0.014 | 0.249 | 50% | 6% | 6.34 | 12 | 5.6 | 5.4 | 0.2 |
| 114 | 0.034 | 0.283 | 50% | 6% | 5.94 | 12-13 | 5.6 | 5.3 | 0.3 |
| 115 | 0.093 | 0.333 | 50% | 6% | 5.37 | 14 | 5.7 | 5.6 | 0.1 |

*assessed by the Baby Rossett Rice (BRR) test as adapted according to Example III.2.2

Formulations presented in Table 6 have been made at 325 g (250 ml) total scale, representing 166.6 doses of 1.5 ml (1.95 g) each. Antacid materials: Citric Acid.1H2O (Mw 210), Na$_3$Citrate.2H$_2$O (Mw 294).

Formulation 128 has been prepared by mixing 110.89 g of water (quantity determined so as to reach a final 325 g preparation) with the following ingredients: 31.78 g tri-sodium citrate (Na$_3$Citrate.2H$_2$O, Mw 294) (corresponding to a final concentration of 432 mM), 0.328 g citric acid (Citric Acid.1H$_2$O, Mw 210) (corresponding to a final concentration of 6 mM) and 162.50 g sucrose (50% w/w). After complete dissolution the solution is sterilised by filtration on a 0.2 µm membrane.

Under sterile conditions 19.5 g of DMEM medium containing the necessary quantity of rotavirus to obtain $10^{6.0}$ ffu per dose is added. In this case the dose is 1.5 ml or 1.95 g. The mix is homogenised and distributed in the appropriate dose container. In this example DMEM medium represents 6% w/w, corresponding to a final phosphate concentration of 0.059 mM.

Formulations 129 and 130 have been prepared similarly to the procedure described for formulation 128 whilst adapting the amounts of ingredients according to Table 6. Briefly, formulation 129 has been prepared by mixing 0.77 g citric acid (Citric Acid.1H$_2$O, Mw 210) (corresponding to a final concentration of 15 mM) and 31.36 g tri-sodium citrate (Na$_3$Citrate.2H$_2$O (Mw 294) corresponding to a final concentration of 426 mM). Formulation 130 has been prepared by mixing 2.75 g citric acid (Citric Acid.1H$_2$O, Mw 210) (corresponding to a final concentration of 52 mM) and 34.7 g tri-sodium citrate (Na$_3$Citrate.2H$_2$O (Mw 294) corresponding to a final concentration of 472 mM). The rest of the ingredients and proportions are in Table 6.

TABLE 7

1.5 ml dose volume - Viral stability at room temperature

Viral titration after storage at room temperature (log$_{10}$ ffu per vaccine dose)

| n° | 1 m* | 2 m* | 3 m* | 4 m* | 5 m* | 6 m* | 7 m* | 8 m* | 9 m* | 10 m* |
|---|---|---|---|---|---|---|---|---|---|---|
| 128 | ND | ND | ND | ND | 5.4 | 5.1 | ND | ND | ND | ND |
| 129 | ND | ND | ND | ND | 5.4 | 5.0 | ND | ND | ND | ND |
| 130 | ND | ND | ND | ND | 5.6 | 5.0 | ND | ND | ND | ND |

* = month(s);
ND = not determined

TABLE 8

1.5 ml dose volume - Viral stability at 4° C.

Viral titration after storage at 4° C. (log$_{10}$ ffu per vaccine dose)

| n° | T = 0 | after 1 w 37° C. | 1 m* 4° C. | 2 m* 4° C. | 4 m* 4° C. | 6 m* 4° C. | 9 m* 4° C. | 12 m* 4° C. |
|---|---|---|---|---|---|---|---|---|
| 128 | 6.1 | 5.8 | ND | ND | ND | 5.8 | ND | 5.7 |
| 129 | 5.9 | 5.8 | ND | ND | ND | 5.8 | ND | 5.6 |
| 130 | 5.9 | 5.8 | ND | ND | ND | 5.9 | ND | 5.4 |

* = month(s);
ND = not determined

I.2 Rotavirus Stability and Antacid Capacity—Results

Rotavirus viral titration at different points in time has been evaluated according to the procedure given in Example III.1 and the antacid capacity of the formulation has been evaluated following the protocol given in Example III.2. The results are illustrated in Tables 2 to 8.

The pH for the control formulation 60, which was devoid of carboxylate and added phosphate, had no antacid capacity and further exhibited a pH close to the upper limit of pH 8.0 for virus stability.

TABLE 6

1.5 ml dose volume

| N° | Citric Acid•1H$_2$O (M) | Na3 Citrate•2H$_2$O (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | (log$_{10}$ ffu per vaccine dose) | | |
| 128 | 0.006 | 0.432 | 50.0% | 6% | 6.97 | 13 | 6.1 | 5.8 | 0.3 |
| 129 | 0.015 | 0.426 | 50.0% | 6% | 6.55 | 12 | 5.9 | 5.8 | 0.1 |
| 130 | 0.052 | 0.472 | 50.0% | 6% | 5.92 | 13 | 5.9 | 5.8 | 0.1 |

*assessed by the Baby Rossett Rice (BRR) test as adapted according to Example III.2.2

For all experimental formulations tested in Tables 5 to 8, the pH was maintained in a range of about 5.0-7.0 except for formulation 110, which exhibited a pH of above 8.0. As can be seen from the viral titer and viral loss results, the rotavirus stability in the liquid formulation is related to the pH of this formulation. In the range of about pH 5.4 (i.e. formulation 115) to pH 7.0 (i.e. formulations 111 and 128), the viral loss after 7 days at 37° C. was kept at a low level (i.e. below 0.5 log), and this contrasted with the result obtained for formulation 110 (pH>8, with a viral titer loss of 0.9 log).

In addition, formulations 111-115 and 128-130, they showed a similar antacid capacity to that of formulation 110, as assessed by the Baby Rossett-Rice assay (see Example III.2.2). This antacid capacity well exceeded the lower limit of 8 min for 2.5 ml as well as for 1.5 ml dose volume formulations, and actually reached a minimum of 12 minutes, and was considered therefore highly satisfactory.

Alternative carboxylates have also been tested as these may represent technically feasible alternatives when relatively low amounts of carboxylates may be desirable, for example when working with very small dose volumes.

Examples of formulations containing such alternative carboxylates are given in Example II and Tables 10-39.

Example II

Formulations with an Alternative Carboxylate Salt in the Absence of Added Phosphate The following carboxylate salts have been used to create a buffer capacity: acetate, malonate, succinate, glutarate, adipate and malate. According to the $pK_a$ of a given carboxylic acid, and depending on its molecular weight, it is possible to find quantities to be formulated to achieve the target antacid capacity of at least 8 minutes, suitably at least 12 minutes as assessed by the BRR test, whilst being in a pH window of between pH 5.0 to pH 8.0.

Chemically speaking, a "buffer" effect is obtained when mixing a strong acid (like HCl) and a salt derived from a weak acid (like sodium acetate). The pH value corresponding to the middle of the buffer plateau is equal to the $pK_a$ of the weak acid. The $pK_a$ of carboxylic acid is a measure of acidic strength, in other words an indicator of the effective buffering range of the compound.

Since rotavirus is rapidly degraded below pH 4 (C. Weiss and H. F. Clark, 1985 J. Gen. Virol., 66, 2725-2730), a buffer plateau of above pH 4 is desirable, i.e. suitably carboxylates with $pK_a$>4 or di-carboxylates with an average $pK_a$>4. Suitable carboxylates are given in Table 9. Numerical average $pK_a$ values are given.

TABLE 9 characteristics of various carboxylates

| Carboxylic acids | MW | $pK_{a1}$ | $pK_{a2}$ | $pK_{a3}$ | Av. $pK_a$ | Toxicity (LD50 oral, in rat) |
|---|---|---|---|---|---|---|
| Citric* | 192 | 6.39 | 4.76 | 3.13 | 4.76 | 3.0 g/kg |
| Other carboxylic acids with $pK_a$ > 4 | | | | | | |
| Propinic* | 74 | 4.88 | | | | 2.6 g/kg |
| Butyric | 88 | 4.82 | | | | |
| Acetic* | 60 | 4.76 | | | | 3.3 g/kg |
| Dicarboxylic acids with an average $pK_a$ > 4 | | | | | | |
| Maleic | 116 | 6.23 | 1.92 | | 4.07 | |
| Malonic | 104 | 5.7 | 2.83 | | 4.26 | 1.31 g/kg |

TABLE 9-continued characteristics of various carboxylates

| Carboxylic acids | MW | $pK_{a1}$ | $pK_{a2}$ | $pK_{a3}$ | Av. $pK_a$ | Toxicity (LD50 oral, in rat) |
|---|---|---|---|---|---|---|
| Succinic | 118 | 5.6 | 4.21 | | 4.90 | 2.26 g/kg |
| Adipic* | 146 | 5.4 | 4.43 | | 4.91 | 5.7 g/kg |
| Glutaric | 132 | 5.22 | 4.34 | | 4.78 | |
| Malic* | 134 | 5.05 | 3.40 | | 4.22 | 1.6 g/kg |

*Five carboxylic acids have the "food additive" status: Citric E330, Acetic E260, Propionic E280, Malic E296 and Adipic E355.

A standard acid-base titration curve for four carboxylates (sodium malate, sodium acetate, sodium citrate and sodium adipate) is illustrated in FIG. 1. It shows that the useful antacid capacity between pH 4.0 and pH 7.0 for example, is of 72.50%, 68.75%, 57.70% and 41.25% for sodium adipate, sodium acetate, sodium citrate and sodium malate, respectively.

Formulations have been prepared with the following carboxylates: acetate, malonate, succinate, glutarate, adipate and malate. All formulations shown in this Example have been prepared in a 1.5 ml dose volume.

II.1. Formulations with Acetate

II.1.1. Formulations presented in Table 10 have been made at 325 g scale (250 ml) representing 166.6 doses of 1.5 ml (1.95 g) each. Antacid materials: Acetic acid (Mw 60), NaOH (Mw 40).

Formulation 36: to 148.84 g of water (quantity sufficient to reach a final 325 g preparation) are successively added: 10.66 g NaOH, glacial acetic acid up to pH 7.16 and 130 g of sucrose (40% w/w). After complete dissolution the solution is sterilized by filtration on a 0.2 µm membrane. Under sterile conditions 19.5 g of DMEM medium containing the necessary quantity of rotavirus is added to the solution, to obtain $10^{6.0}$ ffu per dose. In this case the dose is 1.5 ml or 1.95 g. The mixture is homogenized and distributed in the appropriate dose container. In this example DMEM represent 6% w/w.

Formulations 37 and 42: it is proceeded as for formulation 36 but the quantities are adjusted according to Table 10.

Formulation 87: to 75.00 g of water are successively added: 8.00 g NaOH, 15.00 g glacial acetic acid, enough 1N NaOH solution to reach a pH of 7.00 (in this case 2 g of 1N NaOH was added), additional water to reach the sufficient quantity of 325 g (in this case 43.00 g of water was added), and 162.50 g of sucrose (50% w/w). The rest of the procedure is performed as for formulation 36.

Example for formulations 88-90: it was proceeded as for formulation no 87 except that the amounts are adapted as mentioned in Table 10.

Example for formulations 33-35: it was proceeded as for formulation no 36 except that the amounts are adapted as mentioned in Table 10 and that NaOH is replaced by Ca(OH)$_2$. Formulations 33-35 were not included in the low term stability study due for failing to comply with the stability test of 1 week at 37° C. Satisfactory results in the presence of additional calcium ion are nonetheless presented in the adipate series (see Example II.5.4, and Table 26).

TABLE 10

| N° | Acetic acid (M) | Sucrose % w/w | DMEM % w/w | BRR* pH at t = 0 | BRR* time at pH > 4 (min) | Viral Titer at t = 0 (log₁₀ ffu per vaccine dose) | Viral titer after 1 w 37° C. (log₁₀ ffu per vaccine dose) | Viral loss after 1 w 37° C. (log₁₀ ffu per vaccine dose) |
|---|---|---|---|---|---|---|---|---|
| NaOH (M) | | | | | | | | |
| 36 | 1.07 | up to pH 7.16 | 40% | 6% | 7.2/ 7.23° | 13/14° | 5.8 | 5.3 | 0.5 |
| 37 | 1.07 | up pH 7.55 | 50% | 6% | 7.62/ 7.63° | 13/15° | 5.8 | 5.4 | 0.4 |
| 42 | 1.05 | up pH 7.7 | 50% | 6% | 8.06/ 8.03° | 15/16° | 5.9 | 5.1 | 0.8 |
| 87 | up pH 7.0 | 1 | 50% | 6% | 7.24 | 13 | 6.2 | 6.1 | 0.1 |
| 88 | up pH 6.5 | 1 | 50% | 6% | 6.7 | 13 | 5.8 | 5.9 | 0 |
| 89 | up pH 6.0 | 1 | 50% | 6% | 6.14 | 12 | 5.9 | 5.5 | 0.4 |
| 90 | up pH 6.0 | 1 | 55% | 6% | 6.10 | 13 | 6.0 | 5.5 | 0.5 |
| Ca(OH)₂ | | | | | | | | |
| 33 | 0.540 | up to pH 7.32 | 40% | 6% | 7.66 | 12 | 5.8 | 4.3 | >1 |
| 34 | 0.540 | up to pH 7.55 | 45% | 6% | 8.09 | 13 | 5.9 | <3.8 | >1 |
| 35 | 0.540 | up to pH 7.35 | 50% | 6% | 7.76 | 13 | 6.3 | <3.8 | >1 |

*assessed by the Baby Rossett Rice (BRR) test as adapted according to Example III.2.2;
°= repeats II.1.2. Formulations presented in Table 11 have been made at 325 g scale (250 ml) representing 166.6 doses of 1.5 ml (1.95 g) each. Antacid materials: Sodium acetate.3H2O (Mw 136).

Example for formulation 58: to 113.00 g water (quantity determined so as to reach a final 325 g preparation) are successively added: 30.00 g sodium acetate 3H2O and 162.50 g sucrose (50% w/w). After complete dissolution the solution is sterilized by filtration on a 0.2 μm membrane. Under sterile conditions 19.5 g of DMEM medium containing the necessary quantity of rotavirus is added to the solution, to obtain $10^{6.0}$ ffu per dose. In this case the dose is 1.5 ml or 1.95 g. The mixture is homogenized and distributed in the appropriate dose container. In this example DMEM represent 6% w/w.

Formulations 59, 66, 69, and 70: It is proceeded similarly to formulation 58 with adjusted amounts (see Table 11).

TABLE 11

| N° | Na Acetate• 3H2O (M) | Sucrose % w/w | DMEM % w/w | BRR* pH at t = 0 | BRR* time at pH > 4 (min) | Viral Titer at t = 0 (log₁₀ ffu per vaccine dose) | Viral titer after 1 w 37° C. (log₁₀ ffu per vaccine dose) | Viral loss after 1 w 37° C. (log₁₀ ffu per vaccine dose) |
|---|---|---|---|---|---|---|---|---|
| 58 | 0.882 | 50% | 6% | 7.98 | 11 | 6.3 | 5.6 | 0.7 |
| 59 | 0.706 | 50% | 6% | 7.94 | 7 | 6.2 | 5.4 | 0.8 |
| 66 | 0.941 | 54% | 6% | 8.13/ 8.14° | 13 | 5.9 | 5.3 | 0.6 |
| 69 | 0.753 | 55% | 6% | 8.15 | 8 | 6.0 | 5.3 | 0.7 |
| 70 | 1.338 | 50% | 6% | 8.23 | 20 | 6.0 | 5.4 | 0.6 |

*as assessed by the Baby Rossett Rice (BRR) test as adapted according to Example III.2.2.;
°= repeat II.1.3. Rotavirus Stability and Antacid Capacity—Results Rotavirus viral titration at different points in time has been evaluated according to the procedure given in Example III.1 and the antacid capacity of the formulation has been evaluated following the protocol given in Example III.2.2. The results are illustrated in Tables 10, 11, 12 and 13.

In conclusion, the rotavirus stability in a liquid acetate formulation is related to the pH. A suitable working range is between pH 6.0 to 7.5.

TABLE 12

Viral stability at room temperature

Viral titration after storage at room temperature ($\log_{10}$ ffu per vaccine dose)

| n° | 1 m* | 2 m* | 3 m* | 4 m* | 5 m* | 6 m* | 7 m* | 8 m* | 9 m* | 10 m* |
|---|---|---|---|---|---|---|---|---|---|---|
| 36 | 5.8 | 5.2 | 4.7 | | | | | | | |
| 37 | 5.8 | 5.5 | 5.3 | 5.0 | 5.0 | 4.4 | | | | |
| 42 | 5.2 | 5.4 | 5.1 | | | | | | | |
| 87 | | 6.0 | 5.9 | | | 5.6 | | 5.3 | 5.3 | 4.7 |
| 88 | | 5.9 | 5.6 | | | | | | | |
| 89 | | 5.2 | 4.7 | | | | | | | |
| 90 | | 4.8 | 4.6 | | | | | | | |
| 58 | 5.6 | 5.4 | 4.9 | | | | | | | |
| 59 | 5.7 | 5.5 | 4.9 | | | | | | | |
| 66 | 5.8 | 5.4 | 5.5 | | | | | | | |
| 69 | 5.9 | 5.5 | 5.5 | | | | | | | |
| 70 | 5.9 | 5.5 | 5.4 | | | | | | | |

*= month(s);
Blank boxes = criteria not determined

TABLE 13

Viral stability at 4° C.

Viral titration after storage at 4° C. ($\log_{10}$ ffu per vaccine dose)

| n° | T = 0 | after 1 w 37° C. | 1 m* 4° C. | 2 m* 4° C. | 4 m* 4° C. | 6 m* 4° C. | 9 m* 4° C. | 12 m* 4° C. | 15 m* 4° C. |
|---|---|---|---|---|---|---|---|---|---|
| 36 | 5.8 | 5.3 | 5.8 | 5.8 | 5.6 | | | | |
| 37 | 5.8 | 5.4 | 5.9 | 5.8 | 5.8 | 5.7 | | | |
| 42 | 5.9 | 5.1 | 5.9 | 5.7 | 5.7 | | | | |
| 87 | 6.2 | 6.1 | | 6.3 | | 6.1 | | | 6.1 |
| 88 | 5.8 | 6.0 | | 6.0 | | | | | |
| 89 | 5.9 | 5.5 | | 5.8 | | | | | |
| 90 | 6.0 | 5.5 | | 5.7 | | | | | |
| 58 | 6.3 | 5.6 | 6.2 | 5.8 | 6.0 | | | | |
| 59 | 6.2 | 5.4 | 6.2 | 5.7 | 6.0 | | | | |
| 66 | 5.9 | 5.3 | 5.9 | 5.8 | | | | | |
| 69 | 6.0 | 5.3 | 6.0 | 5.9 | | | | | |
| 70 | 6.0 | 5.4 | 6.0 | 5.9 | | | | | |

*= month(s);
Blank boxes = criteria not determined

II.2. Formulations with Malonate

II.2.1. Formulation 67 (see Table 14) has been made at 325 g total scale (250 ml) representing 166.6 doses of 1.5 ml (1.95 g) each. Antacid materials: Malonic acid (Mw 104), NaOH (Mw 40).

Formulation 54 (see Table 14) has been made at 44 g total scale (35 ml) representing 20 doses of 1.75 ml (2.2 g) each. Antacid materials: Malonic acid (Mw 104), NaOH (Mw 40).

Formulation no 67: to 110.70 g water (quantity determined so as to reach a final 325 g preparation) are successively added: 14.00 g NaOH, 18.230 g malonic acid and 162.5 g of sucrose (50% w/w). After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The mix is homogenized and distributed in the appropriate dose container. In this example DMEM represent 6% w/w.

Formulation no 54: to 16.64 g water (quantity determined so as to reach a final 44 g preparation) are successively added: 2.4 g NaOH, 3.1213 g malonic acid and 19.5 g of sucrose (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mix is homogenized and distributed in the appropriate dose container. In this example DMEM represent 6% w/w.

TABLE 14

| N° | NaOH (M) | Malonic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 67 | 1.4 | 0.701 | 50% | 6% | 6.53 | 11-12 | 6.0 | 5.7 | 0.3 |
| 54 | 1.71 | 0.857 | 44% | 6% | 8.36 | 23 | °° | °° | °° |

*assessed by the Baby Rossett Rice (BRR) test as adapted according to Example III.2.2.
°° Formulation 54 was discarded from the long term stability study because of its initial pH of above 8.0

II.2.2. The formulation presented in Table 15 has been made at 325 g total scale (250 ml) representing 147.7 doses of 1.75 ml (2.20 g) each. Antacid material: disodium malonate (Mw 148).

Formulation no 62: to 138.50 g water (quantity determined so as to reach a final 325 g preparation) are successively added: 23.00 g disodium malonate and 144.00 g of sucrose (44% w/w). After complete dissolution the solution is sterilized by filtration on a 0.2 μm membrane. Under sterile conditions 19.5 g of DMEM medium containing the necessary quantity of rotavirus is added to the solution, to obtain $10^{6.0}$ ffu per dose. In this case the dose is 1.75 ml or 2.20 g. The mixture is homogenized and distributed in the appropriate dose container. In this example DMEM represent 6% w/w.

TABLE 15

| N° | Na Malonate (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|
| | | | | | | ($\log_{10}$ ffu per vaccine dose) | | |
| 62 | 0.601 | 44% | 6% | 8.21 | 12 | 6.1 | 5.0 | 0.9 |

*assessed by the Baby Rossett Rice (BRR) test as adapted according to Example III.2.2.

II.2.3. Rotavirus Stability and Antacid Capacity—Results

In conclusion, the rotavirus stability in a liquid malonate formulation is related to the pH: pH 6.5 gives a good stability during 1 week at 37° C. while more than 0.9 log of loss is observed at pH 8.2.

II.3 Formulations with Succinate

II.3.1. Formulation 127 (see Table 16) has been made at 325 g scale (250 ml) representing 166.6 doses of 1.5 ml (1.95 g) each. Antacid materials: Succinic acid (Mw 118), NaOH (Mw 40).

Formulation 51 (see Table 16) has been made at 44 g scale (35 ml) representing 20 doses of 1.75 ml (2.2 g) each. Antacid materials: Succinic acid (Mw 118), NaOH (Mw 40).

Formulation 127: to 120.16 g water (quantity determined so as to reach a final 325 g preparation) are successively added: 9.10 g NaOH, 13.74 g succinic acid and 162.5 g of sucrose (50% w/w). The rest of the formulation steps are identical to those described for formulation 67. In this example DMEM represent 6% w/w.

Formulation 51: to 16.22 g water (quantity determined so as to reach a final 44 g preparation) are successively added: 2.4 g NaOH, 3.5414 g succinic acid and 19.5 g of sucrose (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mix is homogenized and distributed in the appropriate dose container. In this example DMEM represent 6% w/w.

TABLE 16

| N° | NaOH (M) | Succinic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 127 | 0.91 | 0.466 | 50% | 6% | 6.33 | 9 | 5.9 | 5.7 | 0.2 |
| 51 | 1.71 | 0.857 | 44% | 6% | 7.20 | >29 | ∞∞ | ∞∞ | ∞∞ |

*assessed by the Baby Rossett Rice (BRR) test as adapted according to Example III.2.2.
∞∞ Formulation 51 was discarded from the long term stability study as its antacid capacity was determined to be too long II.3.2. Formulation 56 is presented in Table 17 and has been made at 325 g total scale (250 ml) representing 166.6 doses of 1.5 ml (1.95 g) each. Antacid materials: Disodium succinate (Mw 162).

Formulation 56: To 122.50 g water (quantity determined so as to reach a final 325 g preparation) are successively added: 20.50 g disodium succinate and 162.50 g of sucrose (50% w/w). The rest of the formulation steps are identical to those described for formulation 62. In this example DMEM represent 6% w/w.

To 15.8 g water (quantity determined so as to reach a final 44 g preparation) are successively added: 2.4 g NaOH, 3.964 g glutaric acid and 19.5 g of sucrose. (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mix is homogenized and distributed in the appropriate dose container. In this example DMEM represent 6% w/w.

TABLE 17

| N° | Di-sodium succinate (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|
|   |   |   |   |   |   | ($\log_{10}$ ffu per vaccine dose) | | |
| 56 | 0.506 | 50% | 6% | 8.12/ 8.30° | 13 | 6.3 | 5.5 | 0.8 |

*assessed by the Baby Rossett Rice (BRR) test as adapted according to Example III.2.2.;
°= repeat II.3.3. Rotavirus Stability and Antacid Capacity—Results In conclusion, the rotavirus stability in a liquid succinate formulation is related to the pH: pH 6.3 gives good stability during 1 week at 37° C. while 0.8 log of loss is observed at pH 8.1.

II.4. Formulations with Glutarate

II.4.1. Formulations with glutarate are presented in Table 18.

Formulation 65 has been made at 320.8 g total scale (246 ml) representing 164 doses of 1.5 ml (1.95 g) each. Antacid materials: Glutaric acid (Mw 132), NaOH (Mw 40).

Formulations 125 and 126 have been made at 325 g total scale (250 ml) representing 166.6 doses of 1.5 ml (1.95 g) each. Antacid materials: Glutaric acid (Mw 132), NaOH (Mw 40).

Formulation 125: to 100.35 g water (quantity determined so as to reach a final 325 g preparation) are successively added: 9.10 g NaOH, 15.40 g glutaric acid and 162.5 g of sucrose. The rest of the formulation steps are identical to those described for formulation 67. In this example DMEM represent 6% w/w.

Formulation 126: it was proceeded as for formulation 125 but with adjusted amounts (see Table 18).

TABLE 18

| N° | NaOH (M) | Glutaric acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
|   |   |   |   |   |   |   | ($\log_{10}$ ffu per vaccine dose) | | |
| 125 | 0.910 | 0.467 | 50% | 6% | 6.17 | 10-11 | 5.8 | 5.7 | 0.1 |
| 65 | 0.945 | 0.474 | 50.6% | 6% | 6.49 | 11 | 6.0 | 5.6 | 0.4 |
| 126 | 0.950 | 0.467 | 50% | 6% | 8.13 | 12 | 6.1 | 5.4 | 0.7 |
| 50 | 1.71 | 0.858 | 44% | 6% | 8.45 | >29 | °° | °° | °° |

*assessed by the Baby Rossett Rice (BRR) test as adapted according to Example III.2.2.
°° Formulation 50 was discarded from the long term stability study because of its initial pH (above 8.0) and its antacid capacity (determined to be too long)

To 114.1 g water (quantity determined so as to reach a final 320.8 g preparation) are successively added: 9.3 g NaOH, 15.40 g glutaric acid and 162.5 g of sucrose. (50.6% w/w). After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The mix is homogenized and distributed in the appropriate dose container. In this example DMEM represent 6.08% w/w.

Formulation 50 has been made at 44 g total scale (35 ml) representing 20 doses of 1.75 ml (2.2 g) each. Antacid materials: Glutaric acid (Mw 132), NaOH (Mw 40).

II.4.2. Rotavirus Stability and Antacid Capacity—Results

In conclusion, the rotavirus stability in a liquid glutarate formulation is related to the pH: pH 6.17 gives good stability during 1 week at 37° C. while 0.7 log of loss is observed at pH 8.1.

II.5. Formulations with Adipate

II.5.1. Adipate-containing formulations presented in Table 19 have been made at the 325 g scale (250 ml) representing 166.6 doses of 1.5 ml (1.95 g) each excepted formulation no 45 which has been prepared at the 44 g scale (35 ml) representing 20 doses of 1.75 ml (2.2 g) each, and no 63 which has been prepared at the 320.8 g scale (247 ml) representing 164 doses of 1.5 ml (1.95 g) each. Antacid materials: Adipic acid (Mw 146), NaOH (Mw 40).

Formulation 45: to 15.38 g water (quantity determined so as to reach a final 44 g preparation) are successively added: 2.4 g NaOH, 4.3809 g adipic acid and 19.5 g of sucrose (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

Formulation 63: to 112.50 g water (quantity determined so as to reach a final 320.8 g preparation) are successively added: 9.3 g NaOH, 17.00 g adipic acid and 162.5 g of sucrose. After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The mixture is homogenized and distributed in the appropriate dose container. In this example DMEM represent 6.08% w/w.

Formulation 81: to 116.70 g water (quantity determined so as to reach a final 325 g preparation) are successively added: 9.28 g NaOH, 17.00 g adipic acid and 162.5 g of sucrose (50% w/w). The rest of the formulation steps are identical to those described for formulation 67. In this example DMEM represent 6% w/w.

Formulations 82, 83, 91-97, 100-109, 122-124, 131-134, 136-145, 147, 148: To water (quantity determined so as to reach a final 325 g preparation) are successively added: NaOH, adipic acid and sucrose in quantities as described in Tables 19 and 23. After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The resulting mixture is homogenized and distributed in the appropriate dose container. In this example DMEM represent 6% w/w.

Several parameters, shown in bold in Table 19, have been varied to test the performance of the resulting formulations with respect to antacid capacity and virus stability.

TABLE 19

| N° | NaOH (M) | Adipic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 45 | 1.71 | 0.857 | 44% | 6% | 7.29 | >29 | | °° | |
| | | | | | Effect of sugar % | | | | |
| 63 | 0.945 | 0.472 | 50.6% | 6% | 6.49 | 12 | 6.0 | 5.6 | 0.4 |
| 81 | 0.917 | 0.460 | 50% | 6% | 6.2 | 11-12 | 5.9 | 5.7 | 0.2 |
| 82 | 0.899 | 0.451 | 45% | 6% | 6.39 | 11-12 | 5.9 | 5.7 | 0.2 |
| 83 | 0.928 | 0.466 | 55% | 6% | 6.38 | 12 | 5.9 | 5.8 | 0.1 |
| | | | | Formulations with different antacid capacity | | | | | |
| 91 | 0.71 | 0.358 | 50% | 6% | 6.37 | 8 | 6.0 | 5.7 | 0.3 |
| 92 | 0.925 | 0.464 | 50% | 6% | 6.24 | 11-12 | 6.0 | 5.7 | 0.3 |
| 93 | 1.100 | 0.553 | 50% | 6% | 6.5 | 15-16 | 6.1 | 5.8 | 0.3 |
| 94 | 1.324 | 0.664 | 50% | 6% | 6.11 | 19-20 | 5.9 | 5.8 | 0.1 |
| | | | | Three repeats | | | | | |
| 95 | 0.928 | 0.466 | 55% | 6% | 6.3 | 12 | 6.0 | 5.9 | 0.1 |
| 96 | 0.928 | 0.466 | 55% | 6% | 6.55 | 12-13 | 6.1 | 6.0 | 0.1 |
| 97 | 0.928 | 0.466 | 55% | 6% | 6.3 | 12-13 | 5.9 | 5.8 | 0.1 |
| | | | | Effect of pH | | | | | |
| 103 | up to pH 5.09 | 0.466 | 55% | 6% | 4.94 | °° | °° | °° | °° |
| 104 | 0.610 | 0.466 | 55% | 6% | 4.94 | °° | °° | °° | °° |
| 105 | 0.69 | 0.466 | 55% | 6% | 5.15 | 6 | 5.8 | 5.5 | 0.3 |
| 106 | 0.928 | 0.466 | 55% | 6% | 6.09/ 6.10° | 12 | 6.1 | 6.0 | 0.1 |
| 107 | 0.928 | 0.466 | 55% | 6% | °° | 12 | °° | °° | °° |
| 108 | 0.69 | 0.630 | 53.15% | 6% | °° | °° | °° | °° | °° |
| 109 | 0.69 | 0.630 | 55% | 6% | °° | °° | °° | °° | °° |
| 131 | 0.93 | 0.466 | 55% | 6% | 6.45 | 12 | ND | ND | ND |
| 132 | 0.94 | 0.466 | 55% | 6% | 6.76 | 13 | 6.1 | 5.8 | 0.3 |
| 136 | 0.94 | 0.463 | 55% | 6% | 9.36 | °° | °° | °° | °° |
| 137 | 0.94 | 0.460 | 55% | 6% | 9.37 | °° | °° | °° | °° |
| 138 | 0.94 | 0.457 | 55% | 6% | °°9.67 | °° | °° | °° | °° |
| 139 | 0.94 | 0.455 | 55% | 6% | °°9.92 | °° | °° | °° | °° |
| 140 | 0.94 | 0.452 | 55% | 6% | °°10.25 | °° | °° | °° | °° |
| 141 | 0.93 | 0.466 | 55% | 6% | °° | °° | °° | °° | °° |
| 142 | 0.93 | 0.471 | 55% | 6% | °° | °° | °° | °° | °° |
| 145 | 0.93 | 0.463 | 55% | 6% | 7.66/ 7.55° | 13 | 6.1 | 5.8 | 0.3 |
| 144 | 0.93 | 0.460 | 55% | 6% | 7.73/ 7.80° | 12-13 | 6.1 | 6.0 | 0.1 |
| 143 | 0.93 | 0.458 | 55% | 6% | 7.96/ 7.90° | 13-14 | 6.0 | 5.5 | 0.5 |
| 124 | 0.95 | 0.466 | 55% | 6% | 9.48 | 13 | 5.9 | <2.85 | >3 |
| | | | | Different sources of commercial adipate | | | | | |
| 122 | 0.92 | 0.466 | 55% | 6% | 6.36 | 12 | 6.0 | 5.9 | 0.1 |
| 123 | 0.92 | 0.466 | 55% | 6% | 6.32 | 13 | 5.8 | 5.7 | 0.1 |

TABLE 19-continued

| N° | NaOH (M) | Adipic acid (M) | Sucrose % w/w | DMEM % w/w | BRR* pH at t = 0 | BRR* time at pH > 4 (min) | Viral Titer at t = 0 (log₁₀ ffu per vaccine dose) | Viral titer after 1 w 37° C. (log₁₀ ffu per vaccine dose) | Viral loss after 1 w 37° C. (log₁₀ ffu per vaccine dose) |
|---|---|---|---|---|---|---|---|---|---|
| Different sources of commercial sucrose | | | | | | | | | |
| 133 | 0.92 | 0.466 | 55% | 6% | 6.34 | 13 | 5.8 | 5.8 | 0 |
| 147 | 0.92 | 0.466 | 55% | 6% | 6.32 | 11-12 | 6.0 | 5.7 | 0.3 |
| 134 | 0.92 | 0.466 | 55% | 6% | 6.34 | 13 | 6.3 | 5.8 | 0.5 |
| 148 | 0.92 | 0.466 | 55% | 6% | 6.34 | 11-12 | 5.8 | 5.9 | 0 |

*assessed by the Baby Rossett Rice (BRR) test as adapted according to Example III.2.2;
ND = not determined;
°= repeat
°° Formulation 45 was discarded because the antacid capacity was too long
°° Formulations 103, 104 and 108, 109 were discarded because adipic acid recrystallises on standing at 4-8° C.
°° Formulations n°107, 141 and 142 were discarded because they were similar to formulation already under evaluation
°°Formulations n°136-140 were discarded because the initial pH was too high II.5.2. Rotavirus Stability and Antacid Capacity—Results Rotavirus viral titration at different points in time has been evaluated according to the procedure given in Example III.1 and the antacid capacity of the formulation has been evaluated following the protocol given in Example III.2.2. The results are illustrated in Tables 19, 20, 21 and 22.

TABLE 20

| Viral stability at room temperature | | | | | | | | |
|---|---|---|---|---|---|---|---|---|
| Viral titration after storage at room temperature (log₁₀ ffu per vaccine dose) | | | | | | | | |
| n° | 1 m* | 2 m* | 3 m* | 4 m* | 5 m* | 6 m* | 7 m* | 8 m* |
| 63 | 5.8 | 5.8 | 5.5 | 5.5 | 5.0 | | | |
| 81 | | 5.5 | | | | 4.9 | | |
| 82 | | 5.4 | | | | 4.9 | | |
| 83 | | 5.6 | | | | 5.1 | 5.0 | |
| 91 | | 5.6 | | | 5.4 | 5.3 | 5.0 | |
| 92 | | 5.5 | | | 5.3 | 5.2 | 5.0 | |
| 93 | | 5.6 | | | 5.5 | 5.5 | 5.2 | 4.9 |
| 94 | | 5.6 | | | 4.6 | | | |
| 95 | | 5.6 | | 5.5 | 5.4 | 5.4 | 5.4 | 5.1 |
| 96 | | 5.8 | | 5.8 | 5.5 | 5.7 | 5.7 | 5.2 |
| 97 | | 5.7 | | 5.5 | 5.4 | 5.3 | 5.4 | 4.9 |
| 105 | | | | | 4.8 | | | |
| 106 | | | | | | | 5.2 | 4.7 |
| 132 | | | | | 5.8 | 5.8 | 5.5 | |

*= month(s);
Blank boxes = not determined

TABLE 21

| Viral stability at 4° C. | | | | | | | | | |
|---|---|---|---|---|---|---|---|---|---|
| Viral titration after storage at 4° C. (log₁₀ ffu per vaccine dose) | | | | | | | | | |
| n° | T = 0 | after 1 w 37° C. | 1 m* 4° C. | 2 m* 4° C. | 4 m* 4° C. | 6 m* 4° C. | 9 m* 4° C. | 12 m* 4° C. | 15 m* 4° C. |
| 63 | 6.0 | 5.6 | 6.0 | 5.9 | 6.1 | 6.0 | | 5.8 | |
| 81 | 5.9 | 5.7 | | 5.6 | | 5.4 | | 6.0 | |
| 82 | 5.9 | 5.7 | | 5.7 | | 5.4 | | 5.8 | |
| 83 | 5.9 | 5.8 | | 5.8 | | 5.7 | | 5.9 | |
| 91 | 6.0 | 5.7 | | 5.8 | | 5.8 | | 5.8 | |
| 92 | 6.0 | 5.7 | | 5.9 | | 5.9 | | 5.8 | |
| 93 | 6.1 | 5.8 | | 5.7 | | 6.1 | | 5.7 | |
| 94 | 5.9 | 5.8 | | 6.1 | | 6.2 | | 5.8 | |
| 95 | 6.0 | 5.9 | | 5.9 | | 5.8 | | 5.8 | 5.9 |
| 96 | 6.1 | 6.0 | | 5.7 | | 5.9 | | 5.9 | 5.8 |
| 97 | 5.9 | 5.8 | | 5.7 | | 5.8 | | 5.8 | 5.9 |
| 105 | 5.8 | 5.5 | | | | 5.9 | | 5.7 | |
| 106 | 6.1 | 6.0 | | | | 6.0 | | 5.8 | |
| 132 | 6.1 | 5.8 | | | | 5.8 | | 5.8 | |
| 122 | 6.0 | 5.9 | | | | 5.8 | | 5.9 | |
| 123 | 5.8 | 5.7 | | | | 5.9 | | 5.8 | |
| 133 | 5.8 | 5.8 | | | | 6.0 | | 5.8 | |
| 134 | 6.3 | 5.8 | | | | 6.0 | | 5.7 | |
| 143 | 6.0 | 5.5 | | | | | | 5.5 | |
| 144 | 6.1 | 6.0 | | | | | | 5.4 | |
| 145 | 6.1 | 5.8 | | | | | | 5.4 | |

*= month(s);
Blank boxes = not determined

The antacid capacity of formulations 91-94 was measured by the 'Baby Rossett-Rice method' (see Example III.2.2) and shows the possibilities to reach 8, 12, 16, or 20 min at a pH>4. The results are shown in Table 22 and in FIG. 2A.

TABLE 22

| time (min) | Formulation 94 pH | Formulation 93 pH | Formulation 92 pH | Formulation 91 pH |
|---|---|---|---|---|
| 0 | 6.11 | 6.5 | 6.24 | 6.37 |
| 1 | 5.11 | 5.07 | 4.93 | 4.79 |
| 2 | 5.03 | 4.98 | 4.84 | 4.67 |
| 3 | 4.96 | 4.9 | 4.75 | 4.56 |
| 4 | 4.90 | 4.83 | 4.67 | 4.45 |
| 5 | 4.85 | 4.76 | 4.58 | 4.34 |

TABLE 22-continued

| time (min) | Formulation 94 pH | Formulation 93 pH | Formulation 92 pH | Formulation 91 pH |
|---|---|---|---|---|
| 6 | 4.79 | 4.69 | 4.51 | 4.23 |
| 7 | 4.74 | 4.62 | 4.42 | 4.12 |
| 8 | 4.68 | 4.56 | 4.34 | 4.00 |
| 9 | 4.63 | 4.49 | 4.26 | 3.86 |
| 10 | 4.57 | 4.42 | 4.17 | 3.70 |
| 11 | 4.51 | 4.36 | 4.08 | |
| 12 | 4.46 | 4.29 | 3.98 | |
| 13 | 4.40 | 4.22 | 3.87 | |
| 14 | 4.35 | 4.15 | 3.75 | |
| 15 | 4.29 | 4.07 | 3.6 | |
| 16 | 4.23 | 3.98 | | |
| 17 | 4.17 | 3.88 | | |
| 18 | 4.11 | 3.78 | | |
| 19 | 4.05 | 3.66 | | |
| 20 | 3.98 | | | |
| 21 | 3.91 | | | |
| 22 | 3.83 | | | |
| 23 | 3.75 | | | |
| 24 | 3.65 | | | |

In conclusion, as was observed for the other carboxylate formulations, in the adipate series, a high pH value did not give good stability data (see for example formulation 124 which has a pH of 9.5 and exhibits more than 2.85 log of viral loss after 1 week storage at 37° C.).

The highest acceptability limit value of pH is about 8.0 (see for example the pH value of 7.96 obtained for formulation 143) for which a viral loss of 0.5 log is observed after 1 week at 37° C.

A suitable pH range is between about pH 5.5 and about pH 8 for these formulations, with a most suitable range of between pH 6.0 and pH 7.7.

Adipate (a food additive material) formulation is a good compromise with optimal $pK_a$ values ($pK_{a1}$ 5.4 and $pK_{a2}$ 4.43) which allow the target antacid capacity (e.g. t=12 min) to be reached using reasonable quantities of material (about 100 mg per dose). In addition, these quantities are compatible with solubility parameters thereby allowing formulating the vaccine in a dose volume of 1.5 ml. This is not possible with the classical citrate phosphate formulations due to technical impracticalities such as the crystallization of phosphate (see comparative Example IV). They are also compatible with toxicity parameters as toxicity data are rather low (oral LD50 in rat: 5.7 g/kg) for adipate as compared to other carboxylates.

II.5.3. Effect of Virus Titer in the Vaccine Dose on Virus Stability

The following experiment was carried out to evaluate the effect of the initial rotavirus titer (of $10^{6.0}$, $10^{6.5}$, $10^{5.2}$) in a vaccine dose of 1.5 ml on the stability of rotavirus.

Rotavirus viral titration at different points in time has been evaluated according to the procedure given in Example III.1 and the antacid capacity of the formulation according to the protocol given in Example III.2.2. The results are illustrated in Tables 23, 24, and 25.

TABLE 23

| N° | NaOH (M) | Adipic acid (M) | Target Viral titer $\log_{10}$ ffu | Sucrose % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 100 | 0.928 | 0.466 | 6.0 | 55% | 6.59 | 12 | 6.0 | 5.7 | 0.3 |
| 101 | 0.928 | 0.466 | 6.5 | 55% | 6.96 | 12 | 6.7 | 6.5 | 0.2 |
| 102 | 0.928 | 0.466 | 5.2 | 55% | 6.45 | 12 | 5.4 | 5.4 | 0 |

*assessed by the Baby Rossett Rice (BRR) test as adapted according to Example III.2.2.

TABLE 24

Viral stability at room temperature

Viral titration after storage at room temperature ($\log_{10}$ ffu per vaccine dose)

| N° | 1 m* | 2 m* | 3 m* | 4 m* | 5 m* | 6 m* | 7 m* | 8 m* | 9 m* | 10 m* |
|---|---|---|---|---|---|---|---|---|---|---|
| 100 | | | | | | 5.4 | 5..0 | | | |
| 101 | | | | | | 6.0 | 5.5 | | | |
| 102 | | | | | | 4.9 | 4.4 | | | |

*= month(s);
blank boxes = not determined

TABLE 25

Viral stability at 4° C.

| N° | Viral Titer at t = 0 | Viral titer after 1 w 37° C. | 1 m* | 2 m* | 3 m* | 4 m* | 6 m* | 12 m* |
|---|---|---|---|---|---|---|---|---|
| 100 | 6.0 | 5.7 | | | | | 6.0 | 5.8 |
| 101 | 6.7 | 6.5 | | | | | 6.6 | 6.4 |
| 102 | 5.4 | 5.4 | | | | | 5.3 | 5.2 |

*= month(s);
blank boxes = not determined

In conclusion, in the evaluated range, rotavirus stability remains similar and acceptable whatever the initial virus titer.

II.5.4. Formulations with Adipate in the Presence of Calcium Ions

It has been reported that calcium may influence the stability and conformation of rotavirus SA11 glycoprotein VP7 expressed in *Dictyostelium discoideum* (K. R. Emslie et al., 1996, Journal of Biotechnology 50, 149-159). It may be beneficial to add calcium ions to the adipate rotavirus liquid formulation of the invention, as they may contribute to the stabilization of rotavirus within the formulation. Accordingly, various quantities of calcium ions have been tested in the adipate formulation (Table 26). Two alternatives have been tested: $CaCl_2$ and $Ca(OH)_2$.

Formulations 98, 116-118: to 9.28 g NaOH are successively added: water (quantity determined so as to reach a final 325 g preparation), 17.00 g adipic acid, $CaCl_2$ as specified in Table 26, (a precipitation occurs, but the precipitate redissolves after one hour stirring at room temperature, except in formulation no 117), and 178.75 g of sucrose. The rest of the formulation steps are identical to those described for formulation 82. In this formulation DMEM represent 6% w/w.

Formulation 99: to water (quantity determined so as to reach a final 325 g preparation) are successively added: $Ca(OH)_2$ as specified in Table 26, 17.00 g adipic acid, 9.02 g NaOH and 178.75 g of sucrose. The rest of the formulation steps are identical to those described for formulation 82. In this formulation DMEM represent 6% w/w. Rotavirus viral titration at different points in time has been evaluated according to the procedure given in Example III.1 and the antacid capacity of the formulation has been evaluated following the protocol given in Example III.2.2. The results are illustrated in Tables 26, 27 and 28.

Formulations 119-121: to $CaCl_2$ as specified in Table 26 are successively added: water (quantity determined so as to reach a final 325 g preparation), 9.28 g NaOH (in this case precipitation of $Ca(OH)_2$ occur, but the precipitate redissolves after the adipic acid addition except in formulation no 121), 17.00 g adipic acid and 178.75 g of sucrose. The rest of the formulation steps are identical to those described for formulation 82. In this formulation DMEM represent 6% w/w.

TABLE 26

| N° | NaOH (M) | Adipic acid (M) | $CaCl_2$ (M) / $Ca(OH)_2$ (M) | Sucrose % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | $CaCl_2$ (M) | | | | ($\log_{10}$ ffu per vaccine dose) | | |
| 98 | 0.928 | 0.466 | 0.013 | 55% | 6.59 | 12-13 | 6 | 5.8 | 0.2 |
| 118 | 0.928 | 0.466 | 0.004 | 55% | 6.96 | 12 | 6.1 | 5.8 | 0.3 |
| 116 | 0.928 | 0.466 | 0.0129 | 55% | 6.45 | 12 | 5.9 | 5.8 | 0.1 |
| 119 | 0.928 | 0.466 | 0.0132 | 55% | 6.36 | 12 | 5.9 | 6 | 0 |
| 117 | 0.928 | 0.466 | 0.018 | 55% | ∞∞ | ∞∞ | ∞∞ | ∞∞ | ∞∞ |
| 120 | 0.928 | 0.466 | 0.019 | 55% | 6.18 | 11-12 | 6 | 5.8 | 0.2 |
| 121 | 0.928 | 0.466 | 0.051 | 55% | ∞∞ | ∞∞ | ∞∞ | ∞∞ | ∞∞ |
| | | | $Ca(OH)_2$ (M) | | | | | | |
| 99 | 0.902 | 0.466 | 0.0086 | 55% | 6.54 | 13-14 | 5.8 | 5.7 | 0.1 |

*assessed by the Baby Rossett Rice (BRR) test as adapted according to Example III.2.2.
∞∞ Formulations 117 and 121 were discarded because some precipitation of insoluble material occurred during their preparations

TABLE 27

Viral stability at room temperature

Viral titration after storage at room temperature ($\log_{10}$ ffu per vaccine dose)

| N° | 1 m* | 2 m* | 3 m* | 4 m* | 5 m* | 6 m* | 7 m* | 8 m* | 9 m* | 10 m* |
|---|---|---|---|---|---|---|---|---|---|---|
| 98 | | | | | 5.5 | 5.7 | 5.5 | 5.2 | | |
| 118 | | | | | 6.0 | 5.7 | | | | 5.0 |
| 116 | | | | | 5.9 | 5.6 | | | | 5.1 |
| 119 | | | | | 5.8 | 5.3 | | | | |
| 120 | | | | | 5.7 | 5.1 | | | | |
| 99 | | | | | 5.4 | 5.4 | 5.2 | 4.9 | | |

*= month(s);
blank boxes = not determined

TABLE 28

Viral stability at 4° C.

| N° | Viral Titer at t = 0 | Viral titer after 1 w 37° C. | 1 m* | 2 m* | 3 m* | 4 m* | 6 m* | 12 m* |
|---|---|---|---|---|---|---|---|---|
| 98 | 6 | 5.8 | | | | | 5.8 | 6.0 |
| 118 | 6.1 | 5.8 | | | | | 6.2 | 6.1 |
| 116 | 5.9 | 5.8 | | | | | 5.9 | 6.1 |
| 119 | 5.9 | 6 | | | | | 5.9 | 5.9 |
| 120 | 6 | 5.8 | | | | | 5.9 | 5.9 |
| 99 | 5.8 | 5.7 | | | | | 5.9 | 5.9 |

*= month(s);
blank boxes = not determined

Conclusion: the stability of rotavirus in presence of calcium ions is illustrated: no more that 0.3 log loss is experienced after 1 week at 37° C., which is similar to the result obtained for formulations made in the same conditions and containing the same ingredients except the added calcium ions (see for example formulation 83 in Tables 19-21).

II.5.5 Formulations with Adipate in the Presence of Oral Polio Viruses

Some routine immunization schemes may associate at the same point in time oral polio and rotavirus vaccinations. The objective of the following experiment was to assess whether both vaccinations were compatible. An experimental oral polio/rotavirus combined vaccine was therefore prepared.

Composition of OPV Medium Used for Formulations 149, 151-155

Water for injection: 80.00 L
Lactalbumine hydrolysat: 1500.00 g
Water for injection: 200.00 L
Sodium chloride: 2040.00 g
Potassium chloride: 120.00 g
Magnesium sulfate $7.H_2O$: 30.00 g
$KH_2PO_4$: 38.00 g
Glucose anhydre: 1200.00 g Neomycine sulfate: 15.00 g
Tween 80: 6.00 g
Calcium chloride.2H2O: 80.00 g
Sodium hydroxide: 30.00 g
Sodium bicarbonate: 660.00 g
Phenol red: 6.00 g
L-cystine: 30.00 g
Hydrochloric acide 1N, 550.00 g
Polymixixine B sulfate: 30.00 g
Water for injection up to 300.00 L Formulations 149-155: To water (quantity determined so as to reach a final 325 g preparation) are successively added: NaOH and adipic acid in quantities as described in Table 29, and 178.75 g sucrose. After complete dissolution the solution is sterilized by filtration on a 0.2 μm membrane. Under sterile conditions, and following the quantities as described in Table 29, DMEM medium containing the necessary quantity of rotavirus to obtain $10^{6.5}$ CCID50 per dose and OPV medium containing the necessary quantities of Polio viruses to obtain $10^{6.6}$ of type I, $10^{5.6}$ of type II, $10^{6.1}$ of type III CCID50 per dose were added. In this case the dose is 1.5 ml or 1.95 g. The resulting mixture is homogenised and distributed in the appropriate dose container. In those examples DMEM represent 6% w/w, sucrose is at 55% w/w, NaOH is 0.92M, adipic acid is 0.466M.

TABLE 29

| | NaOH g | Adipic acid g | water g | Rota Medium DMEM g | Rota-virus g | OPV medium g | OPV Type I g | OPV Type II g | OPV Type III g |
|---|---|---|---|---|---|---|---|---|---|
| 149 | 9.2 | 17 | 92.55 | 19.5 | — | 8.00 | — | — | — |
| 150 | 9.2 | 17 | 100.55 | 14.24 | 5.26 | — | — | — | — |
| 151 | 9.2 | 17 | 92.55 | 14.24 | 5.26 | 8.00 | — | — | — |
| 152 | 9.2 | 17 | 92.55 | 19.5 | — | 0.07 | 5.30 | 0.53 | 2.10 |
| 153 | 9.2 | 17 | 92.55 | 19.5 | — | 2.70 | 5.30 | — | — |
| 154 | 9.2 | 17 | 92.55 | 19.5 | — | 7.47 | — | 0.53 | — |
| 155 | 9.2 | 17 | 92.55 | 19.5 | — | 5.90 | — | — | 2.10 |

Rotavirus viral titration at different points in time has been evaluated according to the procedure given in Example III.1 and the antacid capacity of the formulation has been evaluated following the protocol given in Example III.2.2. The results are illustrated in Table 30.

TABLE 30

(In this table: all viral titers in CCID50/dose**)

| | BRR* min | Target Rota | Target OPV Type I | Target OPV Type II | Target OPV Type III | Rota Titer t = 0 4° C. | Rota Titer 1 w 37° C. | OPV I titer | OPV II titer | OPV III titer |
|---|---|---|---|---|---|---|---|---|---|---|
| 149 | 12 | no | no | no | no | | | | | |
| 150 | | $10^{6.5}$ | no | no | no | $10^{6.2}$ | $10^{6.2}$ | | | |
| 151 | | $10^{6.5}$ | no | no | no | $10^{6.3}$ | $10^{6.3}$ | | | |
| 152 | | no | $10^{6.6}$ | $10^{5.6}$ | $10^{6.1}$ | | | $10^{6.7}$ | $10^{5.6}$ | $10^{6.2}$ |
| 153 | | no | $10^{6.6}$ | no | no | | | | | |
| 154 | | no | no | $10^{5.6}$ | no | | | | | |
| 155 | | no | no | no | $10^{6.1}$ | | | | | |

*assessed by the Baby Rossett Rice (BRR) test as adapted according to Example III.2.2.

**It can be estimated that the correspondence between ffu and CCID50 is about 0.5 log (for example $10^{6.0}$ as expressed in CCID50 is equivalent to roughly $10^{5.5}$ as expressed in ffu per dose).

Blank boxes: not determined

"no" means that the corresponding virus was not incorporated in the formula

Conclusions:
1) Polio medium is compatible with antacid capacity (BRR 12 min in formulation no 149).

2) Polio medium is compatible with Rotavirus (comparing formulation no 150 to formulation no 151, where it can be seen that the same titers are obtained for both formulations, both at t=0 4° C. and after one week at 37° C.).

3) Rotavirus composition is compatible with poliovirus (obtained expected polio viral titer in formulation no 152).

II.5.6 Stability of the Adipate Formulations During a Freezing Event

II.5.6.1. Freezing at −20° C.

Rotavirus formulation no 95, after 6 months stored between +4° C. and +8° C., was submitted to 3 successive freezing (−20° C.) events according to the following timing (Table 31)

II.5.6.2. Freezing at −70° C.

Rotavirus formulation no 95, after 14 months stored between +4° C. and +8° C., was submitted to one freezing at −70° C. event according to the following timing (Table 31):

TABLE 31

|  | T = +4° C. | T = −20° C. | T = −70° C. |
|---|---|---|---|
| Duration at −20° C. | | | |
| t = 0 (after 6 months at 4-8° C.) | | 9 vials | |
| t = 120 days | Back from −20: 9 vials | | |
| t = 120 days | 3 vials: 1 × −20° C. | 6 vials | |
| t = 196 days | Back from −20: 6 vials | | |
| t = 197 days | 3 vials: 2 × −20° C. | 3 vials | |
| t = 224 days | Back from −20: 3 vials: 3 × −20° C. | | |
| Duration at −70° C. | | | |
| t = 0 (after 14 months at 4-8° C.) | | | 3 vials |
| t = 15 days | Back from −70: 3 vials 1 × −70° C. | | |

The samples were analyzed and compared to the viral titer at t=0 (4° C.) and also to the viral titer of samples of the same age stored at the usual refrigerator temperature (15 months at +4° C. in this case). Results are shown in Table 32.

TABLE 32

|  | t = 0, 4° C. | t = 15 months, 4° C. |
|---|---|---|
| N° 95 | 6.0 | 5.9 |
| N° 95 1 × −20° C. | | 5.8 |
| N° 95 2 × −20° C. | | 5.9 |
| N° 95 3 × −20° C. | | 5.9 |
| N° 95 1 × −70° C. | | 5.9 |

In conclusion, the composition of formulation no 95 (adipate formulation) is compatible with at least 3 successive freezing events at −20° C. it is also compatible with at least one freezing event at −70° C.

II.6. Formulations with Malate as a Carboxylate

II.6.1. Formulations presented in Table 33 (excepted formulations 46, 64, 84, 85 and 86) have been made at 325 g scale (250 ml) representing 166.6 doses of 1.5 ml (1.95 g) each. Antacid materials: D,L-Malic acid (Mw 146), NaOH (Mw 40).

Formulation no 46 has been made at 44 g scale (35 ml) representing 20 doses of 1.75 ml (2.2 g) each. Antacid materials: D,L-Malic acid (Mw 146), NaOH (Mw 40).

Formulation 46: to 15.74 g water (quantity determined so as to reach a final 44 g preparation) are successively added: 2.4 g NaOH, 4.0211 g malic acid and 19.5 g of sucrose (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

Formulation no 64 has been made at 318.4 g scale (244.5 ml) representing 163 doses of 1.5 ml (1.95 g) each. Antacid materials: D,L-Malic acid (Mw 146), NaOH (Mw 40).

Formulation no 84 has been made at 130 g scale (100 ml) representing 66.6 doses of 1.5 ml (1.95 g) each. Antacid materials: D-Malic acid (Mw 146), NaOH (Mw 40).

Formulation no 85 has been made at 130 g scale (100 ml) representing 66.6 doses of 1.5 ml (1.95 g) each. Antacid materials: L-Malic acid (Mw 146), NaOH (Mw 40).

Formulation no 86 has been made at 130 g scale (100 ml) representing 66.6 doses of 1.5 ml (1.95 g) each. Antacid materials: D,L-Malic acid (Mw 146), NaOH (Mw 40).

Formulation 64: to 97.3 g water (quantity determined so as to reach a final 318.4 g preparation) are successively added: 14.6 g NaOH, 24.50 g malic acid and 162.5 g of sucrose (51% w/w). After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The mixture is homogenized and distributed in the appropriate dose container. In this example DMEM represent 6.12% w/w.

Formulation 71: to 103.9 g water (quantity determined so as to reach a final 325 preparation) are successively added: 14.90 g NaOH, 25.00 g adipic acid and 162.5 g sucrose (50% w/w). The rest of the formulation steps are identical to those described for formulation 67. In this example DMEM represent 6% w/w.

Formulations 72-77, 84-86: it was proceeded as for formulation 71 but with adjusted amounts (see Table 33).

Formulation 78: to 75.00 g of water it is successively added: 8.00 g NaOH, 25.00 g malic acid, enough 1 N NaOH solution to reach a pH of 6.48, additional water to reach 325 g and 162.50 g sucrose (50% w/w). The rest of the formulation steps are identical to those described for formulation 67. In this example DMEM represent 6% w/w.

Formulations 79 and 80: it was proceeded as for formulation 78 but with adjusted amounts (see Table 33).

TABLE 33

| N° | NaOH (M) | Malic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 46 | 1.71 | 0.787 | 44% | 6% | 6.92 | 20 | 6.0 | 5.9 | 0.1 |
| 64 | 1.490 | 0.747 | 51% | 6.12% | 6.08 | 11-12 | 6.0 | 5.9 | 0.1 |
| 71 | 1.490 | 0.746 | 50% | 6% | 5.67 | 11 | 5.9 | 5.8 | 0.1 |
| 72 | 1.240 | 0.621 | 50% | 6% | 6.15/ 6.16° | 8 | 5.8 | 5.8 | 0 |
| 73 | 2.00 | 0.918 | 50% | 6% | ∞ | ∞ | ∞ | ∞ | ∞ |
| 74 | 1.490 | 0.746 | 53% | 6% | 5.19 | 8 | 5.8 | 5.8 | 0 |
| 75 | 1.490 | 0.746 | 56% | 6% | ∞ | ∞ | ∞ | ∞ | ∞ |
| 76 | 1.79 | 0.896 | 47% | 6% | 5.21 | 14 | 5.7 | 5.8 | 0 |
| 77 | 1.79 | 0.896 | 44% | 6% | 5.35 | 15 | 5.8 | 5.9 | 0 |
| 78 | up to pH 6.48 | 0.746 | 50% | 6% | 7.1/ 7.05° | 9 | 5.9 | 5.6 | 0.3 |
| 79 | up to pH 5.98 | 0.746 | 50% | 6% | 6.42/ 6.41° | 9 | 5.9 | 5.5 | 0.4 |

TABLE 33-continued

| N° | NaOH (M) | Malic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | ($\log_{10}$ ffu per vaccine dose) | | |
| 80 | up to pH 7.05 | 0.746 | 50% | 6% | 7.43 | 9-10 | 6.0 | 5.4 | 0.6 |
| 86 | 1.490 | 0.746 | 50% | 6% | 5.82 | 11 | 6.1 | 5.8 | 0.3 |
| 84 | 1.490 | 0.746 | 50% | 6% | 5.82 | 11 | 5.8 | 5.8 | 0 |
| 85 | 1.490 | 0.746 | 50% | 6% | 6.03 | 11 | 5.7 | 5.7 | 0 |

*assessed by the Baby Rossett Rice (BRR) test as adapted according to Example III.2.2;
°= repeat
°° Formulation 73 was discarded because of difficulties during sterile filtration due to high viscosity of the solution
°° Formulation 75 was discarded because of slow solubilisation of sucrose Rotavirus viral titration at different points in time has been evaluated according to the procedure given in Example III.1 and the antacid capacity of the formulation has been evaluated following the protocol given in Example III.2.2. The results are illustrated in Tables 33, 34 and 35.

TABLE 34

Viral stability at room temperature

Viral titration after storage at room temperature ($\log_{10}$ ffu per vaccine dose)

| N° | 1 m* | 2 m* | 3 m* | 4 m* | 5 m* | 6 m* | 7 m* | 8 m* | 9 m* | 10 m* |
|---|---|---|---|---|---|---|---|---|---|---|
| 64 | 5.8 | 5.9 | 5.6 | 5.7 | 5.2 | ND | ND | ND | ND | ND |
| 85 | ND | 5.7 | 5.2 | ND | ND | 4.7 | ND | ND | ND | ND |

*= month(s);
ND = not determined

TABLE 35

Viral stability at 4° C.

| N° | Viral Titer at t = 0 | Viral titer after 1 w 37° C. | 1 m* | 2 m* | 3 m* | 4 m* | 6 m* | 12 m* |
|---|---|---|---|---|---|---|---|---|
| 64 | 6.0 | 5.9 | 5.8 | 5.8 | ND | 5.8 | ND | 5.5 |
| 85 | 5.7 | 5.8 | ND | 5.8 | ND | ND | 5.6 | 5.7 |

*= month(s):
ND = not determined

II.6.2. Rotavirus Stability and Antacid Capacity—Results

The Rotavirus stability in a liquid malate formulation is related to the pH. The range of pH that was investigated, i.e. pH range of 6.0 to 7.0 gives a good stability during 1 week at 37° C.

II.7. Formulations with Glutamate

Aspartate and glutamate are aminoacids with a carboxylate group in their side chain. Values of the pKa of those side chain carboxylic acid are 3.65 and 4.25 respectively. Thus, glutamate with pKa higher that 4 can be used as buffer to build the antacid capacity. See Table 36.

Formulations 41: To water (quantity determined so as to reach a final 325 g preparation) are successively added: NaOH, glutamic acid and sucrose in quantities as described in Table 36. After complete dissolution the solution is sterilized by filtration on a 0.2 µm membrane. Under sterile conditions 19.5 g of DMEM medium containing the necessary quantity of rotavirus to obtain $10^{6.0}$ ffu per dose is added. In this case the dose is 1.5 ml or 1.95 g. The resulting mixture is homogenized and distributed in the appropriate dose container. In this example DMEM represent 6% w/w.

Formulation 43: To water (quantity determined so as to reach a final 44 g preparation) are successively added: 7.1 g monosodium glutamate 1H2O and 19.50 g sucrose (44% w/w). After complete dissolution the solution is sterilized by filtration on a 0.2 µm membrane. Under sterile conditions 2.64 g of DMEM medium containing the necessary quantity of rotavirus is added to the solution, to obtain $10^{6.0}$ ffu per dose. In this case the dose is 1.75 ml or 2.2 g. The mixture is homogenized and distributed in the appropriate dose container. In this example DMEM represent 6% w/w.

Formulation 61: To water (quantity determined so as to reach a final 325 g preparation) are successively added: 52.43 g monosodium glutamate 1H2O and 144 g sucrose (44% w/w). After complete dissolution the solution is sterilized by filtration on a 0.2 µm membrane. Under sterile conditions 19.5 g of DMEM medium containing the necessary quantity of rotavirus is added to the solution, to obtain $10^{6.0}$ ffu per dose. In this case the dose is 1.75 ml or 2.2 g. The mixture is homogenized and distributed in the appropriate dose container. In this example DMEM represent 6% w/w.

Formulation 68: To water (quantity determined so as to reach a final 250 g preparation) are successively added: 0.2 g monosodium glutamate 1H2O, 2.5 g bovine serum albumine, 0.250 g Na2HPO4.2H2O, 0.125 g KH2PO4, 0.5 g EDTA and 18.75 g sucrose (7.5% w/w). After complete dissolution the solution is sterilized by filtration on a 0.2 µm membrane. Under sterile conditions 19.5 g of DMEM medium containing the necessary quantity of rotavirus is added to the solution, to obtain $10^{6.0}$ ffu per dose. In this case the dose is 1.5 ml or close to 1.5 g. The mixture is homogenized and distributed in the appropriate dose container. In this example DMEM represent 7.8% w/w.

Rotavirus viral titration at different points in time has been evaluated according to the procedure given in Example III.1 and the antacid capacity of the formulation has been evaluated following the protocol given in Example III.2.2. The results are illustrated in Tables 36, 37 and 38.

TABLE 36

| N° | NaOH (M) | glutamic acid (M) | Sucrose % w/w | DMEM % w/w | BRR* pH at t = 0 | BRR* time at pH > 4 (min) | Viral Titer at t = 0 | Viral titer after 1 w 37° C. | Viral loss after 1 w 37° C. |
|---|---|---|---|---|---|---|---|---|---|
| | | | | | | | (log$_{10}$ ffu per vaccine dose) | | |
| 41 | 1.06 Na glutamate (M) | 0.542 | 51% | 6% | 10.36 | 15 | °° | °° | |
| 43 | | 1.088 | 44% | 6% | 6.92 | 12 | 6.0 | 5.8 | 0.2 |
| 61 | | 1.085 | 44% | 6% | 6.93 | 11-12 | 6.1 | 6.1 | 0 |
| 68 | | 0.0043 | 7.5% | 7.8% | 6.85 | <1 | 6.0 | <3 | >3 |

*assessed by the Baby Rossett Rice (BRR) test as adapted according to Example III.2.2.
°° Formulation 41 was discarded because its initial ph was to high
°° Formulation 68 was discarded from the long term stability study because of its unsatisfactory viral loss result obtained after 1 week at 37° C.

TABLE 37

Viral stability at room temperature

Viral titration after storage at room temperature (log$_{10}$ ffu per vaccine dose)

| N° | 1 m* | 2 m* | 3 m* | 4 m* | 5 m* | 6 m* | 7 m* | 8 m* | 9 m* | 10 m* |
|---|---|---|---|---|---|---|---|---|---|---|
| 41 | | | | | | | | | | |
| 43 | | | | | | | | | | |
| 61 | 6.1 | 5.7 | 5.6 | | | | | | | |
| 68 | | | | | | | | | | |

*= month(s);
blank boxes = not determined

TABLE 38

Viral stability at 4° C.

| N° | Viral Titer at t = 0 | Viral titer after 1 w 37° C. | 1 m* | 2 m* | 18 m* |
|---|---|---|---|---|---|
| 41 | | | | | |
| 43 | | | | | |
| 61 | 6.1 | 6.1 | 6.1 | 6.0 | 5.6 |
| 68 | | | | | |

*= month(s);
blank boxes = not determined

The Rotavirus stability in a liquid glutamate formulation is similar to the stability obtained with other carboxylates described here above. In short:

stability is better at pH around 7 (6.93 in formulation no 61) compared to more basic medium (ph 10.36 in formulation no 43)

stability is also better in high sucrose percentage (44% sucrose in formulation no 61 compared to 7.5% sucrose in formulation no 68)

profile curves of the stability at 1 week 37° C., at room temperature, and at 4-8° C. are similar to other carboxylates described here above.

II.8. Formulations with Fumarate

Formulation 44: to 16.28 g water (quantity determined so as to reach a final 44 g preparation) are successively added: 2.4 g NaOH, 3.4811 g fumaric acid and 19.5 g of sucrose (44% w/w). After one hour stirring at room temperature insoluble material remains in suspension. The preparation was discarded.

II.9. Formulations with Lactobionate

Formulation 47: to 16.02 g water (quantity determined so as to reach a final 44 g preparation) are successively added: 1.2 g NaOH, 10.7414 g lactobionic acid and 13.7 g of sucrose (31% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

II.10. Formulations with Maleate

Formulation 48: to 16.88 g water (quantity determined so as to reach a final 44 g preparation) are successively added: 2.4 g NaOH, 2.8821 g maleic anhydride and 19.5 g of sucrose (44% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

Formulation 57: to 110.3 g water (quantity determined so as to reach a final 325 g preparation) are successively added: 32.7 g disodium maleate and 162.5 g of sucrose (50% w/w). After complete dissolution the solution is sterilized by filtration on a 0.2 μm membrane. Under sterile conditions 19.5 g of DMEM medium containing the necessary quantity of rotavirus to obtain $10^{6.0}$ ffu per dose is added. In this case the dose is 1.5 ml or 1.95 g. The mixture is homogenized and distributed in the appropriate dose container. In this example DMEM represent 6.% w/w.

II.11. Formulations with Glucouronate

Formulation 49: to 16.14 g water (quantity determined so as to reach a final 44 g preparation) are successively added: 1.2 g NaOH, 5.8211 g glucuronic acid and 18.5 g of sucrose (42% w/w). After complete dissolution the solution is sterilized by filtration on a 0.2 μm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

II.12. Formulations with Galacturonate

Formulation 52: to 16.14 g water (quantity determined so as to reach a final 44 g preparation) are successively added: 1.2 g NaOH, 5.8218 g galacturonic acid and 18.5 g of sucrose (42% w/w). After complete dissolution the solution is sterilized by filtration on a 0.2 µm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

II.13. Formulations with Galactarate

Formulation 53: to 15.96 g water (quantity determined so as to reach a final 44 g preparation) are successively added: 2.4 g NaOH, 6.3008 g galactaric acid and 17.0 g of sucrose (38% w/w). After one hour stirring at room temperature insoluble material remains in suspension. The preparation was discarded.

II.14. Formulations with Tartarate

Formulation 55: to 15.26 g water (quantity determined so as to reach a final 44 g preparation) are successively added: 2.4 g NaOH, 4.4996 g tartaric acid and 19.5 g of sucrose (44% w/w). After complete dissolution the solution is sterilized by filtration on a 0.2 µm membrane. Under sterile conditions 2.34 g of DMEM medium containing the necessary quantity of rotavirus to obtain $10^{6.0}$ ffu per dose is added. In this case the dose is 1.75 ml or 2.2 g. The mixture is homogenized and distributed in the appropriate dose container. In this example DMEM represent 6.% w/w.

II.15. Overall Conclusion for Formulations Containing a Carboxylate in the Absence of Added Phosphate Several stable formulations have been prepared with various carboxylates, in the absence of added phosphate. The only phosphate present in these experimental formulations originated from the DMEM buffer and never exceeded 0.059 mM (5% w/w DMEM), 0.071 mM (6% w/w DMEM), or 0.094 mM (8% w/w DMEM). All tested carboxylates have shown the ability to act as buffering agents in neutralising the stomach acidity thereby preventing or minimising the inactivation of the active ingredient, i.e. the rotavirus antigen, present in the formulation. All tested formulations, made at various administration dose volumes (i.e. 1.5 ml, 2.0 ml and 2.5 ml), exhibited a pH of between about pH 5.0 to about pH 8.0, and for most formulations a pH of about pH 5.5 to about 7.5. These formulations performed well during the stability testing at the three tested storage temperatures (i.e. 37° C., room temperature or 4° C.). In addition, these formulations exhibited a satisfactory antacid capacity, i.e. an antacid capacity of at least 8 minutes, and for most formulations of at least 12 minutes, as assessed by the BRR test (see procedure in Example III.2.2).

In the following Table 39 is presented a short summary of the stability data obtained for selected adipate formulations according to the pH of the formulation. The following criteria were assessed: i) viral loss after storage during one week at 37° C. (accelerated stability) (\*), ii) time expressed in months within which the viral titer loss remains below 1.0 log (after storage at room temperature) together with the viral titer reached at the mentioned time period (\*\*), iii) viral titer in ffu/vaccine dose reached after storage during one year (12 months) at 4° C. (\*\*\*).

TABLE 39

| | pH$ | Viral loss after 1 w 37° C. | * | Room T° <1 log | ** | 4° C. 12 M | *** | **** |
|---|---|---|---|---|---|---|---|---|
| | | | | sucrose 45% | | | | |
| 82 | 6.39 | 0.2 | | 6 M 4.9 | | 5.8 | | |
| | | | | sucrose 50% | | | | |
| 63 | 6.49 | 0.4 | | 5 M 5.0 | | 5.8 | | |
| 81 | 6.2 | 0.2 | | 6 M 4.9 | | 6 | | |
| | | | | sucrose 55% | | | | |
| 124 | 9.48 | >3 | | not done | | | | |
| 143 | 8 | 0.5 |  | not done | | 5.5 | 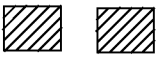 |  |
| 144 | 7.75 | 0.1 | | not done | | 5.4 | 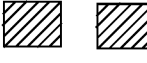 |  |
| 145 | 7.35 | 0.3 | | not done | | 5.4 | 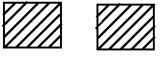 |  |
| 132 | 6.76 | 0.3 | | 6 M 5.5 | | 5.8 | | |
| 96 | 6.55 | 0.1 | | 8 M 5.2 | | 5.9 | | |
| 83 | 6.38 | 0.1 | | 7 M 5.0 | | 5.9 | | |
| 95 | 6.3 | 0.1 | | 8 M 5.1 | | 5.8 | | |
| 97 | 6.3 | 0.1 | | 8 M 4.9 | | 5.8 | | |
| 106 | 5.97 | 0.1 | | 6 M 5.2 | | 5.8 | | |
| 105 | 5.98 | 0.3 | | 5 M 4.8 |  | 5.7 | |  |
| 104 | 5.12 | 0.2 | crystallise | ■ | | | | |

TABLE 39-continued

| pH$ | Viral loss after 1 w 37° C. | * | | Room T° <1 log | ** | 4° C. 12 M | *** | **** |
|---|---|---|---|---|---|---|---|---|
| 103 | 5.09 | 0.4 | crystallise | ■ | | | | |

M = months
$ = pH as assessed at T = 0 (4° C.) by the BRR test according to Example III.2.2
*best results based on the 1 week 37° C. stability test - a maximum viral titer loss of 0.5 log is tolerated
**best results based on the room temperature stability test - a maximum viral titer loss of 1.0 log is tolerated
***best results based on the 4-8° C. stability test - a maximum viral titer loss of 0.5 log is tolerated
****cumulative best results - both a viral titer loss ≧0.5 log but <1.0 log, and a titer loss of <0.5 log are tolerated and both acceptable according to this criteria
Grey shading: acceptable formulation for the criteria assessed (*, , * or ***) with a viral loss <0.5 log; dashed box: acceptable formulation for the criteria assessed (*, , * or ***) with a viral loss ≧ 0.5 log but <1.0 log; black shading: unacceptable formulation as crystallization occurs.

Clearly, in the adipate formulations tested, the pH range of about 6.0 to about 8.0 (6-8) exhibited a good, acceptable, stability profile compatible with a maximum viral titer loss of 1.0 log, and the pH sub-range of about 6.0 to 6.8 (6-6.8) a good, acceptable, stability profile compatible with a maximum viral titer loss of 0.5 log.

Example III

Methods

III.1 Rotavirus Viral Titration

Detection of infectious rotaviruses is done by incubation of the formulation containing the rotavirus and various components on permissive MA104 cells (ATCC CRL 2378).

The Rotavirus (e.g. P43 rotavirus, ECACC 99081301) was formulated as described in the above examples. After inoculation of viral samples, the cells are incubated for 16 to 18 hours. The cells are then fixed and permeabilised with acetone 80%. Infected cells are identified by indirect immuno-fluorescence using a monoclonal anti-rotavirus antibody specific of the VP6 protein (Mab 9F6) detected by fluorescein-conjugated IgG and examined under UV microscope. Any commercially available monoclonal antibodies against rotavirus VP6 protein are suitable, and appropriate working dilutions will be determined by routine experimentation. For example the following monoclonals are suitable:

RV 11-2 (IgG2a, ascites fluid conjugated with fluorescein isothiocyanate) from Rural Technologies Inc (www.ruraltechinc.com)

5F8 F9 (IgG1, catalog number RVM-1601A-5) or 2F219 (IgG2b, catalog number RVM-1601B-5) from Austral Biologicals (www.australbiologicals.com)

MABR10 (IgG fraction) from Immunological and Biochemical testsystems Gmbh (www.afsbio.com)

Anti-Vp6 rotavirus polyclonal antibodies, for example AB1129F from Chemicon (www.chemicon.com) are also suitable.

Each fluorescent foci corresponds to one infectious virus. Titers are expressed as the logarithm of foci forming unit per ml (log(ffu/ml)). The precision of the viral titration is around + or −0.2 log. Results of viral titration in ffu/ml are converted to ffu/dose according to the initial sample volume dose. All data presented in the Tables are in log base 10 ($log_{10}$) ffu per dose.

Good results are those in which a <0.5 log decrease during the "1 week at 37° C." (accelerated stability test) is achieved. Formulations, which exhibit a viral loss of 1 log or above, are discarded from further stability testings.

III.2 Method for Antacid Measurement: Baby Rossett-Rice (BRR) Titration

III.2.1. Introduction

The Baby Rossett-Rice (BRR) Titration test has been adapted to a baby population from the Rossett-Rice Titration test originally developed for an adult population.

The Rossett-Rice titration is a well-known test used in the domain of antacid (see N. E. Rossett and Marion L. Rice in *Gastroenterology*, 1954 volume 26 pages 490-495: 'An in vitro evaluation of the efficacy of the more frequently used antacids with particular attention to tablets'). The Rossett-Rice titration measures the rate of reaction of the antacid substance under test with 0.1 N hydrochloric acid and the duration of elevated pH. To simulate the conditions in the empty stomach, fresh hydrochloric acid is added at once at the beginning of the measurement. To simulate the conditions in the stomach during the digestion process, fresh hydrochloric acid is added at a constant rate to the reaction mixture under test.

Briefly, the adult Rossett-Rice titration is divided in two parts:

the initial addition of 30 ml of 0.1N HCl, which represent the acidic content of the bolus of an empty stomach;

followed by the continuous addition, at a rate of 4 ml/min, of 0.1N HCl, which is a mimicry of the acid stomach secretion during digestion.

Those are the experimental conditions usually considered as representative of an average adult stomach.

III.2.2. Baby Rossett-Rice Titration Assay

Based on the standard Rossett-Rice conditions as descried in the original procedure, the test was adapted to be representative of a six month old baby stomach and is below referred to 'Baby Rossett-Rice (BRR) titration assay.

According to the Geigy Scientific Tables (Volume 1 page 126, Ciba-Geigy 1981, eds), the following data are of interest as far as stomach HCl excretion is concerned (see Table 40):

TABLE 40

| Children | Basal acid output Mean | Extreme range | Maximum acid output Mean | Extreme range |
|---|---|---|---|---|
| 9-11 weeks | 0.149 mmol/h | 0.05-0.30 mmol/h | 0.56 mmol/h | 0.39-0.84 mmol/h |
| 6-7 months | 0.193 mmol/h | 0.07-0.40 mmol/h | 2.08 mmol/h | 1.33-2.88 mmol/h |

So, based on those data, we choose the most severe conditions to encompass all situations:

Initial HCl quantity: 0.40 mmol (4 ml of 0.1N HCl)
Continuous addition of 0.1N HCl quantity: 2.90 mmol/h (or 0.048 mmol/min). In practice a rate of 0.5 ml/min of 0.1N HCl is used.

An outline of the experimental set-up of the BRR is shown in FIG. 2B.

Table 41 summarizes the difference between the BRR as compared to the original published procedure.

TABLE 41

| Name of the test: | Rossett-Rice | Baby-Rossett-Rice |
|---|---|---|
| Reference | Gastroenterology 1954 vol. 26 pages 490-495. see also Antacid test in Pharmacopeae | GSK unpublished data Values for stomach HCl secretion rates for babies are from Geigy Scientific Tables (1981) Volume 1 page 126. |
| Applying for: | Adults | 6 months babies |
| Temperature applied during the test | 37° C. | 37° C. |
| Beaker volume | 400 ml | 50 ml |
| Initial water volume | 70 ml | 8.5 ml if antacid sample is 1.5 ml 8.0 ml if antacid sample is 2.0 ml 7.5 ml if antacid sample is 2.5 ml |
| Antacid quantity | Equivalent to 0.330 g $Al_2O_3$ | Variable according to sample tested and dose volume; usually between 0.8 and 1.8 milli-equivalent of HCl |
| Initial 0.1 N HCl quantity added at t = 0 | 30 ml | 4 ml |
| Rate of additional 0.1N HCl added during measurement | 4 ml/min | 0.5 ml/min |
| Time measurement for the pH to reach: | pH = 3 | pH = 4 |
| Typical results | 3-4 hours above pH 3 | 8-20 min above pH 4 |

III.2.2.1. Working Procedure for the BRR Assay

The experimental set-up is presented in FIG. 2B.

1° Using a 50 ml beaker, place enough of water for injection in it in order to have, after the step no 4 (here after) a final liquid volume of 10 ml.

2° Install the beaker in a water bath.

3° The temperature of the water bath is adjusted in order to obtain 37° C. inside the beaker.

4° The sample of the antacid to be measured is added to the beaker.

5° Measurement of pH value at this stage represents the "initial pH" (the t=0 in the data table).

6° Add at once, 4 ml of 0.1N HCl (0.40 mmol), and at the same time start the clock and start the pump (continuous addition of 0.5 ml/min of 0.1N HCl). Those three actions should all occur within the 5 first seconds of the clock starting point.

7° Record the pH values along the time, until pH 4 is obtained. At the option of the operator, the decrease of the pH may be let to progress until pH 3 (as in the original Rossett-Roce method) is obtained, but the relevant antacid capacity values are recorded after pH 4 is reached.

8° Stop the clock and the pump.

III.2.2.2. Presentation of the Experimental Data

Experimental data are presented in Table for example see Table 22, from which a graphic presentation can be drawn: for example see FIG. 2A.

III.2.2.3. Results Interpretation

Rotavirus is destroyed when placed at pH below 4. In order then to preserve the virus, the time above pH 4 is of consideration. The result of the Baby Rossett-Rice titration is expressed in time units (minutes). It is the time for which the pH value was measured above 4, i.e. the so-called antacid capacity of the formulation. In some instances two values are recorded (e.g. 11-12 minutes like in Table 22 formulation no 92 where at 11 min the pH was 4.08 and at 12 min pH was 3.98, indicating that the passage at pH 4.00 was closer to 12 min than to 11 min.).

III.2.2.4. Calibration

Temperature is measured with a calibrated thermometer (−10° C.-+50° C. scale). The pH meter is calibrated using standard buffers at pH 7 and pH 4 that are commercially available.

The pump rate is adjusted by volume measurements against the time in order to obtain 0.5 ml/min. The peristaltic pump is an 8 rollers model from Ismatec S.A. Model MS-Reglo. In order to avoid drops formation the tubing extremity is placed along the beaker wall above the liquid level.

Hydrochloric acid 0.1N is the commercial standard titration solution.

A known standard buffer solution is used to check the experimental set-up before analysis of unknown antacid samples. This standard buffer solution is made of 24.066 g of trisodiumphosphate dodecahydrate (Merck product no 1.06578.1000) dissolved in enough water to obtain 1 liter of solution. Typically, 10 ml of this solution will give a pH of 9.0 occurring between minutes no 6 and 7 (first phosphate pH jump) and a pH of 4.0 occurring between minutes no 19 and 20 (second phosphate pH jump) in the so described Baby Rossett-Rice titration set-up. Results are shown in Table 42.

TABLE 42

| | Time (min) | 10 ml of Na3PO4•12H2O at 24.066 g/liter pH | 10 ml of water No antacid pH |
|---|---|---|---|
| | 0 | 12.4 | 5.94 |
| | 1 | 11.7 | 1.31 |
| | 2 | 11.58 | 1.23 |
| | 3 | 11.44 | 1.18 |
| | 4 | 11.27 | 1.14 |
| | 5 | 11.02 | 1.11 |
| first pH jump | 6 | 10.6 | 1.10 |
| | 7 | 8.86 | 1.07 |
| | 8 | 7.95 | 1.05 |
| | 9 | 7.6 | 1.03 |
| | 10 | 7.38 | 1.01 |
| | 11 | 7.19 | 0.99 |
| | 12 | 7.03 | 0.98 |
| | 13 | 6.88 | 0.97 |
| | 14 | 6.74 | 0.96 |
| | 15 | 6.58 | 0.95 |
| | 16 | 6.41 | 0.95 |
| | 17 | 6.21 | 0.94 |
| | 18 | 5.93 | 0.93 |
| second pH jump | 19 | 5.45 | 0.92 |
| | 20 | 3.47 | 0.91 |
| | 21 | 2.88 | 0.90 |
| | 22 | 2.62 | 0.89 |
| | 23 | 2.44 | 0.88 |
| | 24 | 2.3 | 0.87 |
| | 25 | 2.18 | 0.87 |
| | 26 | 2.09 | 0.86 |
| | 27 | 2.01 | 0.86 |
| | 28 | 1.93 | 0.86 |
| | 29 | 1.87 | 0.85 |
| | 30 | | |

III.3 Measurement of the Refractive Index of a Given Formulation

Several formulations illustrated in the present invention are prepared at small volume (1.5 ml dose volume for example, and below), contain a high sucrose concentration (e.g. 55%) and still must comply with the stability and antacid capacity requirements. It may be important therefore to verify that the formulation has been successfully prepared, and that complete solubilisation of each constituent has been achieved. One simple way to do this is to measure the refractive index of the formulation. Refractive index is a well-known simple measurement which can be used both at the carboxylate buffer stage (before rotavirus addition) and also at the final formulation step (after rotavirus addition).

III.3.1. Method

The index of refraction of aqueous solutions is a standard method to determine the sucrose concentration in solution. Table of refractive index versus sucrose concentrations can be find in the handbook of Chemistry and Physics $70^{th}$ edition 1989-1990 CRC Press page E 386.

Using a Index Instrument Automatic Refractometer GPR 11-37 instrument, a drop of solution is placed in the instrument and refractive index is recorded. Water is used as a standard to check the instrument (refractive index of 1.3330).

Several adipate formulations containing various amounts of sucrose have been prepared and submitted to the refractive index measurement. A repeat measurement was made.

III.3.2. Results

The results of those measurements are shown in FIGS. 3A and 3B. In conclusion, in the tested concentrations window, there is a linear correlation between the sugar concentrations and other soluble ingredients and the measured refractive index.

For example, in formulation no 95, after complete dissolution of the ingredients at the carboxylate buffer stage (before addition of the rotavirus) a refractive index value of 1.4578 (target sucrose concentration being 58.5% w/w in this case) will be obtained; while at the final stage of the formulation (after rotavirus addition or addition of 6% w/w DMEM in case of placebo preparation) a refractive index of 1.4480 (target sucrose concentration being 55% w/w in this case) will be obtained. In both cases, the measured refractive index values are higher that those obtained for a single 58.5% (refractive index of 1.4385) or 55% (refractive index of 1.4307) sucrose in water solution, indicating the refractive index contribution of other ingredients of the buffer preparation.

III.3.3. Conclusion

Thus, the refractive index measurement can be used to check quickly, during an in process control, the complete dissolution of all the added ingredients of the formulation.

Example IV

Formulation with Citrate Phosphate Buffer

Comparative Example

IV.1. Preparation of the Formulations (Tables 43 & 44)

TABLE 43

| N° | NaH2PO42H$_2$O (M) | Na2HPO4•2H$_2$O (M) | Na3 Citrate• 2H$_2$O (M) | Sucrose % w/w | DMEM % w/w | BRR$^\$$ pH at t = 0 | BRR$^\$$ Time at t = 0 pH > 4 min | Viral Titer at t = 0 | Viral Titer after 1 w 37° C. | Viral Loss After 1 W 37° C. |
|---|---|---|---|---|---|---|---|---|---|---|
| | | | | | | | | (log$_{10}$ ffu per vaccine dose) | | |
| 2.5 ml administration dose volume - phosphate concentration = 0.390 M | | | | | | | | | | |
| 1 | 0.195 | 0.195 | 0.135 | 50% | 3.33% | 6.66 | 9 | 5.9 | 5.4 | 0.5 |
| 2 | 0.195 | 0.195 | 0.135 | 50% | 5% | 6.65 | 10 | 5.8 | 5.4 | 0.4 |
| 3 | 0.195 | 0.195 | 0.135 | 50% | 8% | 6.67 | 9 | 5.6 | 5.3 | 0.3 |
| 4 | 0.195 | 0.195 | 0.135 | 45% | 3.33% | 6.67 | 10 | 5.8 | 5.3 | 0.5 |
| 5 | 0.195 | 0.195 | 0.135 | 40% | 3.33% | 6.69 | 11 | 5.8 | 5.5 | 0.3 |
| 6 | 0.195 | 0.195 | 0.135 | 30% | 3.33% | 6.71 | 10 | 5.7 | 5.5 | 0.2 |
| 7 | 0.195 | 0.195 | 0.135 | 20% | 3.33% | 6.75 | 11 | 5.6 | 4.1 | 1.5 |
| 8 | 0.195 | 0.195 | 0.135 | 45% | 8% | 6.69 | 12 | 5.7 | 5.4 | 0.3 |
| 9 | 0.195 | 0.195 | 0.135 | 40% | 8% | 6.70 | 12 | 6.1 | 5.6 | 0.5 |
| 10 | 0.195 | 0.195 | 0.135 | 30% | 8% | 6.72 | 11 | 6.1 | 5.4 | 0.5 |
| 11 | 0.195 | 0.195 | 0.135 | 20% | 8% | 6.73 | 11 | 6.1 | 4.4 | 1.7 |
| 2 ml administration dose volume - phosphate concentration = 0.488 M** | | | | | | | | | | |
| 17 | 0.244 | 0.244 | 0.162 | 50% | 6% | 6.68 | 10 | 5.7 | 5.5 | 0.2 |
| 1.5 ml administration volume - phosphate concentration = 0.650M** | | | | | | | | | | |
| 12 | 0.325 | 0.325 | 0.216 | 40% | 6% | ∘∘ | ∘∘ | ∘∘ | ∘∘ | ∘∘ |
| 13 | 0.325 | 0.325 | 0.216 | 40% | 8% | ∘∘ | ∘∘ | ∘∘ | ∘∘ | ∘∘ |
| 14 | 0.325 | 0.325 | 0.216 | 40% | 10% | ∘∘ | ∘∘ | ∘∘ | ∘∘ | ∘∘ |
| 15 | 0.325 | 0.325 | 0.216 | 45% | 6% | ∘∘ | ∘∘ | ∘∘ | ∘∘ | ∘∘ |
| 16 | 0.325 | 0.325 | 0.216 | 45% | 8% | ∘∘ | ∘∘ | ∘∘ | ∘∘ | ∘∘ |

$^\$$assessed by the Baby Rossett Rice (BRR) test as adapted according to Example III.2.2;

**This is equivalent to 0.390 M in a 2.5 ml dose volume

∘∘ Formulations 12-16 were discarded because recrystallisation occurred on standing at 4-8° C.

TABLE 44 reduced phosphate amount in a 1.5 ml dose volume

| N° | NaH2PO4 2H$_2$O (M) | Na2HPO4•2H$_2$O (M) | Na3 Citrate• 2H$_2$O (M) | Sucrose % w/w | DMEM % w/w | BRR$ pH at t = 0 | BRR$ Time at pH > 4 min | Viral Titer at t = 0 | Viral Titer after 1 w 37° C. | Viral Loss After 1 W 37° C. |
|---|---|---|---|---|---|---|---|---|---|---|
| | | | | | | | | (log$_{10}$ ffu per vaccine dose) | | |
| 1.5 ml administration dose volume reduced - phosphate amount (0.450 M for formulations 25-29)** | | | | | | | | | | |
| 25 | 0.225 | 0.225 | 0.285 | 40% | 6% | 6.69 | 12 | 6.2 | 5.8 | 0.4 |
| 26 | 0.225 | 0.225 | 0.285 | 40% | 8% | Crystallization occurs - no data available | | | | |
| 27 | 0.225 | 0.225 | 0.285 | 40% | 10% | 6.67 | 12 | 6.2 | 6.0 | 0.2 |
| 28 | 0.225 | 0.225 | 0.285 | 45% | 6% | Crystallization occurs - no data available | | | | |
| 29 | 0.225 | 0.225 | 0.285 | 45% | 8% | 6.69/ 6.72° | 12/ 12-13° | 6.1 | 6.1 | 0 |
| 1.5 ml administration dose volume - reduced phosphate amount (0.0085 M for formulations 30-32, 38-40)*** | | | | | | | | | | |
| 30 | 0.00424 | 0.00424 | 0.438 | 40% | 6% | 7.75 | 12-13 | 6.2 | 5.3 | 0.8 |
| 31* | 0.00424 | 0.00424 | 0.438 | 45% | 6% | 7.9 | 13 | 6.1 | 5.8 | 0.3 |
| 32* | 0.00424 | 0.00424 | 0.438 | 50% | 6% | 7.76 | 13-14 | 6.0 | 5.7 | 0.3 |
| 38 | 0.0042 | 0.0042 | 0.435 | 50% | 6% | 7.76 | 14 | 5.7 | 5.2 | 0.5 |
| 39 | 0.00424 | 0.00424 | 0.446 | 50% | 6% | 7.74 | 14 | 5.6 | 5.3 | 0.3 |
| 40 | 0.0043 | 0.0043 | 0.448 | 54% | 6% | 7.73 | 15 | 5.6 | 5.4 | 0.2 |
| 1.5 ml administration dose volume - no phosphate added | | | | | | | | | | |
| 18 | — | — | 0.438 | 40% | 6% | 8.42 | 12 | 5.7 | 4.5 | 1.2 |
| 19 | | | 0.437 | 40% | 8% | 8.42 | 11 | 5.7 | 4.3 | 1.4 |
| 20 | | | 0.437 | 40% | 10% | 8.31 | 11 | 5.7 | 4.4 | 1.3 |
| 21 | | | 0.437 | 45% | 6% | 8.35 | 11 | 5.9 | 4.7 | 1.2 |
| 22 | | | 0.437 | 45% | 8% | 8.35 | 10 | 5.8 | 4.9 | 0.9 |
| 23 | | | 0.437 | 45% | 10% | 8.37 | 12 | 5.7 | 4.7 | 1.0 |
| 24 | — | — | 0.438 | 50% | 6% | 8.31 | 11 | 5.7 | 4.9 | 0.8 |

°= repeat
$assessed by the Baby Rossett Rice (BRR) test as adapted according to Example III.2.2;
*formulations 31 & 32 were repeated in a different ab initio test with a similar date (formulations 38 & 39 respectively, not shown).
**this is equivalent to 0.271 M in a 2.5 ml dose volume; i.e. reduced phosphate
***this is equivalent to 0.0051 M in a 2.5 ml dose volume; i.e. reduced phosphate Note to Results of Formulations 18-24, 26-30 in Table 44

Formulations 18-24 and 30 were discarded from the long term stability study because of unsatisfactory results obtained during the 1 week stability test at 37° C. Formulations 26 and 28 were discarded because crystallisation occurred on 4-8° C. standing. Formulations 25, 27 and 29 were discarded because of a high risk of recrystallisation during 4-8° C. standing.

IV.1.1. Formulations 1-11: 2.5 ml Dose Volume Formulations

Formulation 1-11 (see Table 43) were made at the 325 g scale (250 ml) representing 100 doses of 2.5 ml (3.25 g) each. Antacid materials: NaH$_2$PO$_4$.2H$_2$O (Mw 156); Na$_2$HPO$_4$.2H$_2$O (Mw 178); Na$_3$Citrate.2H$_2$O (Mw 294).

Liquid formulation 1 was prepared as follows. To 125.84 g of water (quantity determined so as to reach a final 325 g preparation) are consecutively added: 7.605 g NaH$_2$PO$_4$.2H$_2$O, 8.677 g of Na$_2$HPO$_4$.2H$_2$O, 9.555 g of Na$_3$citrate .2H$_2$O and 162.5 g of sucrose. After complete dissolution the solution is sterilized by filtration on a 0.2 μm membrane. 10.82 g of DMEM medium containing the necessary quantity of rotavirus is added under sterile conditions to obtain 10$^{6.0}$ ffu per dose. The mix is homogenised and distributed in the appropriate dose container. In this case one dose consists of 2.5 ml or 3.25 g of the final formulated preparation. In this example DMEM medium represents 3.33% w/w.

Formulations 2-11 were prepared similarly (see ingredients and proportions in Table 43) In this series different amounts of sucrose and DMEM were tested.

Similar results were obtained with the exception of formulations 7 and 11 prepared with a low (20%) sucrose concentration, which did not adequately stabilize rotavirus.

IV.1.2. Formulation 17: 2.0 ml Dose Volume Formulation

Formulation 17 (see Table 43) was made at the 325 g scale (250 ml) representing 125 doses of 2.0 ml (2.60 g) each. Antacid materials: NaH$_2$PO$_4$.2H$_2$O (Mw 156); Na$_2$HPO$_4$.2H$_2$O (Mw 178); Na$_3$Citrate.2H$_2$O (Mw 294). Briefly, 110.7 g of water (quantity determined so as to reach a final 325 g preparation) is weighted and 9.51 g NaH$_2$PO$_4$.2H$_2$O, 10.84 g of Na$_2$HPO$_4$.2H$_2$O, 11.94 g of Na$_3$citrate .2H$_2$O and 162.5 g of sucrose (50% w/w) are added consecutively. In this example 19.5 g DMEM is used, which represents 6% w/w.

IV.1.3. Formulations 12-16: 1.5 ml Dose Volume Formulations

Further attempts to reduce the administration dose volume of those citrate/phosphate formulations (for details see Table 43) to a volume of below 2 ml failed.

Concentrations of ingredients used for formulation 17 (2 ml dose volume) were adjusted to 1.5 ml dose volume. Re-crystallisation of the phosphate component rapidly occurred upon storage of the formulation at 4° C. This phenomenon is due to the rather low solubility of Na$_2$HPO$_4$ within the phosphate citrate component (see Table 45).

TABLE 45

Theoretical solubility limits for phosphate and citrate

| | Solubility in water |
|---|---|
| $NaH_2PO_4 \cdot 2H_2O$ | 5.44 M (20° C.) |
| $Na_2HPO_4 \cdot 2H_2O$ | 0.52 M (20° C.) |
| $Na_3Citrate \cdot 2H_2O$ | 1.44 M (25° C.) |

According to these parameters, attempts to formulate formulation 17 in a 1.5 ml dose volume would theoretically result in a final phosphate concentration of 0.65 M ((0.244 M+0.244 M)*2/1.5), which is higher than the $Na_2HPO_4$ solubility data (0.52 M).

To avoid this low solubility problem of phosphate, it is suggested not to use additional phosphate, and to adjust for the pH by playing on the balance between the carboxylic acid form (R—COOH) and the carboxylate salt form (R—COO⁻). An example of this is given in formulations 100-115 made at a 2.5 ml administration volume (see Table 5) or formulation 128-130 realized at a 1.5 ml administration volume (see Table 6).

IV.1.4. Formulations 25-32 and 38-40:1.5 ml Dose Volume Formulations and Decreased Amount of Phosphate Several formulations (see Table 44 for details) containing a reduced amount of phosphate were prepared at the 325 g scale (250 ml) representing 166.6 doses of 1.5 ml (1.95 g) each. In order to compensate for this decrease in phosphate whilst maintaining an acceptable antacid capacity, citrate concentration was increased. Briefly, formulation 25 was prepared by mixing 8.76 g $NaH_2PO_4.2H_2O$, 10.00 g of $Na_2HPO_4.2H_2O$, 21.00 g of $Na_3citrate.2H_2O$ and 130 g of sucrose (40% w/w) are added consecutively. In this example DMEM represents 6% w/w. Formulations 26-29 were made similarly, expected that sucrose and DMEM concentrations were slightly modified (see Table 44). Formulation 30 was prepared by mixing 0.1653 g $NaH_2PO_4.2H_2O$, 0.1884 g of $Na_2HPO_4.2H_2O$, 32.16 g of $Na_3citrate.2H_2O$ and 130 g of sucrose (40% w/w) are added consecutively. In this example DMEM represents 6% w/w. Formulations 31 and 32 were made similarly, expected that sucrose and DMEM concentrations were slightly modified (see Table 44).

Despite the fact that, in formulations 25-29, the total phosphate concentration was 0.45 M, i.e. below the theoretical solubility limit of 0.52 M for $Na_2HPO_4$, some of the formulations (for example formulations 26 and 28) exhibited recrystallisation during +4° C. storage. This practical difference between the theoretical solubility value and the practical one is probably due to the presence of other compounds dissolved in the medium (sucrose, citrate or others imported via the DMEM medium), although inconsistent results were obtained for similar formulations (compare for example formulations 26 and 27). The variability experienced with such formulations is not compatible with the reliability needed when preparing large scale formulations that have to remain physically stable over a minimum period of time.

Decreasing even further the amount of phosphate in the formula (see no 30-32 and 38-40 in Table 44) gives poor results in the 4-8° C. viral stability (see Table 47).

Other 1.5 ml dose volume formulations (18-24) have also been made in the absence of added phosphate (see Table 44 for details). The antacid capacity for these formulations was maintained at the target value of 12 min using trisodium citrate at a higher concentration (438 mM). Briefly, formulation 18 was prepared by mixing water 143.34 g (quantity determined so as to reach a final 325 g preparation), 32.16 g of $Na_3citrate.2H_2O$ and 130 g of sucrose (40% w/w) are added consecutively. For formulations no 19-23 various quantities of sucrose and DMEM were tested (see Table 44). For formulation 24, sucrose was used at a 50% w/w concentration (162.5 g). In these formulations, DMEM represents 6% w/w.

The pH of these formulations (no 18-24) exceeded 8.3, at which rotavirus stability is affected as evidenced by a viral loss higher than 0.8 after one week storage at 37° C.

Given the poor stability of these formulations during the rapid test at 37° C., no mid-term stability plan at either room temperature or 4° C. was conducted.

Those results indicate that, when less and less phosphate is included in the formulation, with more and more citrate (to maintain the antacid capacity), then, the resulting pH of the formulation is increasing more and more:
pH around 6.7 in formulations 25-29
pH around 7.7 in formulations 30-32 and 38-40, and
pH around 8.3 in formulations without phosphate no 18-24
As shown hereafter (Table 46 and 47) those higher pH value are not in favour of a good rotavirus stability.

Additionally, those results are in accordance with the results obtained for formulations 110-115 (see Table 5) and 128-130 (see Table 6) where the pH was corrected by adjusting the citric-acid/sodium citrate ratio only (thus without additional phosphate).

IV.2. Rotavirus Viral Titration and Antacid Capacity

Rotavirus viral titration at different points in time has been evaluated according to the procedure given in Example III.1 and the antacid capacity of the formulation has been evaluated following the protocol given in Example III.2. The results are illustrated in Tables 46 and 47.

TABLE 46

Viral stability at room temperature

Viral titration after storage at room temperature (20-22° C.)
($\log_{10}$ ffu per vaccine dose)

| n° | 1 month | 2 months | 3 months | 4 months | 5 months | 6 months |
|---|---|---|---|---|---|---|
| 1 | 6.0 | 6.0 | 5.8 | 5.6 | | 5.1 |
| 2 | 6.3 | 5.9 | 6.0 | 5.6 | | 5.0 |
| 3 | 6.2 | 6.0 | 5.9 | 5.5 | | 5.0 |
| 4 | 6.0 | 6.0 | 5.5 | 5.0 | | |
| 5 | 6.0 | 5.7 | 5.3 | 4.5 | | |
| 6 | 5.5 | 5.1 | 4.8 | | | |
| 7 | ∞ | ∞ | ∞ | ∞ | ∞ | ∞ |
| 8 | 6.0 | 5.6 | 5.5 | 4.9 | | |
| 9 | 5.9 | 5.6 | 5.1 | | | |
| 10 | 5.6 | 5.1 | 4.6 | | | |
| 11 | ∞ | ∞ | ∞ | ∞ | ∞ | ∞ |
| 17 | 6.0 | 5.8 | 5.8 | 5.7 | | 5.0 |
| 25 | 5.9 | 5.5 | 4.8 | | | |
| 27 | 5.8 | 5.1 | 4.7 | | | |
| 29 | 6.1 | 5.7 | 5.5 | 5.4 | | 3.9 |
| 31 | 5.7 | 5.3 | 4.7 | | | |
| 32 | 5.9 | 5.5 | 5.0 | | | |
| 38 | ∞ | ∞ | ∞ | ∞ | ∞ | ∞ |
| 39 | | 5.3 | 5.5 | 4.5 | | |
| 40 | | 5.5 | 5.2 | 4.8 | | 4.6 |

Blank boxes = not determined
∞ Formulations 7, 11 and 38 discarded from the long term stability because of poor results obtained during the 1 week at 37° C. test

TABLE 47

Viral stability at 4° C.

Viral titration after storage at 4° C. ($\log_{10}$ ffu per vaccine dose)

| n° | T = 0 | after 1 w 37° C. | 1 m* 4° C. | 2 m* 4° C. | 4 m* 4° C. | 6 m* 4° C. | 7 m* 4° C. | 9 m* 4° C. | 12 m* 4° C. |
|---|---|---|---|---|---|---|---|---|---|
| 1 | 5.9 | 5.4 | 5.9 | 6.0 | 6.1 | 6.1 | | 5.9 | 5.9 |
| 2 | 5.8 | 5.4 | 5.9 | 6 | 6 | 6 | | 5.9 | 5.8 |

TABLE 47-continued

Viral stability at 4° C.

Viral titration after storage at 4° C. ($\log_{10}$ ffu per vaccine dose)

| n° | T = 0 | after 1 w 37° C. | 1 m* 4° C. | 2 m* 4° C. | 4 m* 4° C. | 6 m* 4° C. | 7 m* 4° C. | 9 m* 4° C. | 12 m* 4° C. |
|---|---|---|---|---|---|---|---|---|---|
| 3 | 5.6 | 5.3 | 6 | 6 | 6.2 | 6 | | 6 | 5.9 |
| 4 | 5.8 | 5.3 | 5.7 | 6.0 | 6.1 | | 5.9 | 5.9 | 5.7 |
| 5 | 5.8 | 5.5 | 6.1 | 6.1 | 6.1 | | 5.8 | 6.0 | 5.7 |
| 6 | 5.7 | 5.5 | 6.0 | 6.0 | 5.9 | | 5.4 | 5.6 | 4.9 |
| 7 | 5.6 | 4.1 | | | | | | | |
| 8 | 5.7 | 5.4 | 5.9 | 6.0 | 5.9 | | 5.8 | 5.9 | 5.6 |
| 9 | 6.1 | 5.6 | 6.1 | 6.1 | 5.8 | | 5.7 | 5.6 | 5.5 |
| 10 | 6.1 | 5.4 | 6.0 | 5.5 | 5.5 | | | | |
| 11 | 6.1 | 4.4 | | | | | | | |
| 17 | 5.7 | 5.5 | 5.7 | 5.9 | 6 | 5.8 | | 5.9 | 5.9 |
| 25 | 6.2 | 5.8 | 5.9 | 5.9 | NA* | NA* | | NA* | NA* |
| 27 | 6.2 | 6.0 | 6 | 5.8 | NA* | NA* | | NA* | |
| 29 | 6.1 | 6.1 | 6.1 | 5.9 | 5.9 | 6.2 | | | |
| 31 | 6.1 | 5.8 | 5.7 | 5.7 | 5.6 | 5.6 | | | |
| 32 | 6.0 | 5.7 | 6 | 5.8 | 5.6 | 5.6 | | | |
| 38 | 5.7 | 5.2 | | | | | | | |
| 39 | 5.6 | 5.3 | | 5.7 | 5.4 | | | | |
| 40 | 5.6 | 5.4 | | 5.7 | 5.3 | | | | |

*NA = not available - failed during the stability test at room temperature
Blank boxes = not determined IV.3. Results and Conclusions Formulations 2-3 (Dose Volume of 2.5 ml) and Formulation 17 (Dose Volume Decreased from 2.5 ml to 2 ml):

As shown in Tables 46 and 47, a 1-log loss in viral titer resulted from a 6-month storage at room temperature for formulations 2, 3 and 17. At 4° C., no significant loss of viral titer was experienced over a storage period of up to 12 months.

Formulations 25, 27, 29 and 31-32 (Dose Volume Decreased to 1.5 ml):

At room temperature, a 1-log loss in viral titration was generally reached at 3 months or earlier, except for formulation 29 which passed the 4 months' period of time. Formulations 25 to 27 recrystallized during the storage period at 4° C., thus indicating that the decrease in phosphate concentration is not sufficient, as said above. Therefore such formulations are not suitable for storage periods which would be of at least one year at 4° C.

When decreasing the phosphate concentration even further (formulations 30-32), the pH of the final formulation increases due to the relatively increasing amount of citrate, which is needed to maintain the same value of antacid capacity. This increase of pH affects the stability of the rotavirus and can be detected rapidly during the room temperature stability study. Those tendencies are confirmed when taking out completely the phosphate out the formulation (formulations 18 and 24).

Overall Conclusion of Example IV

These results indicate that, in order to reach a dose volume of below 2 ml, compared to a dose volume of 2.5 ml, the amount of phosphate present in the formulation must be reduced, due to its rather low water solubility and its propency to recrystallise. As a consequence, in order to keep the same target value of antacid capacity (i.e. a minimum of at least 8 min, suitably at least 12 min as assessed by the BRR test), the citrate salt quantity must be increased. This generates an increase in the final pH of the formulation, which is detrimental for the stability of the rotavirus in the liquid formulation.

Example V

Additional Formulations

The following formulations were prepared (Table 48), but were not included in the long-term stability planning for failure to meet at least one of the set criteria. Specific reasons for discarding some formulations are outlined in the comments column of Table 48.

TABLE 48

| N° | Brief description of formulation | Reference formulation + Table | Comments |
|---|---|---|---|
| 7 | 2.5 ml; Citrate; phosphate; 20% sucrose | IV.1 table 43 | >1 log loss at 1week 37° C. |
| 11 | 2.5 ml; Citrate; phosphate; 20% sucrose | IV.1 table 43 | >1 log loss at 1week 37° C. |
| 12 | 1.5 ml; Citrate; phosphate; 40% sucrose | IV.1 table 43 | Crystallize on standing at +4° C. |
| 13 | 1.5 ml; Citrate; phosphate; 40% sucrose | IV.1 table 43 | Crystallize on standing at +4° C. |
| 14 | 1.5 ml; Citrate; phosphate; 40% sucrose | IV.1 table 43 | Crystallize on standing at +4° C. |
| 15 | 1.5 ml; Citrate; phosphate; 45% sucrose | IV.1 table 43 | Crystallize on standing at +4° C. |
| 16 | 1.5 ml; Citrate; phosphate; 45% sucrose | IV.1 table 43 | Crystallize on standing at +4° C. |
| 18 | 1.5 ml; Citrate; 40% sucrose; pH 8.42 | IV.1 table 44 | >1 log loss at 1week 37° C. |
| 19 | 1.5 ml; Citrate; 40% sucrose; pH 8.42 | IV.1 table 44 | >1 log loss at 1week 37° C. |
| 20 | 1.5 ml; Citrate; 40% sucrose; pH 8.31 | IV.1 table 44 | >1 log loss at 1week 37° C. |
| 21 | 1.5 ml; Citrate; 45% sucrose; pH 8.35 | IV.1 table 44 | >1 log loss at 1week 37° C. |
| 22 | 1.5 ml; Citrate; 45% sucrose; pH 8.35 | IV.1 table 44 | >1 log loss at 1week 37° C. |
| 23 | 1.5 ml; Citrate; 45% sucrose; pH 8.37 | IV.1 table 44 | >1 log loss at 1week 37° C. |
| 24 | 1.5 ml; Citrate; 50% sucrose; pH 8.31 | IV.1 table 44 | >1 log loss at 1week 37° C. |

TABLE 48-continued

| N° | Brief description of formulation | Reference formulation + Table | Comments |
|---|---|---|---|
| 25 | 1.5 ml; Citrate; phosphate; 40% sucrose | IV.1 table 44 | Risk of crystallization at +4° C. |
| 26 | 1.5 ml; Citrate; phosphate; 40% sucrose | IV.1 table 44 | Crystallize on standing at +4° C. |
| 27 | 1.5 ml; Citrate phosphate; 40% sucrose | IV.1 table 44 | Risk of crystallization at +4° C. |
| 28 | 1.5 ml; Citrate phosphate; 45% sucrose | IV.1 table 44 | Crystallize on standing at +4° C. |
| 29 | 1.5 ml; Citrate phosphate; 45% sucrose | IV.1 table 44 | Risk of crystallization at +4° C. |
| 30 | 1.5 ml; Citrate phosphate 40% sucrose | IV.1 table 44 | 0.8 log loss at 1week 37° C. |
| 33 | 1.5 ml; Acetate + Calcium | II.1 table 10 | >1 log loss at 1week 37° C. |
| 34 | 1.5 ml; Acetate + Calcium | II.1 table 10 | >1 log loss at 1week 37° C. |
| 35 | 1.5 ml; Acetate + Calcium | II.1 table 10 | >1 log loss at 1week 37° C. |
| 41 | 1.5 ml Glutamate; 50% sucrose | II.7 table 36 | pH too high: 10.36 |
| 44 | 1.75 ml; Fumarate; 44% sucrose | II.8 | Insoluble materials |
| 45 | 1.75 ml; Adipate; 44% sucrose | II.5 table 19 | BRR too long: >29 min. |
| 47 | 1.75 ml; Lactobionate; 31% sucrose | II.9 | BRR too short: <1 min. |
| 48 | 1.75 ml; Maleate; 44% sucrose | II.10 | pH too high: 10.4, BRR too long: 24 min. |
| 49 | 1.75 ml; Glucuronate; 42% sucrose | II.11 | pH too high: 8.45; BRR too short: <1 min. |
| 50 | 1.75 ml; Glutarate; 44% sucrose | II.4 table 18 | BRR too long: >29 min. |
| 51 | 1.75 ml; Succinate; 44% sucrose | II.3 table 16 | BRR too long: >29 min. |
| 52 | 1.75 ml; Galacturonate; 42% sucrose | II.12 | pH too high: 10.69, BRR too short: <1 min. |
| 53 | 1.75 ml; Galactarate; 38% sucrose | II.13 | Insoluble materials |
| 54 | 1.75 ml; Malonate; 44% sucrose | II.2 table 14 | pH too high: 8.36 |
| 55 | 1.75 ml; Tartrarate; 44% sucrose | II.14 | BRR to short: <1 min. |
| 57 | 1.75 ml; Maleate; 44% sucrose | II.10 | >1 log loss at 1week 37° C. |
| 68 | 1.5 ml; Glutamate; 7.5% sucrose | II.7 table 36 | >1 log loss at 1week 37° C. |
| 73 | 1.5 ml; Malate 0.597M; 50% sucrose | II.6 table 33 | Sterile filtration too difficult |
| 75 | 1.5 ml; Malate; 56% sucrose | II.6 table 33 | Difficulties in sucrose solubilisation |
| 103 | 1.5 ml; Adipate; 55% sucrose; pH 5.09 | II.5.1 table 19 | Adipic acid crystallizes on standing at +4° C. |
| 104 | 1.5 ml; Adipate; 55% sucrose; pH 5.12 | II.5.1 table 19 | Adipic acid crystallizes on standing at +4° C. |
| 107 | 1.5 ml; Adipate 0.466M; 55% sucrose | II.5.1 table 19 | Ok but similar stability data already ongoing |
| 108 | 1.5 ml; Adipate 0.63M; 53.15% sucrose; pH 5.38 | II.5.1 table 19 | Adipic acid crystallizes on standing at +4° C. |
| 109 | 1.5 ml; Adipate 0.63M; 55% sucrose; pH 5.38 | II.5.1 table 19 | Adipic acid crystallizes on standing at +4° C. |
| 117 | 1.5 ml; Adipate; 55% sucrose; Ca++ | II.5.4 table 26 | Precipitation of calcium adipate |
| 121 | 1.5 ml; Adipate; 55% sucrose; Ca++ | II.5.4 table 26 | Precipitation of calcium adipate |
| 135 | 1.5 ml, adipate; 55% sucrose | as n°134 | Placebo without rotavirus |
| 136 | 1.5 ml; Adipate; 55% sucrose | II.5.1 table 19 | pH too high: 9.36 |
| 137 | 1.5 ml; Adipate; 55% sucrose | II.5.1 table 19 | pH too high: 9.37 |
| 138 | 1.5 ml; Adipate; 55% sucrose | II.5.1 table 19 | pH too high: 9.67 |
| 139 | 1.5 ml; Adipate; 55% sucrose | II.5.1 table 19 | pH too high: 9.92 |
| 140 | 1.5 ml; Adipate; 55% sucrose | II.5.1 table 19 | pH too high: 10.25 |

TABLE 48-continued

| N° | Brief description of formulation | Reference formulation + Table | Comments |
|---|---|---|---|
| 141 | 1.5 ml; Adipate; 55% sucrose; pH 6.47 | II.5.1 table 19 | Ok but stability data already ongoing |
| 142 | 1.5 ml; Adipate; 55% sucrose; pH 6.30 | II.5.1 table 19 | Ok but similar stability data already ongoing |
| 146 | 1.5 ml, adipate; 50% sucrose | as n°93 | Placebo without rotavirus |
| 149 | 1.5 ml, adipate; 55% sucrose | as n°151 | Placebo without viruses |

Example VI

Phase II Immunogenicity, Reactogenicity and Safety of Two Oral Doses of a Human Monovalent Rotavirus Liquid Vaccine in Healthy Infants VI.1. Introduction A phase II randomised, double-blind, placebo-controlled phase II trial was conducted to evaluate the immunogenicity, reactogenicity and safety of a vaccine containing a human attenuated G1P8 rotavirus strain (deposited at ECAAC under deposit number 99081301 see WO 01/12797), for infant immunisation. The study was performed in multiple centers in Finland. An overview of the study design is given in FIG. 4.

During this trial, a first dose of the vaccine, either the liquid formulation of the candidate HRV (human rotavirus) vaccine (N=100) or the lyophilized formulation of the HRV vaccine (N=100) and respective placebo (2 groups with each N=25) was administered at around 2.5 months of age (between 6 and 12 weeks of age), at the time of a first visit to the doctor. A second dose was administered at around 3.5 months of age (during the second visit to the doctor, typically 4 weeks after the first dose). A follow-up visit was performed 1 month after the second dose, at around 4.5 months of age for a blood draw and evaluation of immunogenicity.

The clinical trial was randomized, placebo-controlled and self-contained. A total of 250 subjects, 100 per HRV group and 25 per placebo group, were enrolled. It was conducted in a double-blind manner between each HRV vaccine formulation and its respective placebo. However, between the 2 different formulations blinding was technically not possible.

Routine childhood vaccinations were given according to local practice, but at least 14 days apart from each dose of the HRV vaccine.

VI.2. Description of the Vaccine

Specifically the vaccine used comprises as the rotavirus component the attenuated G1 human strain deposited as ECACC deposit 99081301 (WO 01/12797).

The vaccine is an attenuated human rotavirus (HRV) candidate vaccine derived from the 89-12 HRV strain belonging to the serotype G1P1A and genotype [P8] that was isolated from stool of a 15-month old child in Cincinnati, USA. Natural infection with the 89-12 strain was shown to provide protection against subsequent illness and against reinfection in a two-year prospective study (Bernstein D I, et al. Protection from rotavirus reinfection: 2 years prospective study. *J Infect Dis*. 1991; 164: 277-83).

The antacid will prevent inactivation of the HRV during passage through the stomach.

Table 49 compares the compositions of the adipate liquid formulation and a lyophilized formulation prepared according to WO 01/12797 and demonstrated to be efficacious in a large-scale clinical trial (De Vos et al. Pediatr Infect Dis J. 2004 Oct. 23 (10 Suppl): S179-82).

TABLE 49

Quantitative composition of the adipate liquid formulation and the lyophilized formulation of the HRV vaccine (nominal dose)

| | Adipate Liquid formulation | | Lyophilized formulation (after reconstitution) | |
|---|---|---|---|---|
| Active substance | P43 strain - at least $10^{6.0}$ $CCID_{50}$ per dose at end of shelf life (1.5 ml dose volume) | | P43 strain - at least $10^{6.0}$ $CCID_{50}$ per dose at end of shelf life (1.0 ml dose volume) | |
| Stabiliser | Sucrose | 55% w/w (1.073 g) | Sucrose | 9 mg |
| | | | Dextran | 18 mg |
| | | | Sorbitol | 13.5 mg |
| | | | Aminoacids | 9 mg |
| Antacid | Di-sodium Adipate | 132.74 mg | Calcium carbonate | 60 mg |
| Thickening agent | — | | Xanthan | 2.5 mg |
| Bulk diluent | DMEM** | 6% w/w | DMEM** | 2.25 mg |
| Solvent | Water for injection | q.s. ad 1.5 ml | Water for injection | q.s. ad 1 ml |

**Dulbecco's Modified Eagle Medium

A summary of the volume and antacid capacity of the two formulations of the HRV vaccine is presented in Table 50.

TABLE 50

Volume and antacid capacity of the adipate liquid formulation and the lyophilised formulation of the HRV vaccine

| Formulation | Filling volume per dose | Antacid capacity (BRR* in min) |
|---|---|---|
| Adipate liquid HRV vaccine | 1.5 ml | 12 |
| Lyophilized formulation | 1.3 ml | 17 |

*BRR = Baby Rossett-Rice (BRR) titration test: to measure the rate of reaction of the antacid substance with 0.1 N hydrochloric acid and the duration of maintenance to a pH above 4. See procedure in Example III.2.2.

Monodoses of the formulated adipate liquid HRV vaccine are filled according to Good Manufacturing Practices (GMP), into monodose glass syringes.

Rotavirus viral titer (i.e. rotavirus potency) may be measured according to the procedure detailed in Example III.1, with MA104 infected cells being identified by indirect immuno-fluorescence. Alternatively it is measured by in vitro titration of the virus on MA104 cells with virus detected by direct immuno-fluorescence using specific anti-rotavirus antibodies. The method determines the dose infecting 50% of the cell culture and rotavirus titers are expressed in median Cell Culture Infective Dose ($CCID_{50}$). The inter- and intra-assay reproducibility has been evaluated and gives equivalent results (variability is assessed at 0.3 log).

VI.3. Administration

VI.3.1. Lyophilized Formulation of HRV Vaccine or Placebo

To prepare the vaccine or placebo for administration, the entire content of one pre-filled syringe containing the calcium carbonate buffer was injected into the vial of the lyophilized product (vaccine or placebo) and the resuspended product was then administered smoothly as a single oral dose.

VI.3.2. Liquid Formulation of HRV Vaccine or Placebo

The pre-filled glass syringe was shaken before use. The product (vaccine or placebo) was then administered smoothly as a single oral dose.

VI.4. Safety and Reactogenicity

The following criteria of safety and reactogenicity applied: solicited general adverse events were fever, irritability/fussiness, diarrhoea, vomiting, loss of appetite and cough/runny nose. They were recorded during 15 days after each study vaccine dose, using diary cards provided to the parents/guardians of the subjects to record the observed symptoms. All gastroenteritis events (diarrhoea) occurring between visits were documented, and stool samples were collected (at the latest 7 days after onset of the gastroenteritis). Unsolicited adverse events occurring within 31 days after each dose were recorded. Serious adverse events were recorded during the entire study period.

VI.5. Laboratory Assays

VI.5.1. Stool Analysis

Stool samples collected from all subjects on the day of or one day prior to each study vaccine dose, on Day 7±1 and on Day 15±1 after each dose, and on the day of or one day prior to Visit 3 are being analyzed at GSK Biologicals or a laboratory designated by GSK Biologicals to detect the presence of vaccine RV using Enzyme Linked Immunosorbent Assay (ELISA—see section VI.6.1) to assess viral shedding.

Presence of rotavirus antigen demonstrated by ELISA in any stool collected at pre-determined time points after Dose 1 up to Visit 3 are considered as vaccine virus shedding and taken as evidence of a vaccine response (i.e. vaccine take), if the subject was negative for rotavirus on the day of Dose 1 of HRV vaccine or placebo. For placebo subjects sequencing is performed in this case.

A subject initially negative for rotavirus is defined as a subject who was negative for anti-rotavirus IgA antibodies in serum and for rotavirus antigen in a stool sample at a pre-vaccination time point, if both results are available, or negative for at least one of these markers if only one result is available.

Also, stool samples collected during each GE episode from Visit 1 until Visit 3 are being tested at GSK Biologicals or a laboratory designated by GSK Biologicals using ELISA to detect RV. If positive, the G type is determined using PCR-based approaches. These molecular methods target regions within the VP7 gene which are very distinct among different G types and are highly conserved within each given G type. For example, the RT-PCR method developed by Gouvea et al. (1990, J Clin Microbiol., 28:276-282) uses a cocktail of different genotype-specific primers, located in different regions of the VP7 gene. The size of the resulting PCR products estimated by gel electrophoresis provides the information to identify the corresponding G-genotypes. If any G1 RV is detected, vaccine virus is differentiated from the wild type serotype by sequence analysis or an equivalent approach.

Any detection of vaccine virus in any stool collected up to Visit 3 is taken as evidence of a vaccine response (i.e. vaccine take).

VI.5.1. Serum Analysis

Serum obtained from whole blood samples collected from subjects at each study visit were tested by ELISA at GSK Biologicals' designated laboratory to measure serum anti-rotavirus IgA antibody concentrations. The assay cut-off is 20 U/ml. A seronegative subject for anti-rotavirus IgA antibodies was defined as a subject who had antibody concentration below the assay cut-off value. A seropositive subject for anti-rotavirus IgA antibodies was defined as a subject who had antibody concentration greater than or equal to the assay cut-off value.

VI.6. Immunogenicity: Serum Analysis

VI.6.1. Measurement of IgA Antibodies by ELISA

This assay allows the detection of rotavirus IgA in human serum and was initially designed by R. Ward (1, 2) and has been adapted by GSK Biologicals. It was used for measuring the immune response after vaccination and/or infection. Samples were analyzed at GSK Biologicals, Rixensart, Belgium (or designated laboratory).

Description of the ELISA Assay 96-well plates are coated by overnight incubation with anti-rotavirus antibody dilutions. The wells are washed and a lysate of cells either infected with vaccine strain (positive wells) or either uninfected (negative wells) is added. Following incubation on a rotating platform, the plates are washed and the dilutions of serum samples or standard serum are incubated in both kinds of wells (positive and negative). The use of negative wells allows the assessment of non-specific IgA binding.

The plates are washed and bound human IgA is detected by addition of biotinylated rabbit anti-human IgA (30 minutes under agitation). After washing the plates, peroxidase-conjugated avidin-biotin at an optimal concentration is added to each well and incubated (30 minutes, RT under agitation). Plates are again washed and orthophenylenediamine (OPD) is added. The plates are then incubated (30 minutes, room temperature (RT) in darkness) before the reaction is stopped with 2N H2SO4. Optical absorption is measured at 490/620 nm. Specific optical densities are calculated for each sample/standard by measuring the difference between positive and negative wells. Concentrations of the samples are determined by using the four-parameter logistic function generated by the standard curve. The most accurate part of the standard curve (working range) for the calculation of the results is determined. Antibody concentrations in units per milliliter (U/ml) are calculated relative to the standard (concentration=1000 U/ml) by averaging the values for each unknown that fall within the working range of the standard curve and then corrected for the dilution factor. Each experiment includes negative and positive controls. For all reagents optimal concentration are pre-determined.

REFERENCES

1. Bernstein D I, Smith V E, Sherwood J R et al. Safety and immunogenicity of a live attenuated human rotavirus 89-12 vaccine. Vaccine. 1998; 16:381-7.
2. Bernstein D I, Sack D A, Rothstein E et al. Efficacy of live attenuated human rotavirus vaccine 89-12 in infants: a randomised placebo-controlled trial. Lancet. 1999; 354: 287-90.

VI.7. Results: Anti-Rotavirus IgA Antibody Response

Table 51 presents the anti-rotavirus IgA antibody GMC and seroconversion rates (Total vaccinated cohort for immunogenicity). Table 52 presents the anti-rotavirus IgA antibody GMC calculated on subjects seropositive for anti-rotavirus IgA antibodies calculated on the total vaccinated cohort.

The antibody response to HRV vaccine in terms of seroconversion rates was similar in both the vaccine groups one month after second dose (82.2% in HRV_Lyo group and 90.1% in the HRV_Liq group). In the pooled placebo group, 0% subjects seroconverted one month after second dose, indicating the study was conducted at a time when there were no wild type infections in the community.

TABLE 51

Anti-rotavirus IgA antibody GMC and seropositivity rates - Total vaccinated cohort for immunogenicity

| Group | Timing | N | ≧20 U/ML | | | | GMC | | |
|---|---|---|---|---|---|---|---|---|---|
| | | | n | % | 95% CI LL | 95% CI UL | value | 95% CI LL | 95% CI UL |
| HRV_LYO | PRE | 98 | 0 | 0.0 | 0.0 | 3.7 | <20 | — | — |
| | PI(M1) | 96 | 68 | 70.8 | 60.7 | 79.7 | 191.3 | 122.7 | 298.2 |
| | PII(M2) | 90 | 74 | 82.2 | 72.7 | 89.5 | 330.4 | 217.5 | 502.0 |
| HRV_LIQ | PRE | 98 | 0 | 0.0 | 0.0 | 3.7 | <20 | — | — |
| | PI(M1) | 87 | 66 | 75.9 | 65.5 | 84.4 | 172.9 | 112.1 | 266.7 |
| | PII(M2) | 81 | 73 | 90.1 | 81.5 | 95.6 | 292.3 | 199.3 | 428.8 |
| PL_POOL | PRE | 49 | 0 | 0.0 | 0.0 | 7.3 | <20 | — | — |
| | PI(M1) | 46 | 0 | 0.0 | 0.0 | 7.7 | <20 | — | — |
| | PII(M2) | 48 | 0 | 0.0 | 0.0 | 7.4 | <20 | — | — |

1. N = number of subjects with available results
2. n/% = number/percentage of subjects with concentration above the cut-off
3. 95% CI = 95% confidence interval; LL = Lower Limit, UL = Upper Limit
4. PRE = pre-vaccination
5. PI(M1) = one months after the first dose of HRV vaccine or placebo (visit 2)
6. PII(M2) = one month after the second dose of HRV vaccine or placebo (visit 3)
7. Database release = 07DEC2005

TABLE 52

Anti-rotavirus IgA antibody GMC calculated on subjects seropositive for anti-rotavirus IgA antibodies - Total vaccinated cohort for immunogenicity

| Group | Timing | N | GMC value | 95% CI LL | 95% CI UL |
|---|---|---|---|---|---|
| HRV_LYO | PI(M1) | 68 | 644.7 | 471.4 | 881.8 |
| | PII(M2) | 74 | 703.8 | 525.0 | 943.6 |
| HRV_LIQ | PI(M1) | 66 | 428.1 | 302.1 | 606.8 |
| | PII(M2) | 73 | 423.1 | 305.9 | 585.2 |

1. N = number of subjects who were seropositive for anti-rotavirus IgA antibodies
2. 95% CI = 95% confidence interval; LL = Lower Limit, UL = Upper Limit
3. PI(M1) = one months after the first dose of HRV vaccine or placebo (visit 2)
4. PII(M2) = one month after the second dose of HRV vaccine or placebo (visit 3)
5. Database release = 07DEC2005

VI.8. Conclusions

The immunogenicity in terms of seroconversion rates was similar between the two vaccine formulations.

The liquid formulation of the vaccine was very immunogenic when administered to children according to 0, 1 months schedule.

As IgA is a good marker for the efficacy of a rotavirus vaccine, these data support the protective effect of the formulation tested in the clinics.

The invention claimed is:

1. A liquid rotavirus immunogenic composition suitable for oral administration to a human infant, comprising a live attenuated rotavirus antigen, a sugar and a carboxylate wherein said formulation has a pH of between about pH 5.0 and about pH 8.0 and comprises less than 1 mM phosphate, wherein said carboxylate is a carboxylate salt of adipate.

2. The liquid composition according to claim 1, wherein said composition comprises less than 0.1 mM phosphate.

3. The liquid composition according to claim 1, wherein said composition is free of phosphate.

4. The liquid composition according to claim 1, wherein the pH of said composition is between about pH 5.5 to about pH 7.5.

5. The liquid composition according to claim 4, wherein the pH of said composition is between about pH 6.0 and about pH 7.0.

6. The liquid composition according to claim 1, wherein said carboxylate is present at a concentration of between about 50 mM and about 2 M.

7. The liquid composition according to claim 6, wherein said carboxylate is present at a concentration of between about 100 mM and about 1 M.

8. The liquid composition according to claim 7, wherein said carboxylate is present at a concentration of between about 400 mM and about 700 mM.

9. The liquid composition according to claim 1, wherein said sugar is selected from the list consisting of: glycerol, erythrose, erythriol, xylitol, arabitol, ribose, xylose, arabinose, glucose, tagalose, mannose, galactose, fructose, inositol, sorbitol, mannitol, galactitol, a combination of glucose and fructose, maltose, sophorose, lactose, cellobiose, melibiose, trehalose, sucrose, palatinose, maltulose, lactulose, maltitol, lactitol, raffinose, maltotriose, melezitose, cellotriose, ciritol, maltotetraose, stachyose, cellotetraose, maltopentaose, cellopentaose, maltohexaose, cellohexaose, oligosaccharides.

10. The liquid composition of claim 9, wherein said sugar is sucrose or dextrose.

11. The liquid composition according to claim 1, wherein the concentration of said sugar is between about 35% w/w and about 70% w/w.

12. The liquid composition according to claim 11, wherein the concentration of said sugar is between about 40% w/w and about 70% w/w.

13. The liquid composition according to claim 12, wherein the concentration of said sugar is between about 50% w/w and about 55% w/w.

14. The liquid composition according to claim 1, additionally comprising a carboxylic acid.

15. The liquid composition according to claim 14, wherein said carboxylic acid is adipic acid.

16. The liquid composition according to claim 1, further comprising calcium ions.

17. The liquid composition according to claim 1, wherein said live attenuated rotavirus is a live attenuated human rotavirus.

18. The liquid composition according to claim 17, wherein said live attenuated human rotavirus is selected from the group consisting of: HRV 89-1 2C2 strain deposited under accession number ATCC VR 2272, progeny, reassortants and immunologically active derivatives thereof; HRV P43 strain deposited under accession number ECACC 99081301, progeny, reassortants and immunologically active derivatives thereof.

19. The liquid composition according to claim 1, wherein said composition has an antacid capacity of at least 8 minutes as assessed by the Baby Rossett-Rice assay.

20. The liquid composition according to claim 19, wherein said composition has an antacid capacity of at least 12 minutes as assessed by the Baby Rossett-Rice assay.

21. The liquid composition according to claim 1 wherein said composition is stable under at least one of the following conditions: for 7 days at 37° C., for one year at 4° C., for two years at 4° C.

22. The liquid composition according to claim 1, which is a vaccine.

23. The liquid composition as claimed in claim 1, wherein said composition is provided in a dose volume of between 0.2 ml and 2.0 ml.

24. The liquid composition as claimed in claim 23, wherein said composition is provided in a dose volume of between 0.5 ml and 1.5 ml.

25. A method of prevention of rotavirus associated diseases in humans by administering to a human subject in need thereof an effective amount of a liquid formulation according to claim 1.

26. The method as claimed in claim 25, comprising administering the liquid formulation for the prevention of rotavirus gastroenteritis in humans.

27. The method as claimed in claim 26, comprising administering the liquid formulation for prevention of rotavirus severe gastroenteritis in humans.

28. The method as claimed in claim 26, wherein said gastroenteritis or severe gastroenteritis is caused by a rotavirus strain of a different serotype from that of the rotavirus strain contained in said liquid formulation.

29. The method as claimed in claim 25, wherein said composition is provided in a dose volume of between 0.2 ml and 2.0 ml.

30. The method as claimed in claim 29, wherein said composition is provided in a dose volume of between 0.5 ml and 1.5 ml.

31. A method for the preparation of a liquid rotavirus composition according to claim 1 comprising admixing a rotavirus antigen, a sugar and a carboxylate with a pharmaceutically acceptable diluent.

32. The method according to claim 25, wherein said prevention comprises administering two oral doses of a safe and effective amount of the human live attenuated rotavirus composition to an infant within 4-15 weeks of age at the time of dose 1.

33. The liquid composition according to claim 1, wherein said carboxylate is a carboxylate salt that is sodium adipate having the formula $Na_2C_6H_8O_4$.

* * * * *